(12) United States Patent
West et al.

(10) Patent No.: US 10,822,406 B2
(45) Date of Patent: Nov. 3, 2020

(54) METHOD FOR TREATING CHRONIC INTESTINAL INFLAMMATION AND INFLAMMATORY BOWEL DISEASE BY ADMINISTERING ANTAGONISTS OF ONCOSTATIN-M (OSM) AND/OR ANTAGONISTS OF OSM RECEPTOR-BETA (OSMR)

(71) Applicant: Oxford University Innovation Limited, Oxford (GB)

(72) Inventors: Nathaniel Richard West, Oxford (GB); Benjamin Michael Joseph Owens, Oxford (GB); Ahmed Nabil Hegazy, Oxford (GB); Fiona Margaret Powrie, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 0 days.

(21) Appl. No.: 15/547,154

(22) PCT Filed: Jan. 28, 2016

(86) PCT No.: PCT/GB2016/050185
§ 371 (c)(1),
(2) Date: Jul. 28, 2017

(87) PCT Pub. No.: WO2016/120625
PCT Pub. Date: Aug. 4, 2016

(65) Prior Publication Data
US 2018/0022800 A1 Jan. 25, 2018

(30) Foreign Application Priority Data
Jan. 29, 2015 (GB) .................... 1501480.6
Jan. 29, 2015 (GB) .................... 1501511.8
Dec. 4, 2015 (GB) .................... 1521446.3

(51) Int. Cl.
| A61K 38/17 | (2006.01) |
| A61K 39/00 | (2006.01) |
| C07K 16/24 | (2006.01) |
| G01N 33/68 | (2006.01) |
| A61K 31/56 | (2006.01) |
| A61K 38/20 | (2006.01) |

(52) U.S. Cl.
CPC ............ *C07K 16/248* (2013.01); *A61K 31/56* (2013.01); *A61K 38/1793* (2013.01); *A61K 38/204* (2013.01); *C07K 16/241* (2013.01); *G01N 33/6869* (2013.01); *A61K 2039/505* (2013.01); *C07K 2317/24* (2013.01); *C07K 2317/76* (2013.01); *G01N 2333/5412* (2013.01); *G01N 2800/065* (2013.01); *G01N 2800/52* (2013.01)

(58) Field of Classification Search
CPC ............. C07K 16/241; C07K 16/248; C07K 2317/24; C07K 2317/76; A61K 31/56; A61K 38/1793; A61K 38/204; A61K 2039/505; G01N 33/6869; G01N 2800/065; G01N 2800/52; G01N 2333/5412
See application file for complete search history.

(56) References Cited

U.S. PATENT DOCUMENTS

| 5,958,442 A | 9/1999 | Wallace et al. |
| 2007/0160611 A1 | 7/2007 | Yao et al. |
| 2008/0293582 A1 | 11/2008 | Li et al. |
| 2009/0054253 A1 | 2/2009 | Li et al. |
| 2011/0160157 A1 | 6/2011 | Wang et al. |
| 2012/0142755 A1 | 6/2012 | Lecron et al. |
| 2014/0099315 A1 | 4/2014 | Almagro et al. |

FOREIGN PATENT DOCUMENTS

| JP | 2009526756 A | 7/2009 |
| WO | 99/48523 A2 | 9/1999 |
| WO | 2008/028031 A2 | 3/2008 |
| WO | 2010/044952 A2 | 4/2010 |
| WO | 2012/044952 A2 | 4/2012 |
| WO | 2012/069433 A2 | 5/2012 |
| WO | 2013/168829 A1 | 11/2013 |
| WO | 2014/186728 A2 | 11/2014 |
| WO | 2014/194274 A2 | 12/2014 |

OTHER PUBLICATIONS

Altschul, S. F., (1993) J. Mol. Evol. 36: 290-300.
Altschul et al., (1990) J. Mol. Biol. 215:403-10.
Beigel et al., (2014) PLOS One. 9(4): e93498.
Ben-Horin and Chowers., (2014) Nat. Rev. Gastroenterol. Hepatol. 11: 243-55.
Brolund et al., (2011) BMC Biotechnology. 11:3.
Choy et al., (2013) Arthritis Research & Therapy. 15(R1 32).
Colombel et al., (2010) N. Engl. J. Med. 362(15): 1383-95.
Devereux et al., (1984) Nucleic Acids Research. 12: 387-395.
Dinarello et al., (2012) Nat. Rev. Drug. Discovery. 11(8): 633-652.
Esseku and Adeyeye (2011) Critical Reviews in Therapeutic Drug Carrier Systems. 28(5): 395-445.
Geremia et al., (2011) J. Exp. Med. 208(6): 1127-1133.

(Continued)

*Primary Examiner* — Robert S Landsman
(74) *Attorney, Agent, or Firm* — Thomas|Horstemeyer, LLP

(57) ABSTRACT

The invention relates to methods of treating chronic intestinal inflammation and/or inflammatory bowel disease by administering an antagonist of oncostatin-M (OSM) and/or OSM receptor-β (OSMR). The invention also relates to methods for diagnosing or prognosing chronic intestinal inflammation and/or inflammatory bowel disease in an individual and for predicting whether or not an individual will respond to an anti-TNFα therapy. The methods comprise measuring OSM and/or OSMR in the individual.

4 Claims, 34 Drawing Sheets

Specification includes a Sequence Listing.

(56) References Cited

OTHER PUBLICATIONS

Heinrich et al., (2003) Biochemistry. 374(1): 1-20.
Hintzen et al., (2009) Arthritis Rheum. 60(7): 1932-1943.
Izcue et al., (2008) Immunity. 28(4): 559-570.
Jostins et al., (2012) Nature. 491: 119-124.
Maddox et al., (1983) J. Exp. Med. 158: 1211-1226.
Maggio-Price et al., (2002) Am. J. Path. 160(2): 739-751.
Moran et al., Arthritis Res Ther. 2009; 11(4): R113.
Neurath, M. F., (2014) Nat. Rev. Immunol. 14: 329-342.
Owens et al., (2013) Front Immunol. 4, Article 307.
Owens, B. M. J., (2015) Front Immunol. 6, Article 319.
Panaccione et al., (2014) Gastroenterology. 46(2): 392-400.
Richards, C. D., (2013) ISRN Inflam. Article ID 512103, 23 pages.
Schiering et al., (2014) Nature. 513(7519): 564-568.
Snapper, S. B., et al., UpToDate, 2011; <https://www.uptodate.com/contents/immune-and-microbial-mechanisms-in-the-pathogenesis-of-inflammatory-bowel-disease>, pp. 1-12.
Uhlig et al., (2006) J. Immunol. 177(9): 5852-5860.
West and Watson (2010) Oncogene. 29: 2083-2092.
Japanese Office Action for Application No. 2017-540056, dated Oct. 23, 2019 (17 pages).
Loy et al., "Oncostatin M: Development of a Pleiotropic Cytokine," Toxicologic Pathology, vol. 27, No. 2, pp. 151-155, 1999 (5 pages).

METHOD FOR TREATING CHRONIC INTESTINAL INFLAMMATION AND INFLAMMATORY BOWEL DISEASE BY ADMINISTERING ANTAGONISTS OF ONCOSTATIN-M (OSM) AND/OR ANTAGONISTS OF OSM RECEPTOR-BETA (OSMR)

The research leading to these results has received funding from the People Programme (Marie Curie Actions) of the European Union's Seventh Framework Programme (FP7/2007-2013) under REA grant agreement no 330621.

FIELD OF INVENTION

The invention relates to methods and products for the treatment, diagnosis or prognosis of chronic intestinal inflammation and/or inflammatory bowel disease (IBD), and for predicting whether or not an individual will respond to treatment with an anti-tumour necrosis factor α (TNFα) therapy.

BACKGROUND TO THE INVENTION

Inflammatory diseases, such as inflammatory bowel diseases, including Crohn's disease (CD) and ulcerative colitis (UC), are debilitating chronic inflammatory conditions of the gastrointestinal tract with a relapsing-remitting course. Treatment is aimed at impairing the immune processes that drive disease, and has historically employed broadly suppressive anti-inflammatory agents such as corticosteroids. More recently, interest in targeting specific components of inflammatory pathways has grown, fuelled largely by the clinical success of anti-tumour necrosis factor-α (TNFα) antibodies such as infliximab.

While anti-TNFα antibodies can induce and sustain remission in many IBD patients, up to 40% display primary non-responsiveness and another third will lose responsiveness over time (Ben-Horin and Chowers, *Nat. Rev. Gastroenterol. Hepatol.*, 2014). There are currently no methods available to satisfactorily predict treatment failure, and no alternative cytokines have been revealed as viable clinical targets. For example, neutralization of interferon-γ (IFNγ), the primary effector cytokine of Th1 immune responses, appears to have little clinical effect. Administration of anti-inflammatory cytokines such as IL-10 and IFNβ has been similarly unsuccessful (Neurath, *Nat. Rev. Immunol.*, 2014). There is thus an urgent, twofold unmet need: (a) to identify effective biomarkers that will accurately predict the likelihood of clinical response to anti-TNFα therapies for IBD and other TNFα-mediated conditions; and (b) to identify and clinically validate alternative therapeutic targets for IBD management beyond TNFα.

IL-6 is a well-known inflammatory cytokine that is critical for driving differentiation of the Th17 subset of effector CD4$^+$ T cells. In phase II trials IL-6 receptor blockade showed modest therapeutic efficacy for CD (Neurath, *Nat. Rev. Immunol.*, 2014). IL-6 is the prototype member of a cytokine family defined by the shared use of the gp130 receptor subunit.

Oncostatin-M (OSM) is a member of this cytokine family. Unlike IL-6, which transduces signals only via gp130, OSM engages two possible heterodimeric receptors comprised of gp130 and either OSM receptor-β (OSMR) or the LIF receptor (LIFR), both of which are capable of transducing signals that are distinct from those of gp130 (Heinrich et al, *Biochemistry*, 2003). For example, OSM elicits stronger mitogen-activated protein kinase (MAPK) signalling than IL-6 in various cell types (West and Watson, *Oncogene*, 2010; Hintzen et al, *Arthritis Rheum.*, 2009). While LIFR is weakly expressed in most adult tissues, OSMR is broadly expressed by numerous cell types in most organs including endothelial, epithelial, stromal, glial, and hematopoietic cells (Richards, *ISRN Inflam.*, 2013).

Perturbation of OSM has been identified in several inflammatory disorders (such as psoriasis and airway inflammation) and multiple cancer types (Richards, *ISRN Inflam.*, 2013). In each of these conditions, experimental models demonstrate that OSM directly contributes to inflammatory processes by signalling through OSMR. OSM was recently linked to both CD and UC in genome-wide association studies (Jostins et al, *Nature*, 2012). Little is known, however, about the role of OSM signalling in IBD, including whether OSM signalling is involved in the pathogenesis of IBD.

SUMMARY OF THE INVENTION

The inventors have discovered that OSM and OSMR are highly expressed in the intestinal mucosa during active disease in the majority of IBD patients. OSM and OSMR are also upregulated in at least four different mouse models of colitis, and their expression correlates with disease severity. Deranged Th1 and Th17 helper cell activity is thought to be critical in the pathogenesis of IBD and the inventors have for the first time identified OSM as a component of the Th17 induction pathway. Moreover, systemic administration of OSM exacerbates murine colitis, whilst therapeutic blockade of OSM or genetic deletion of OSM ameliorates the immunopathology.

Accordingly, in a first aspect the invention provides a method of treating or preventing chronic intestinal inflammation and/or IBD in an individual, the method comprising administering to the individual an antagonist of OSM and/or OSMR, and thereby treating or preventing chronic intestinal inflammation and/or IBD in the individual.

The invention further provides:
  an antagonist of OSM and/or OSMR for use in a method of treating or preventing chronic intestinal inflammation and/or IBD in an individual; and
  use of an antagonist of OSM and/or OSMR in the manufacture of a medicament for use in a method of treating or preventing chronic intestinal inflammation and/or IBD in an individual.

In some cases, the individual has been diagnosed or prognosed in accordance with the methods set out below.

In a further aspect, the invention provides a method of diagnosing or prognosing chronic intestinal inflammation and/or IBD in an individual, which method comprises measuring OSM and/or OSMR in the individual, and thereby diagnosing or prognosing the chronic intestinal inflammation and/or IBD in the individual.

The potential strength of a cytokine signalling pathway is determined by the relative abundance of both the ligand and the receptor. Therefore it is useful in some cases to measure both OSM and OSMR in the individual and determine the OSM index (OSMi) (the product of relative OSM and OSMR).

The inventors have shown that OSMR remains highly expressed during disease remission. Furthermore, OSM is suppressed following successful anti-TNFα therapy. This suggests that OSM signalling plays a role in disease recurrence. Therefore, in some cases the method of diagnosing or prognosing chronic intestinal inflammation and/or IBD is a method of predicting whether or not an individual in remission from chronic intestinal inflammation and/or IBD will have a recurrence.

In some cases, an elevated level of OSM, OSMR, and/or OSMi, as compared with a reference sample or reference level, indicates a positive diagnosis, a negative prognosis and/or that the individual will have a recurrence. In other cases, a reduced level of OSM, OSMR, and/or OSMi, as compared with a reference sample or reference level, indicates a negative diagnosis, a positive prognosis and/or that the individual will not have a recurrence.

In another aspect, the invention provides a method of treating or preventing chronic intestinal inflammation and/or IBD in an individual, the method comprising
  (a) diagnosing or prognosing chronic intestinal inflammation and/or IBD in the individual according to the method above; and
  (b) administering to the individual an agent useful in the treatment of chronic intestinal inflammation and/or IBD.

In some cases the agent is an antagonist of OSM and/or OSMR. The OSM and/or OSMR antagonist may be antagonist of OSM or OSMR activity or expression, such as an anti-OSM or anti-OSMR antibody, or an OSM or OSMR fusion protein.

The invention further provides:
  an agent for use in a method of treating or preventing chronic intestinal inflammation and/or IBD in an individual, in which chronic intestinal inflammation and/or IBD in the individual has been diagnosed or prognosed according to the method above;
  use of an agent in the manufacture of a medicament for use in a method of treating or preventing chronic intestinal inflammation and/or IBD in an individual, in which chronic intestinal inflammation and/or IBD in the individual has been diagnosed or prognosed according to the method above.
  products containing:
    means for determining the level of OSM and/or OSMR in an individual having or suspected of having or being at risk of developing chronic intestinal inflammation and/or IBD; and
    an agent for treatment of chronic intestinal inflammation and/or IBD.

The inventors have further shown that expression of OSM and OSMR in the intestinal mucosa is predictive of non-responsiveness to anti-TNFα therapy.

Accordingly, in a further aspect, the invention provides a method for predicting whether or not an individual will respond to an anti-TNFα therapy, which method comprises measuring OSM and/or OSMR in the individual, and thereby predicting whether or not the individual will respond to the anti-TNFα therapy. The anti-TNFα therapy may be an anti-TNFα antibody, such as infliximab.

In some cases, a reduced level of OSM, OSMR, and/or OSMi, as compared with a reference sample or reference level, indicates that the individual will respond to the anti-TNFα therapy. The method may then further comprise selecting or recommending anti-TNFα therapy for treatment of the individual. In some cases the anti-TNFα therapy is then administered to the individual. In some cases, the invention allows an anti-TNFα therapy to be identified as a suitable treatment for an individual who would not otherwise receive anti-TNFα therapy, for example as a first-line treatment. Anti-TNFα therapy, such as infliximab, is the "gold-standard" treatment for conditions such as IBD. In general, however, anti-TNFα therapy is not chosen as a first-line treatment because primary and secondary non-responsiveness is common, because of side-effects such as strong immunosuppression, and/or because the treatment is expensive. The method of the invention can be used to identify those individuals who will respond to and most benefit from an anti-TNFα therapy. Anti-TNFα therapy can then be selected or recommended for those individuals at an earlier stage in the treatment of their disease. Anti-TNFα therapy may be selected or recommended as a first-line treatment.

In some cases an elevated level of OSM, OSMR, and/or OSMi, as compared with a reference sample or reference level, indicates that the individual will not respond to the anti-TNFα therapy. The method may then further comprise selecting or recommending a therapeutic treatment other than anti-TNFα therapy for treatment of the individual. In some cases, the therapeutic treatment other than anti-TNFα therapy is then administered to the individual. In another aspect, the invention provides a method of treating or preventing a TNFα-mediated disease or condition in an individual, the method comprising administering a TNFα antagonist to the individual, and thereby treating or preventing the TNFα-mediated disease or condition, in which method the individual has been predicted to respond to the TNFα antagonist according the methods above.

The invention also provides:
  a TNFα antagonist for use in a method of treating or preventing a TNFα-mediated disease or condition in an individual, in which the individual has been predicted to respond to the TNFα antagonist according the method above;
  use of a TNFα antagonist in the manufacture of a medicament for use in a method of a treating or preventing TNFα-mediated disease or condition in an individual, in which the individual has been predicted to respond to the TNFα antagonist according the method above.

A further aspect provides an assay for measuring the level of OMS and/or OMSR in an individual having or suspected of having or being at risk of developing a TNFα-mediated disease, chronic intestinal inflammation and/or IBD, comprising contacting a biological sample from the individual with an agent that binds to OSM or OSMR, measuring complex formation between the agent and OSM or OSMR, optionally calculating the OSMi, comparing the measured value or the OSMi value with a reference value, and thereby predicting whether or not the individual having a TNFα-mediated disease will respond to an anti-TNFα therapy, or diagnosing or prognosing the chronic intestinal inflammation and/or IBD in the individual.

A further aspect provides a system comprising
  (a) a measuring module for quantifying the level of OSM and/or OSMR in a biological sample from an individual having a TNFα-mediated disease, chronic intestinal inflammation and/or IBD;
  (b) a storage module configured to store data output from the measuring module and reference and/or control data;
  (c) a computation module configured to compute the value of the data output from the measuring module and the reference or control data; and
  (d) an output module configured to display a diagnosis or prognosis for the individual having chronic intestinal inflammation and/or IBD, based on the value of the output data.

A further aspect of the invention provides a test kit for use in any of the diagnostic or prognostic methods of the invention, which test kit comprises means for determining the level of OSM and/or OSMR in the individual and instructions for use in the method.

In another aspect, the invention provides a method of determining the severity of chronic intestinal inflammation and/or IBD in an individual, which method comprises measuring OSM and/or OSMR in the individual, and thereby determining the severity of the chronic intestinal inflammation and/or IBD in the individual.

In another aspect, the invention provides a method of determining the likelihood that an individual with chronic intestinal inflammation and/or IBD will need surgery, which method comprises measuring OSM and/or OSMR in the individual, and thereby determining the likelihood that the individual will need surgery.

The invention will now be described in more detail, by way of example and not limitation, and by reference to the accompanying drawings. Many equivalent modifications and variations will be apparent, to those skilled in the art when given this disclosure. Accordingly, the exemplary embodiments of the invention set forth are considered to be illustrative and not limiting. Various changes to the described embodiments may be made without departing from the scope of the invention. All documents cited herein, whether supra or infra, are expressly incorporated by reference in their entirety.

The present invention includes the combination of the aspects and preferred features described except where such a combination is clearly impermissible or is stated to be expressly avoided. As used in this specification and the appended claims, the singular forms "a", "an", and "the" include plural referents unless the content clearly dictates otherwise. Thus, for example, reference to "an antagonist" includes two or more such antagonists.

Section headings are used herein are for convenience only and are not to be construed as limiting in any way.

Figure 1:
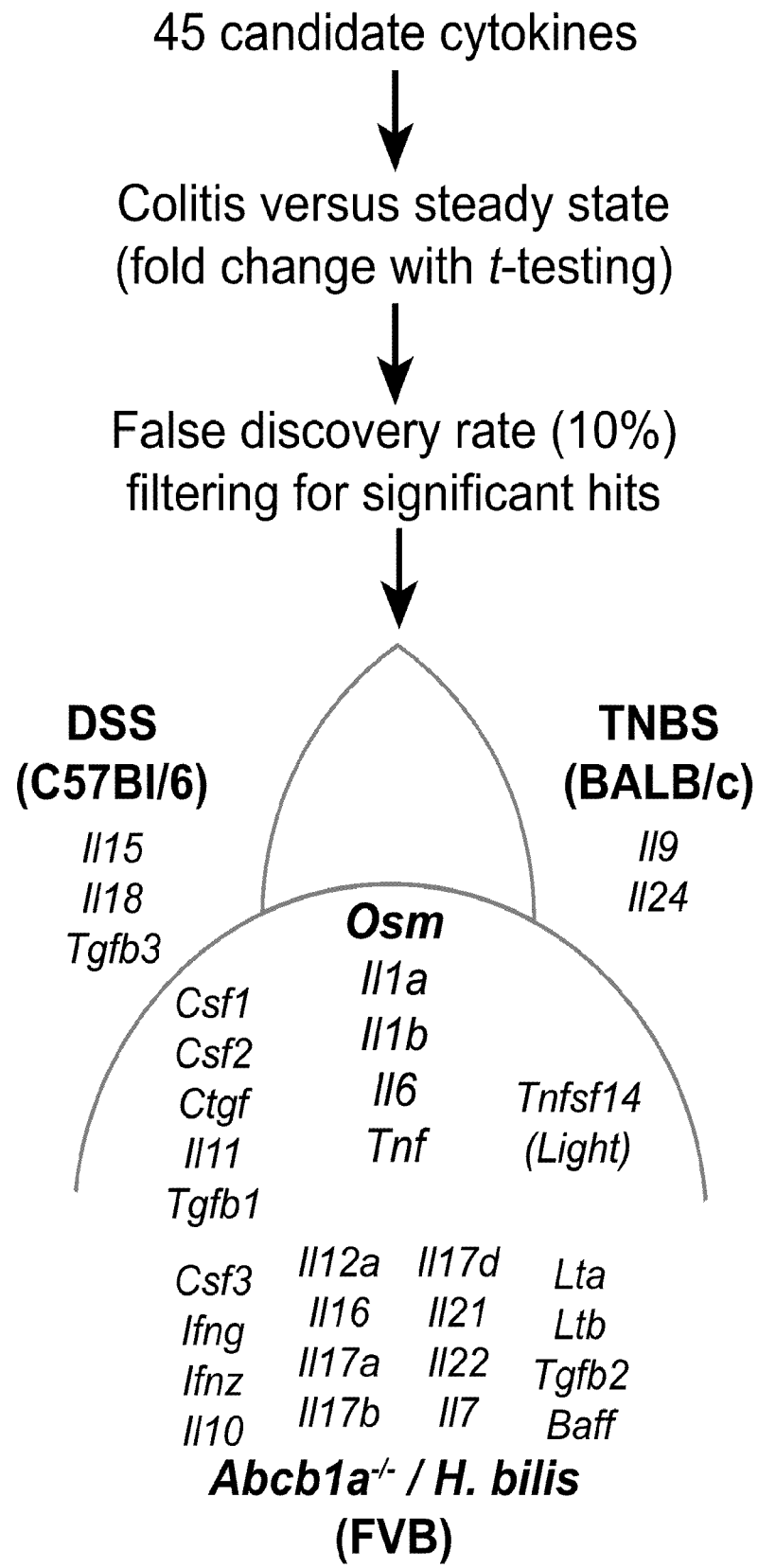
FIG. 1

Cytokines differentially expressed in whole colon tissue between healthy and colitic mice were identified in three different model systems: oral DSS (dextran sodium sulphate) administration in C57Bl/6 mice, rectally administered TNBS (trinitrobenzenesulfonic acid) in BALB/c mice, and oral *Helicobacter bilis* infection of FVB.129P2 mice with deletion of the Abcb1a gene. Whole transcriptome data are publicly available and are respectively derived from the following Gene Expression Omnibus (GEO) entries: GSE34553, GSE35609, and GSE72212. 45 candidate cytokines with available data in each dataset were chosen for analysis. Their expression levels were then assessed and those significantly altered during colitis (based on t-testing with false discovery rate correction) were identified. These are listed in the Venn diagram. Only Il1a, Il1b, Il6, Tnf, and Osm were significantly increased in the colons of colitic mice in all three model systems.

FIG. 2

Data generated using the Hh+αIL10R model, which combines immune dysregulation with commensal pathobiont (*Helicobacter hepaticus*) infection as described in Methods. (A) mRNA expression of Osm and Osmr in whole colon tissue from wild type C57Bl/6 mice (n=19 control and n=35 colitic mice, pooled from >3 experiments). (B) OSM production from 24 hour cultures of proximal colon explants (left) or caecal contents (right), quantified using an ELISA specific for mouse OSM. OSM concentration is normalized to the explant/caecal content mass (n=4 untreated and n=10 treated mice from one of three representative experiments). (C) Pearson correlation of Osm mRNA versus Il1b, Il6, and Tnf in whole colon tissue from mice at steady state and those with Hh+αIL10R colitis (n=63 from >3 pooled experiments). *p=0.01-0.05, p=0.001-0.01, *p=0.0001-0.001, ****p<0.0001, calculated using non-parametric Mann-Whitney tests or Kruskal-Wallis tests as appropriate.

FIG. 3

(A) Time-course kinetics of Osm and Osmr expression in whole colon tissue following induction of Hh+αIL10R colitis, with associated histological disease severity in (B) (n>4 mice per time-point). (C) Correlation of Osm and Osmr expression in whole colon tissue with histological severity bands (healthy, score=0 to 1; mild/moderate, score=>1 to 7; severe, score >7). n>15 mice per group pooled from three separate experiments. *p=0.01-0.05, p=0.001-0.01, *p=0.0001-0.001, ****p<0.0001, calculated using Kruskal-Wallis tests.

FIG. 4

(A-B) mRNA expression of OSM and OSMR assessed via quantitative real time polymerase chain reaction (qPCR) analysis of intestinal mucosal pinch biopsies or mucosa from intestinal resection samples from Oxford IBD patients or healthy controls. (A) OSM, OSMR, and OSM index (OSMi, product of relative OSM and OSMR) expression in biopsies from healthy controls (n=13), IBD patients with active disease (n=44), uninvolved intestinal locations of IBD patients with active disease (n=21), and IBD patients with no evidence of active inflammation (n=14). Disease activity/intestinal inflammation was determined by endoscopic assessment at the time of sample collection. (B) Analysis conducted as in panel (A), with samples categorized by histological grade of inflammation determined during routine clinical pathology assessment as follows: healthy controls (all quiescent) (n=13), quiescent IBD (n=27), mild to moderately active IBD (n=29), and severely active IBD (n=9). Significance determined using one-way ANOVA with Tukey's multiple comparisons tests. *p=0.01-0.05, p=0.001-0.01, *p=0.0001-0.001, ****p<0.0001.

FIG. 5

Pearson correlation of OSM expression with that of S100A8 and S100A9 (components of the clinically validated mucosal inflammation biomarker calprotectin). Data are derived from CD (GSE57945, n=220) and UC patients (GSE23597, n=112).

FIG. 6

(A) Expression of OSM and OSMR in healthy controls (n=13) versus active CD (n=19) or active UC (n=24) patients from the Oxford IBD cohort. Significance determined using one-way ANOVA with Tukey's multiple comparisons tests. (B) Comparison of ileal mucosal biopsies from treatment-naïve, paediatric ileal CD patients (n=162) with age-matched healthy controls (n=42). Data points reflect mean (+/−s.e.m.) fold IBD enrichment for 63 different cytokine genes (y-axis) versus statistical significance (x-axis) determined by t-tests with false discovery rate correction (Q=1%). Data derived from GEO entry GSE57945. *p=0.01-0.05, p=0.001-0.01, *p=0.0001-0.001, ****p<0.0001.

FIG. 7

Expression of OSM and OSMR in pouch biopsies collected from ileal pouch-anal anastomosis tissue. Data include UC patients with no pouchitis (inflammation of the pouch tissue), UC patients with active pouchitis, and familial adenomatous polyposis patients without pouchitis. *p=0.01-0.05, **p=0.001-0.01, determined using Kruskal- Wallis test with Dunn's multiple comparisons tests. Data derived from GEO entry GSE65270.

FIG. 8

(A-C) OSM and OSMR expression assessed by qPCR in intestinal mucosal biopsies from Oxford IBD patients. (A) Expression according to patient gender. (B) Expression according to patient age at diagnosis. (C) Expression according to duration of disease (ie, time in years from date of diagnosis to time of biopsy collection). Significance determined using t-tests (panel A) and one-way ANOVA (panels B and C).

FIG. 9

OSM and OSMR expression assessed by qPCR in intestinal mucosal biopsies from Oxford IBD patients. (A) Expression correlated with serum CRP (C-reactive protein) level and (B) peripheral blood leukocyte count at the time of sample collection. Significance determined using one-way ANOVA.

FIG. 10

OSM and OSMR expression assessed by qPCR in intestinal mucosal biopsies from Oxford IBD patients, comparing levels in patients categorized by treatment history. "Surgery" refers to mucosal biopsies collected directly from surgical resection specimens or biopsies collected endoscopically from patients who subsequently required surgical intervention. p=0.001-0.01, *p=0.0001-0.001, determined using t-tests.

FIG. 11

(A-D) Analysis of the publically available gene expression dataset GSE16879. (A) All patients in the cohort (top row) or CD patients alone (bottom row) were categorized according to relative OSM expression levels (grouped into tertiles) in intestinal biopsies prior to infliximab therapy. Each group was then assessed for frequency of clinical responsiveness to infliximab, with response rates indicated as pie charts. Response to treatment was defined as complete intestinal mucosal healing based on endoscopic and histological assessment. Significance determined using $\chi^2$ analysis. (B) Odds ratios and significance levels determined by Fisher's exact tests comparing infliximab response rates in patients with high expression (upper tertile) versus low expression (lower tertile) of the indicated genes in pre-therapeutic biopsies. High odds ratio values indicate reduced likelihood of clinical responsiveness to infliximab. *p=0.01-0.05, *p=0.0001-0.001, **p<0.0001.

FIG. 12

Analysis of the publically available gene expression dataset GSE16879. (A) Comparison of OSM index expression in pre-infliximab versus post-infliximab biopsies in UC patients, all of whom have high OSM index expression prior to infliximab therapy. OSM index expression is consistently reduced following infliximab therapy only in treatment-responsive patients. Significance determined using paired t-tests. (B) Mean fold changes (+/-95% CI) in intestinal expression of the indicated genes in post-versus pre-infliximab biopsies from infliximab-responsive UC patients. Significance determined using paired t-tests. ****p<0.0001.

FIG. 13

Receiver-operator characteristic (ROC) analysis of OSM index expression and probability of infliximab responsiveness in the GSE16879 dataset (showing the combined cohort and CD only), and two other studies of infliximab responsiveness in UC (GSE23597 and GSE12251). All plots were generated using gene expression data from pre-therapeutic biopsies.

FIG. 14

Association of OSM and OSMR expression in colonic biopsies at week 0, 8, and 30 following infliximab therapy (GEO dataset GSE23597). Patients are categorized into those with no clinical response at week 8 (black), those initially responsive at week 8 but refractory at week 30 (grey), and those with durable responses at weeks 8 and 30 (white). Significance determined using one-way ANOVA with Holm-Sidak's multiple comparisons test. *p=0.01-0.05, p=0.001-0.01, mp=0.0001-0.001, **p<0.0001.

FIG. 15

Hierarchical clustering analysis of OSM, OSMR, and cytokine mRNA expression in the GSE16879 dataset. The general gene cluster that includes OSM and OSMR is indicated with shading, and is notable for being enriched in cytokines that induce Th17 T helper cell differentiation, as well as effector cytokines of both Th17 and Th1 immune responses. Specimens from controls and infliximab refractory or responsive IBD patients are identified in the shading bar below the heat-map. All data are from pre-infliximab specimens.

FIG. 16

(A) Mean gene expression differences for representative Th17, Th1, and Th2 cytokines in OSM-high versus OSM-low specimens in GSE16879. Each dot represents the mean difference in UC, colonic CD, or ileal CD. The number of disease subtypes in which a differences is statistically significant (based on t-testing) is indicated by symbols (defined in associated legend). (B) Gene expression differences in OSM-high (upper half) versus OSM-low (lower half) IBD mucosal biopsies from the Oxford cohort. Data are represented as fold differences plotted against statistical significance, determined using t-tests with Holm-Sidak multiple comparison correction.

FIG. 17

(A) OSM secretion, determined by ELISA, in monocytes from 2 healthy human donors stimulated with the indicated microbial ligands at 100 ng/ml for 16 hours. (B) Representative experiment measuring OSM secretion by peripheral blood monocytes from 2 healthy donors in response to heat-killed bacteria (16 hour incubation). AIEC, adherent-invasive *Escherichia coli*.

FIG. 18

Figure 17:
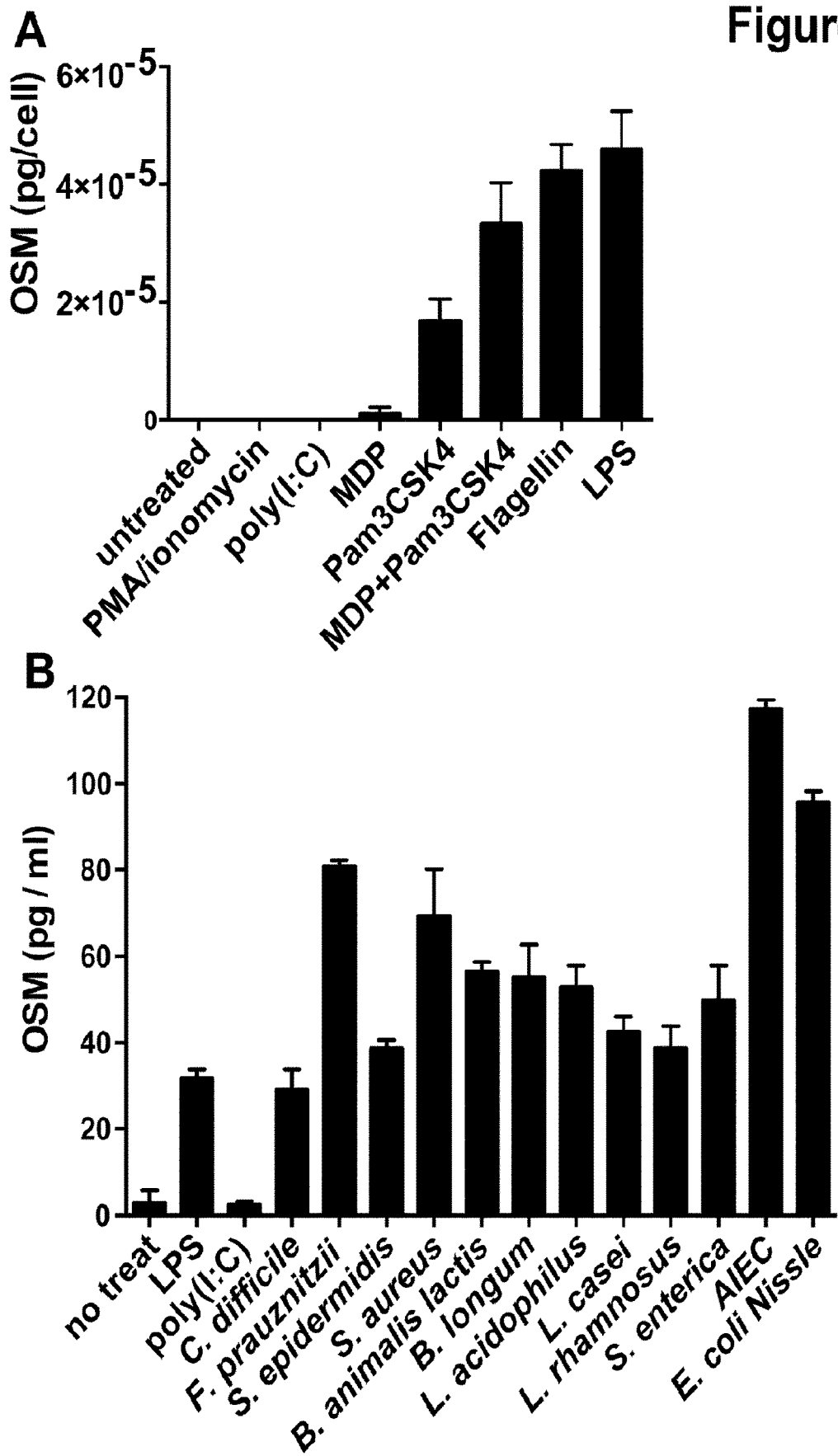

(A) Spearman correlation of OSM with other cytokines (assayed by qPCR) in bacteria-stimulated monocytes (as in FIG. 17). (B) OSM expression in human intestinal antigen presenting cells. Data are derived from a publically available gene expression dataset (GSE49066) from FACS-sorted antigen presenting cell subsets isolated from human intestinal tissue. Cells were sorted as lineage (CD3/19/20/56)⁻ HLA-DR$^{high}$ plus/minus the indicated surface markers. The CD14$^+$CD163$^{low}$ subset has been shown to possess superior Th17-inducing capacity relative to the other indicated APC subsets. (C) Hierarchical clustering of mean cytokine expression (assayed by qPCR) following bacterial stimulation in 2 sets of healthy donor monocytes. The cluster that includes OSM and OSMR is indicated with shading.

FIG. 19

OSM and OSMR expression was assessed in peripheral blood naïve and memory CD4$^+$ T cells directly ex vivo after stimulation with PMA (phorbol myristate acetate) and ionomycin. (A) Total CD4$^+$CD25$^-$ live T cells were FACS purified from 2 representative donors and stimulated for 8 hours. Gene expression of OSM and OSMR quantified by qPCR is depicted. (B) OSM protein was quantified by ELISA in supernatants after stimulation as described in (A). (C) Total PBMCs (peripheral blood mononuclear cells) were re-stimulated with PMA/ionomycin, and the frequencies of OSM+ cells within gated CD4+CD45RA+ and CD4+ CD45RO+ populations were analysed by intracellular cytokine staining using an antibody specific to human OSM.

FIG. 20

(A) Total CD45RO+ or CCR6+CD45RO+ memory CD4+ T cells were FACS purified and cultured with anti-CD3/CD28 beads under Th0, Th1, Th2 and/or Th17 conditions. The CCR6+ T cell population is considered to be enriched in Th17 cells. OSMR gene expression is shown after 7 days of culture. No expression was detectable in cells that did not receive anti-CD3/CD28 stimulation. (B-C) Naïve CD4+ CD45RA+ T cells from healthy human donors cultured with anti-CD3/CD28 under Th0, Th1, Th2 Th22, Th9, Treg, or Th17 polarizing conditions with or without OSM for 5 days. (B) Relative cell expansion in OSM treated conditions (20 ng/ml OSM) compared with OSM-free conditions. **p<0.01, paired t-test. (C) mRNA expression of key transcription factors (left) and effector cytokines (right) of T helper cells. Data shown represent relative expression in Th17 conditions with OSM versus Th17 conditions without OSM. *p=0.01-0.05, **p<0.01, one-sample t-test.

FIG. 21

Representative haematoxylin & eosin stained cross-sections of mid-colon sections from mice subjected to the Hh+αIL10R colitis protocol (see Methods). The two genotypes compared are wild type C57BL/6 mice and OSM knockout (Osm$^{-/-}$) littermates. Scale bars indicate 0.5 mm (top row) and 0.25 mm (bottom row). Arrows indicate salient features of severe inflammation, including submucosal oedema (double-headed), and crypt abscesses (single-headed).

FIG. 22

Comparison of colitis severity in wild type C57BL/6 mice and Osm$^{-/-}$ littermates subjected to the Hh+αIL10R colitis protocol. (A) Histopathology scores (determined as described in Methods) of mice pooled from two independent experiments. (B) Colitic mice from panel (A), with the overall histology score split into distinct components, each quantified on a severity scale of 0 to 3. (C) Expression of the pro-inflammatory cytokines Il6 and Il1b versus Il10 (anti-inflammatory) in whole colon tissue of mice (same animals as in panels A and B). *p=0.01-0.05, p=0.001-0.01, *p=0.0001-0.001, ****p<0.0001, determined using Mann-Whitney tests.

FIG. 23

A novel recombinant protein (O-RFP, adapted from Brolund et al, BMC *Biotechnology*, 2011) designed to neutralize mouse OSM was tested for OSM-neutralizing capacity in vitro relative to a commercially available goat polyclonal anti-OSM antibody. The assay involves treating mouse colonic fibroblasts cultured ex vivo with 10 ng/ml recombinant mouse OSM along with increasing molar ratios of neutralizing agent. Expression of OSM target genes was assessed after 2 hours; shown here are results for the STAT3 transcriptional target SOCS3. (A) Neutralization curve of the commercially available polyclonal antibody, with the calculated molar ratio required for 50% neutralization (12.1:1). (B) As in panel (A), using O-RFP, which requires only a 1.7:1 molar ratio for 50% neutralization.

O-RFP encodes murine proteins and is targeted against murine OSM. The construct is a modification of "mOSM-RFP" described in Brolund et al., BMC Biotechnology, 2011. Briefly, the recombinant receptor is a fusion protein comprised of, from N- to C-terminus (a) domains 1, 2, 3, and 4 of murine OSMR; (b) a flexible linker peptide; (c) domains 2 and 3 of murine gp130; (d) Fc tag (murine IgG2A). The construct was expressed in HEK-293 cells, purified using standard Protein G column purification, and confirmed to be endotoxin-free using testing services provided by Lonza. For in vivo experiments using this agent, IgG2A-Fc protein was prepared under identical conditions as a treatment control.

FIG. 24

Establishment of OSM as a relevant target for treating intestinal inflammation. (A) IL1B expression in mucosal explant cultures from human CD resections (n=5). Explants were treated for 24 hours with 20 μg/ml of anti-OSM neutralizing antibody (R&D Systems, clone 17022), matched isotype control antibody, or infliximab (anti-TNF). Data points represent mean (+/-s.e.m.) changes in IL1B in whole explant mRNA, normalized to untreated samples. These data suggest that the anti-inflammatory effect of OSM blockade in ex vivo human tissue may be comparable to that of infliximab (anti-TNF). Significance calculated using one-sample t-tests against a hypothetical mean of 1 prior to log transformation. (B) Overall histopathology scores of wild type C57BL/6 mice subjected to the Hh+αIL10R colitis protocol and treated starting at day 7 with anti-TNF monoclonal antibody, IgG-Fc control protein, or O-RFP as described in Methods. (C) Histopathology component scores of mice depicted in panel (B). (D) Representative colitis scores of mice treated as in panels (B/C), determined through endoscopic evaluation of live anaesthetized animals one day prior to sacrifice. This was conducted in accordance with standard protocols (Becker et al, *Nature Protocols*, 2007). *p=0.01-0.05, p=0.001-0.01, *p=0.0001-0.001, ****p<0.0001, determined using Mann-Whitney tests.

FIG. 25

Identification of key cellular sources of OSM and OSMR in mouse intestinal tissue. Viable FACS-purified cell populations were isolated from digested colon tissue of steady state (n=4) and colitic mice subjected to the Hh+αIL10R protocol (n=10). Markers used to identify and isolate cell populations are as follows: epithelial cells (CD45$^-$EpCAM$^+$); endothelial cells (CD45$^-$EpCAM$^-$CD31$^+$); gp38$^-$ stroma (CD45$^-$EpCAM$^-$CD31$^-$gp38$^-$); gp38$^+$ stroma (CD45$^-$EpCAM$^-$CD31$^-$gp38$^+$); granulocytes (CD45$^+$ FSC$^{int/hi}$SSC$^{hi}$); CD4$^+$ T cells (CD45$^+$CD3$^+$CD4$^+$); CD8$^+$ T cells (CD45$^+$CD3$^+$CD4$^-$); B cells (CD45$^+$CD3$^-$CD19$^+$); other mononuclear cells (CD45$^+$CD3$^-$CD19$^-$SSC$^{lo}$). Isolated cells were processed for RNA extraction and Osm and Osmr expression were assessed by qPCR. *p=0.01-0.05, **p=0.001-0.01, determined by t-tests.

FIG. 26

Flow cytometry analysis of mucosal cell populations from human intestinal resection specimens (n=10). (A) Representative OSMR surface expression by leukocytes (CD45$^+$), epithelial cells (CD45$^-$EpCAM$^+$), endothelial cells (CD45$^-$EpCAM$^-$CD31$^+$), gp38$^-$ICAM-1$^{lo}$ stroma (CD45$^-$EpCAM$^-$CD31$^-$gp38$^-$ICAM-1$^{lo}$) and gp38$^+$ICAM-1$^{hi}$ stroma (CD45$^-$EpCAM$^-$CD31$^-$gp38$^+$ICAM-1$^{hi}$). OSMR$^+$ frequencies are provided for all populations in panel (B). Significance determined using one-way ANOVA with Tukey's multiple comparisons tests.

FIG. 27

(A) Baseline expression of different cytokine receptor genes in primary human colonic stromal cells (CCD18Co) determined by qPCR. Receptors in the OSMR family are indicated. (B) Western blot analysis for activation of key signal transduction pathways following 20 minute stimulation of CCD18Co cells with recombinant OSM, IL-6, TNF, or IL-1β (10 ng/ml). β-actin is provided as a loading control.

FIG. 28

(A) Colitis was induced in wild type C57BL/6 mice according to the Hh+αIL10R protocol, and experimental groups received intraperitoneal injections of PBS or 0.04 mg/kg recombinant OSM (see Methods). Colon lamina propria cell populations were analysed by flow cytometry for evidence of stromal and endothelial cell activation. Specifically, CD45$^-$EpCAM$^-$gp38$^+$CD31$^-$ stromal cells and CD45$^-$EpCAM$^-$gp38$^-$CD31$^+$ endothelial cells were stained for surface ICAM-1 expression (a marker of inflammatory activation) and intracellular Ki-67 (a marker of proliferation). n=4 to 6 per group. (B) Flow cytometry analysis of ICAM-1 surface expression on colonic endothelial cells and gp38$^+$ stromal cells at steady state or after induction of Hh+αIL10R colitis in mice treated with control Fc protein or O-RFP (n=4 to 9 per group, representative of 2 independent experiments). Similar results were seen in colitic Osm$^{-/-}$ mice versus wild type littermates. *p=0.01-0.05, **p=0.001-0.01, determined using Mann-Whitney tests.

FIG. 29

Treatment of ex vivo cultured mouse colonic stromal cells, showing in (A) the impact of treatment with 10 ng/ml mouse OSM, 10 ng/ml TNF, or a combination of both on expression of representative genes after 2 hours (n=6-7 independent cultures per group). Significance determined by Kruskal-Wallis tests with Dunn's multiple comparisons tests. (B) Relative strength of response (measured by induction of Il6 expression) in mouse stromal cells elicited by three major members of the OSM family: OSM, IL-6, and LIF (all at 10 ng/ml; n=2-4 per group, pooled from 7 independent cultures). Significance determined by one-way ANOVA with Dunnett's multiple comparisons tests. *p=0.01-0.05, p=0.001-0.01, **p<0.0001.

FIG. 30

(A) Hierarchical clustering of human cytokine and chemokine gene expression in the publicly available transcriptome dataset GSE57945 (ileal CD and control mucosa). The gene set most robustly associated with OSM expression is highlighted in the lower panel and features a broad array of cytokines related to Th1/Th17 responses and chemokines that attract neutrophils (e.g. CXCL1), monocytes (e.g. CCL2/CCL7), and Th1 cells (CXCL9/10/11).

FIG. 31

(A) Gene expression kinetics in CCD18Co cells (human colonic stromal cells) stimulated with 10 ng/ml recombinant human OSM. Shown here are representative genes from different functional classes highlighted in FIG. 30: CCL2 (monocyte chemoattractant); CXCL9 (Th1 cell chemoattractant); CXCL1 (neutrophil chemoattractant); and ICAM1 (a critical cell adhesion molecule necessary for leukocyte tissue infiltration and retention). Data points represent mean (+/−s.e.m.) induction levels in triplicate cultures. (B) CCD18Co cells do not respond to LIF (the closest homologue of OSM), and OSM does not stimulate colonic stromal cells via LIFR (the alternative receptor subunit for OSM). Triplicate cultures were stimulated for 2 hours with 10 ng/ml LIF or 10 ng/ml OSM alone or in the presence of 15 μg/ml goat IgG control or 15 μg/ml anti-LIFR polyclonal goat IgG. Significance determined using one-way ANOVA with Tukey's multiple comparisons tests, ****p<0.0001.

FIG. 32

Treatment of triplicate CCD18Co cultures for 2 hours with 10 ng/ml OSM, IL-6, TNF, or combinations thereof, to assess the relative strength of stimulation from these cytokines and possible synergies. OSM and TNF exert both additive and synergistic effects depending on the response gene analysed.

FIG. 33

Treatment of triplicate CCD18Co cultures for 2 hours with 10 ng/ml OSM, IL-1β, or both OSM and IL-1β to assess functional synergy between these cytokines. OSM and IL-β exert both additive and synergistic effects depending on the response gene analysed. Significance determined using one-way ANOVA with Tukey's multiple comparisons tests, *p=0.0001-0.001, **p<0.0001.

FIG. 34

Figure 32:
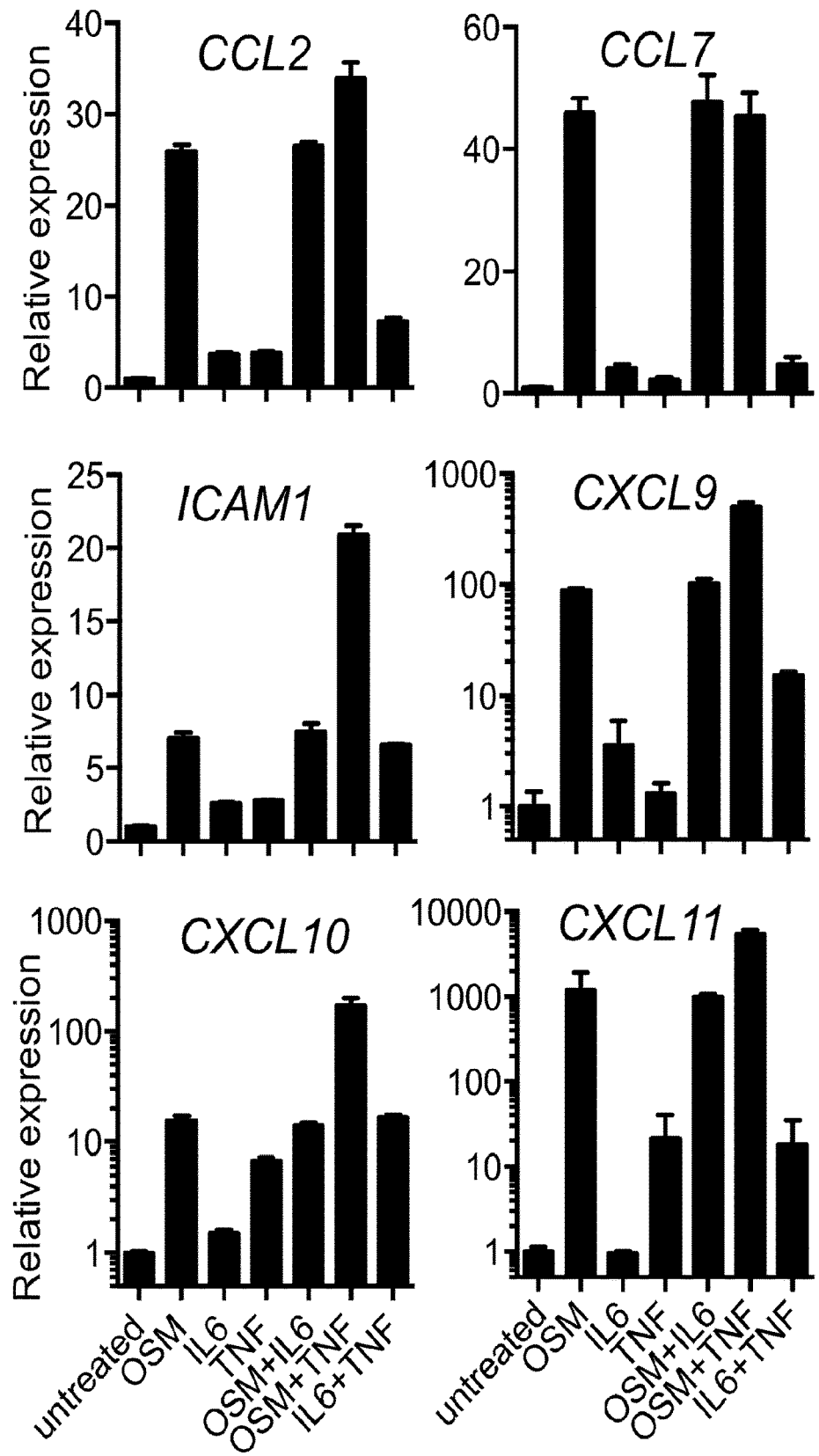

The same treatment and analysis strategy as described in FIG. 32 was deployed using primary ex vivo cultures of human colonic stromal cells isolated and expanded from non-inflamed surgical resection specimens (n=3-4 independent cultures per condition). Significance was determined using paired t-tests prior to control-normalization.

DETAILED DESCRIPTION

Therapy

The present invention relates in some aspects to methods of treatment with anti-TNFα therapy, an antagonist of TNFα, or an antagonist of OSM and/or OSMR. "Anti-TNFα therapy" is therapeutic treatment that is directed against or antagonizes TNFα, e.g. administration of an antagonist of TNFα. An antagonist of TNFα, OSM or OSMR is an agent that reduces TNFα, OSM or OSMR function. The antagonist may decrease the function of TNFα, OSM or OSMR by any therapeutically or prophylactically effective amount. For instance, the function may be decreased as appropriate by at least 10%, at least 20%, at least 30%, at least 40%, at least 50%, at least 60%, at least 70%, at least 80%, at least 90% or at least 95%. An antagonist may abolish the function of TNFα, OSM or OSMR (i.e. the function is decreased by 100%). TNFα, OSM or OSMR function may be measured by any suitable technique.

The antagonist may be an antagonist of TNFα, OSM or OSMR activity or an antagonist of TNFα, OSM or OSMR expression. The antagonist may decrease the amount of TNFα, OSM or OSMR, for instance by decreasing the production or expression of, or increasing the degradation of, TNFα, OSM or OSMR. The antagonist may decrease the release of soluble TNFα or OSM from cells. The antagonist may be capable of neutralising or removing soluble or extracellular TNFα or OSM and/or receptor bound TNFα or OSM or and/or transmembrane TNFα. The antagonist may inhibit or prevent effective binding of TNFα or OSM with one or more receptors. The antagonist may decrease the transcription of TNFα, OSM or OSMR. The antagonist may disrupt the DNA of TNFα, OSM or OSMR, for instance by site-specific mutagenesis using methods such as Zinc-finger nucleases. The antagonist may decrease the mRNA level of TNFα, OSM or OSMR or interfere with the processing of TNFα, OSM or OSMR mRNA, for instance by antisense RNA or RNA interference. The antagonist may increase protein degradation of TNFα, OSM or OSMR. The antagonist may increase the level of natural inhibitors of TNFα, OSM or OSMR. The antagonist may decrease the function of TNFα, OSM or OSMR by post-translational modification such as phosphorylation, ubiquitylation, sumoylation or the like.

The TNFα, OSM or OSMR antagonist may be specific to TNFα, OSM or OSMR, that is it acts predominantly or exclusively on TNFα, on OSM, or on OSMR, or acts on TNFα, on OSM, or on OSMR in preference to other molecules. For example, an anti-TNFα therapy preferably acts on TNFα, but not TNFβ, even though the two types of TNF can utilise the same receptors.

The antagonist of OSM and/or OSMR may inhibit Th17 helper T cells or Th17 CD4+ T cells, or development of the Th17 pathway. The antagonist may inhibit expansion of naïve CD4+ T cells activated under Th17 conditions. The antagonist may reduce or inhibit survival of naïve CD4+ T cells activated under Th17 conditions. The antagonist may increase expression of Th2 cytokines in Th17 cells.

Alternatively or in addition the antagonist of OSM and/or OSMR may inhibit aberrant activation of stroma and/or pathogenic fibrosis. The antagonist of OSM and/or OSMR may inhibit tissue vascularity, recruitment and retention of leukocytes, and/or local inflammatory processes. The antagonist of OSM and/or OSMR may inhibit epithelial proliferation. The antagonist of OSM and/or OSMR may inhibit the onset of dysplasia and neoplasia, a serious adverse event associated with chronic intestinal inflammation.

In some embodiments the antagonist is an antibody, a small molecule, a protein, a peptide, a polynucleotide, an oligonucleotide, an antisense molecule (such as an antisense RNA or morpholino), or an interfering RNA (such as a small interfering RNA (siRNA), a small hairpin RNA (shRNA) or a modified RNAi therapeutic prodrug such as a short, interfering ribonucleic neutral (siRNN)).

Antibodies

In some cases, the antagonist is an anti-TNFα, anti-OSM or anti-OSMR antibody, or an antigen-binding fragment thereof, i.e. an antibody or fragment thereof that specifically binds (as defined below) to TNFα, to OSM, or to OSMR and neutralizes or inhibits TNFα, OSM or OSMR activity. For example, the antagonist may be a nanobody (a single domain antibody; sdAbs), or an Fab' fragment, in isolation or complexed, or may be a modified Fc region, for example a Fcab, in isolation or combined with specific Fab domains against alternative targets as a bi-specific therapeutic agent (mAb$^2$). In some cases the antibody is a bispecific antibody, for example a bispecific antibody that targets both OSM and TNFα. Antibodies for use in accordance with the present invention are also further described below. The antagonist may be a synthetic antigen-binding scaffold or synthetic antibody, for example an Alphabody, Affibody, Affitin, Anticalin, Monobody or Adnectin specific to TNFα, OSM or OSMR.

Examples of anti-TNFα antibodies are infliximab, adalimumab, certolizumab or golimumab.

Infliximab and adalimumab are examples of antibodies capable of neutralising all forms (extracellular, transmembrane, and receptor-bound) of TNFα. Infliximab (sold under the brand name Remicade®) is a drug used to treat inflammatory and autoimmune diseases. Infliximab is a chimeric monoclonal antibody comprising murine binding VK and VH domains and human constant Fc domains. Infliximab neutralizes the biological activity of TNFα by binding with high affinity to the soluble (free floating in the blood) and transmembrane (located on the outer membranes of T cells and similar immune cells) forms of TNFα and inhibits or prevents the effective binding of TNFα with its receptors. Infliximab has high specificity for TNFα, and does not neutralize TNFβ, although TNFβ utilizes the same receptors as TNFα. Infliximab has been approved by the U.S. Food and Drug Administration for the treatment of, for example, psoriasis, pediatric Crohn's disease, ankylosing spondylitis, Crohn's disease, psoriatic arthritis, rheumatoid arthritis, and ulcerative colitis.

Adalimumab (sold under the brand name Humira®) also binds to TNFα, preventing it from activating TNF receptors. Adalimumab was constructed from a fully human monoclonal antibody, while infliximab is a mouse-human chimeric antibody. Adalimumab has been approved by the United States Food and Drug Administration (FDA) for the treatment of, for example, rheumatoid arthritis, psoriatic arthritis, alkylosing spondylitis, Crohn's disease, ulcerative colitis, psoriasis and juvenile idiopathic arthritis.

The anti-TNF therapy may comprise administration of a neutralising antibody to a TNF receptor. Typically, the neutralising antibody to the TNF receptor is a neutralising antibody to the TNFR1 receptor, for example, the human wild-type TNFR1 receptor. Examples of neutralising antibodies to the TNFR1 receptor include, but are not limited to, atrosab. Atrosab binds to amino acids 1 to 70 of human TNFR1 and selectively inhibits TNFR1-mediated signal transduction.

Examples of anti-OSM antibodies are described in US2014099315 (A1) and WO2012069433 (A2).

Examples of anti-OSMR antibodies are described in WO2014194274 (A2) and WO2013168829 (A1).

Non-Functional Forms and Fusion Proteins

The antagonist may be a reduced-functional form or non-functional form of TNFα, OSM or OSMR, which may compete with native (i.e. wild-type) TNFα, OSM or OSMR and thereby antagonize native TNFα, OSM or OSMR function. The function of the reduced-function form may be reduced/decreased by any amount. For instance, the function may be reduced/decreased by at least 10%, at least 30% at least 40%, at least 50%, at least 60%, at least 70%, at least 80%, at least 90% or at least 95% compared with wild-type TNFα, OSM or OSMR.

The mRNA sequence of human TNFα mRNA (GenBank Accession number NM_000594.3) is shown in SEQ ID NO. 1. The amino acid sequence is shown in SEQ ID NO: 2 (NP 000585.2). The mRNA sequence of human OSM mRNA (GenBank Accession number NM_020530.4) is shown in SEQ ID NO. 3. The amino acid sequence is shown in SEQ ID NO: 4 (NM_020530.4). The mRNA sequence of human OSMR mRNA (GenBank Accession number NM_003999.2) is shown in SEQ ID NO. 5. The amino acid sequence is shown in SEQ ID NO: 6 (NP 003990.1). The antagonist may be a reduced-functional variant or a non-functional variant of SEQ ID NO: 2, 4 or 6 or any isoform thereof. A reduced-functional variant is a protein that has an amino acid sequence which varies from that of SEQ ID NO: 2, 4 or 6 or any isoform thereof and has a reduced ability to function as TNFα, OSM or OSMR. A non-functional variant is a protein that has an amino acid sequence which varies from that of SEQ ID NO: 2, 4 or 6 or any isoform thereof and does not have the ability to function as TNFα, OSM or OSMR.

For instance, the non-functional variant of OSMR may have one or more mutations in the site that forms the dimeric receptor or interacts with the signal transduction pathways. The non-functional variant of OSMR may also be a truncated form that sequesters OSM. The non-functional variant may also be a soluble form of the receptor that sequesters OSM.

The ability of a variant to function as TNFα, OSM or OSMR can be assayed using any method known in the art. The comparative functional ability of reduced-function and non-functional variants is typically measured in comparison to the wild-type TNFα, OSM or OSMR, such as SEQ ID NO: 2, 4 or 6.

Over the entire length of the amino acid sequence of SEQ ID NO: 2, 4 or 6 or any isoform thereof, a variant may be at least 30%, at least 40%, at least 50%, at least 60%, at least 70%, at least 80%, at least 85%, at least 90%, at least 95%, at least 97% or at least 99% homologous to that sequence based on amino acid identity. There may be at least 80%, for example at least 85%, 90% or 95%, amino acid identity over a stretch of 200 or more, for example 300, 400, 500, 600, 700, 800, 1000, 1500 or 2000 or more, contiguous amino acids ("hard homology").

Standard methods in the art may be used to determine homology. For example the UWGCG Package provides the BESTFIT program which can be used to calculate homology, for example used on its default settings (Devereux et al (1984) Nucleic Acids Research 12, p 38'7-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http://www.ncbi.nlm.nih.gov/).

Variants may include fragments of SEQ ID NO: 2, 4 or 6 or any isoform thereof. Such fragments typically retain at least one functional domain, e.g. a binding domain, of SEQ ID NO: 2, 4 or 6 or any isoform thereof but are non-functional. Fragments may be at least 600, 700, 800 or 900 amino acids in length. One or more amino acids may be alternatively or additionally added to the polypeptides described above.

The antagonist may be a fusion protein or chimera comprising TNFα, OSM or OSMR (or a fragment of the TNFα, OSM or OSMR protein as described above) and a heterologous protein sequence. The fusion protein may act as a decoy binding partner for TNFα, OSM or OSMR and thereby inhibit TNFα, OSM or OSMR activity. In one embodiment, the antagonist is an OSM receptor fusion protein, for example comprising OSMR, gp30 and an immunoglobulin Fc region, such as the Fc region of IgG2A.

In one embodiment the chimera is a soluble TNFα or OSM receptor chimera. Examples of soluble TNF receptor chimeras include, but are not limited to, lenercept and etanercept. Etanercept binds to TNFα and decreases its role in diseases involving excess inflammation in humans and other animals, including autoimmune diseases such as ankylosing spondylitis, juvenile rheumatoid arthritis, psoriasis, psoriatic arthritis, rheumatoid arthritis, and, potentially, in a variety of other diseases mediated by excess TNFα.

Nucleic Acids

The antagonist may be a modified nucleic acid against TNFα, OSM or OSMR, for example an Aptamer. The antagonist may be a polynucleotide encoding an antagonist or non-functional variant of TNFα, OSM or OSMR. The antagonist or non-functional variant may be any of those discussed herein.

A polynucleotide, such as a nucleic acid, is a polymer comprising two or more nucleotides. The nucleotides can be naturally occurring or artificial. A nucleotide typically contains a nucleobase, a sugar and at least one linking group, such as a phosphate, 2'O-methyl, 2' methoxy-ethyl, phosphoramidate, methylphosphonate or phosphorothioate group. The nucleobase is typically heterocyclic. Nucleobases include, but are not limited to, purines and pyrimidines and more specifically adenine (A), guanine (G), thymine (T), uracil (U) and cytosine (C). The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), 5-methylcytidine monophosphate, 5-methylcytidine diphosphate, 5-methylcytidine triphosphate, 5-hydroxymethylcytidine monophosphate, 5-hydroxymethylcytidine diphosphate, 5-hydroxymethylcytidine triphosphate, cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP), 5-methyl-2'-deoxycytidine monophosphate, 5-methyl-2'-deoxycytidine diphosphate, 5-methyl-2'-deoxycytidine triphosphate, 5-hydroxymethyl-2'-deoxycytidine monophosphate, 5-hydroxymethyl-2'-deoxycytidine diphosphate and 5-hydroxymethyl-2'-deoxycytidine triphosphate. The nucleotides are preferably selected from AMP, TMP, GMP, UMP, dAMP, dTMP, dGMP or dCMP.

The nucleotides may contain additional modifications. In particular, suitable modified nucleotides include, but are not limited to, 2'amino pyrimidines (such as 2'-amino cytidine and 2'-amino uridine), 2'-hyrdroxyl purines (such as, 2'-fluoro pyrimidines (such as 2'-fluorocytidine and 2'fluoro uridine), hydroxyl pyrimidines (such as 5'-α-P-borano uridine), 2'-O-methyl nucleotides (such as 2'-O-methyl adenosine, 2'-O-methyl guanosine, 2'-O-methyl cytidine and 2'-O-methyl uridine), 4'-thio pyrimidines (such as 4'-thio uridine and 4'-thio cytidine) and nucleotides have modifications of the nucleobase (such as 5-pentynyl-2'-deoxy uridine, 5-(3-aminopropyl)-uridine and 1,6-diaminohexyl-N-5-carbamoylmethyl uridine).

One or more nucleotides in the polynucleotide can be oxidized or methylated. One or more nucleotides in the polynucleotide may be damaged. For instance, the polynucleotide may comprise a pyrimidine dimer. Such dimers are typically associated with damage by ultraviolet light.

The nucleotides in the polynucleotide may be attached to each other in any manner. The nucleotides may be linked by phosphate, 2'O-methyl, 2' methoxy-ethyl, phosphoramidate, methylphosphonate or phosphorothioate linkages. The nucleotides are typically attached by their sugar and phosphate groups as in nucleic acids. The nucleotides may be connected via their nucleobases as in pyrimidine dimers.

The polynucleotide can be a nucleic acid, such as deoxyribonucleic acid (DNA) or a ribonucleic acid (RNA). The polynucleotide may be any synthetic nucleic acid known in the art, such as peptide nucleic acid (PNA), glycerol nucleic acid (GNA), threose nucleic acid (TNA), locked nucleic acid (LNA), morpholino nucleic acid or other synthetic polymers with nucleotide side chains. The polynucleotide may be single stranded or double stranded.

Polynucleotide sequences may be derived and replicated using standard methods in the art, for example using PCR involving specific primers, a recombinant replicable (cloning) vector and suitable host cells. It is generally straightforward to generate polynucleotide sequences using such standard techniques.

Antisense and RNAi

Antagonists of TNFα, OSM or OSMR may reduce amounts of TNFα, OSM or OSMR present in the individual, for example by knocking down expression of TNFα, OSM or OSMR. Antisense and RNA interference (RNAi) technology for knocking down protein expression are well known in the art and standard methods can be employed to knock down expression of TNFα, OSM or OSMR.

Both antisense and siRNA technology interfere with mRNA. Antisense oligonucleotides interfere with mRNA by binding to (hybridising with) a section of the mRNA. The antisense oligonucleotide is therefore designed to be complementary to the mRNA (although the oligonucleotide does not have to be 100% complementary as discussed below). In other words, the antisense oligonucleotide may be a section of the cDNA. Again, the oligonucleotide sequence may not be 100% identical to the cDNA sequence. This is also discussed below.

RNAi involves the use of double-stranded RNA, such small interfering RNA (siRNA) or small hairpin RNA (shRNA), which can bind to the mRNA and inhibit protein expression.

Accordingly, the antagonist may comprise an oligonucleotide which specifically hybridises to a specific sequence in the mRNA for TNFα, OSM or OSMR, hereafter called the target sequence. Oligonucleotides are short nucleotide polymers which typically have 50 or fewer nucleotides, such 40 or fewer, 30 or fewer, 22 or fewer, 21 or fewer, 20 or fewer, 10 or fewer or 5 or fewer nucleotides. The oligonucleotide used in the invention is preferably 20 to 25 nucleotides in length, more preferably 21 or 22 nucleotides in length. The nucleotides can be naturally occurring or artificial. The nucleotides can be any of those described above.

The length of the target sequence typically corresponds to the length of the oligonucleotide. For instance, a 21 or 22 nucleotide oligonucleotide typically specifically hybridises to a 21 or 22 nucleotide target sequence. The target sequence may therefore be any of the lengths discussed above with reference to the length of the oligonucleotide. The target sequence is typically consecutive nucleotides within the target polynucleotide.

An oligonucleotide "specifically hybridises" to a target sequence when it hybridises with preferential or high affinity to the target sequence but does not substantially hybridise, does not hybridise or hybridises with only low affinity to other sequences.

An oligonucleotide "specifically hybridises" if it hybridises to the target sequence with a melting temperature ($T_m$) that is at least 2° C., such as at least 3° C., at least 4° C., at least 5° C., at least 6° C., at least 7° C., at least 8° C., at least 9° C. or at least 10° C., greater than its $T_m$ for other sequences. More preferably, the oligonucleotide hybridises to the target sequence with a $T_m$ that is at least 2° C., such as at least 3° C., at least 4° C., at least 5° C., at least 6° C., at least 7° C., at least 8° C., at least 9° C., at least 10° C., at least 20° C., at least 30° C. or at least 40° C., greater than its $T_m$ for other nucleic acids. Preferably, the portion hybridises to the target sequence with a $T_m$ that is at least 2° C., such as at least 3° C., at least 4° C., at least 5° C., at least 6° C., at least 7° C., at least 8° C., at least 9° C., at least 10° C., at least 20° C., at least 30° C. or at least 40° C., greater than its $T_m$ for a sequence which differs from the target sequence by one or more nucleotides, such as by 1, 2, 3, 4 or 5 or more nucleotides. The portion typically hybridises to the target sequence with a $T_m$ of at least 90° C., such as at least 92° C. or at least 95° C. $T_m$ can be measured experimentally using known techniques, including the use of DNA microarrays, or can be calculated using publicly available $T_m$ calculators, such as those available over the internet.

Conditions that permit the hybridisation are well-known in the art (for example, Sambrook et al., 2001, Molecular Cloning: a laboratory manual, 3rd edition, Cold Spring Harbour Laboratory Press; and Current Protocols in Molecular Biology, Chapter 2, Ausubel et al., Eds., Greene Publishing and Wiley-Interscience, New York (1995)). Hybridisation can be carried out under low stringency conditions, for example in the presence of a buffered solution of 30 to 35% formamide, 1 M NaCl and 1% SDS (sodium dodecyl sulfate) at 37° C. followed by a 20 wash in from 1× (0.1650 M Na$^+$) to 2× (0.33 M Na$^+$) SSC (standard sodium citrate) at 50° C. Hybridisation can be carried out under moderate stringency conditions, for example in the presence of a buffer solution of 40 to 45% formamide, 1 M NaCl, and 1% SDS at 37° C., followed by a wash in from 0.5× (0.0825 M Na$^+$) to 1× (0.1650 M Na$^+$) SSC at 55° C. Hybridisation can be carried out under high stringency conditions, for example in the presence of a buffered solution of 50% formamide, 1 M NaCl, 1% SDS at 37° C., followed by a wash in 0.1× (0.0165 M Na$^+$) SSC at 60° C.

The oligonucleotide may comprise a sequence which is substantially complementary to the target sequence. Typically, the oligonucleotides are 100% complementary. However, lower levels of complementarity may also be acceptable, such as 95%, 90%, 85% and even 80%. Complementarity below 100% is acceptable as long as the oligonucleotides specifically hybridise to the target sequence. An oligonucleotide may therefore have 1, 2, 3, 4, 5, 6, 7, 8, 9, 10 or zamore mismatches across a region of 5, 10, 15, 20, 21, 22, 30, 40 or 50 nucleotides.

The oligonucleotide may comprise any of the nucleotides discussed above, including the modified nucleotides. The oligonucleotide can be a nucleic acid, such as any of those discussed above. The oligonucleotide is preferably RNA. The oligonucleotide may be single stranded. The oligonucleotide may be double stranded. The oligonucleotide may comprise a hairpin. Oligonucleotides may be synthesised using standard techniques known in the art. Alternatively, oligonucleotides may be purchased.

In some cases the invention relates to a therapeutic treatment other than anti-TNFα therapy. In some cases the individual has an inflammatory disease or condition and the treatment is administration of an anti-inflammatory agent, for example a corticosteroid.

In some cases the individual has been diagnosed or prognosed in accordance with a method of the invention described below.

A "TNFα-mediated disease or condition" is a disease or condition that may be treated with or that is generally responsive to anti-TNFα therapy, i.e. in accordance with standard medical knowledge and/or practice for treatment of that particular disease or condition. A disease or condition is included in the term even if anti-TNFα therapy is generally not a common or first-line choice of treatment for the disease or condition, or if a high proportion of individuals having the disease or condition are known to be non-responsive, as long as the therapy is recognised as being an effective treatment in some patients. A TNFα-mediated disease or condition may be a disease or condition for which an anti-TNFα therapy or TNFα antagonist has regulatory approval for treatment of the disease or condition. The TNFα-mediated diseases or condition may be chronic intestinal inflammation, an autoimmune disease or an inflammatory disease. Examples of TNFα-mediated diseases or conditions are IBD, rheumatoid arthritis, juvenile idiopathic arthritis, ankylosing spondylitis, psoriatic arthritis, inflammatory skin conditions such as psoriasis (e.g. chronic severe plaque psoriasis), hidradenitis suppurativa and asthma. In some cases the TNFα-mediated disease or condition is psoriasis.

IBD refers to a group of inflammatory conditions of the colon and small intestine, sometimes also affecting other regions of the alimentary canal. Crohn's disease (including colonic and ileal Crohn's disease) and ulcerative colitis are the most common forms of IBD. Other forms include collagenous colitis, lymphocytic colitis, diversion colitis, Behçet's colitis, indeterminate colitis and acute severe colitis, including acute severe colitis induced by treatment with an immune checkpoint inhibitor biological therapy, e.g. for cancer. IBD is also a risk factor for the development of colorectal cancer. In some cases in accordance with the invention, the IBD is associated with bowel cancer. In some cases, the invention is for use in the treatment, diagnosis or prognosis of patients with severe ulcerative colitis, fulminant ulcerative colitis, or toxic megacolon, or those who fail conventional therapies (whether biological or non-biological), such as cyclosporine or infliximab, regardless of disease severity or manifestation.

Chronic intestinal inflammation is a spectrum of conditions afflicting the gastrointestinal tract that involve aberrant inflammatory responses and tissue damage with a relapsing-remitting course. Chronic intestinal inflammatory conditions include ulcerative colitis, Crohn's disease, indeterminate colitis, microscopic colitis (including collagenous and lymphocytic colitis), refractory coeliac disease (sprue), refractory eosinophilic gastroenteritis, eosinophilic esophagitis, chronic diverticular disease, and diversion colitis.

As shown in the Examples, OSM demonstrates synergy with TNFα and IL-1β when co-administered to human intestinal stromal cells. The antagonist of OSM and/or OSMR is preferably administered in combination with anti-TNFα therapy and/or an antagonist of IL-1β. Anti-TNFα therapy is discussed in more detail below. An antagonist of IL-1β may be any of the types of antagonists defined above for OSM and/or OSMR. Examples of approved antagonists of IL-1β include, but are not limited to, Anakinra (a recombinant IL-1 receptor antagonist), Rilonacept (soluble IL-1 receptor), and Canakinumab (anti-IL-1β mAb). Various other antagonists of IL-1β are in clinical development (see Dinarello et al, Nat Rev Drug Discovery, 2012). The method may comprise the use of a bispecific antibody, for example a bispecific antibody that targets both OSM or OSMR and IL-1β. Antibodies for use in accordance with the present invention are also further described below.

A combination means that the therapies may be administered simultaneously to the individual. The therapies may be administered separately or sequentially, in any order, to the individual as part of the same therapeutic regimen.

The invention also provides a product containing (a) an antagonist of OSM and/or OSMR and (b) anti-TNFα therapy and/or an antagonist of IL-1β for simultaneous, separate or sequential use in the treatment of chronic intestinal inflammation and/or IBD in an individual.

Diagnosis/Prognosis

The present invention relates in some aspects to a method of diagnosis or prognosis. Diagnosis includes determining whether or not an individual has a disease or condition and/or determining the severity of the disease or condition. Prognosis includes predicting whether or not an individual will develop a disease or condition, whether or not they will need treatment, the type of treatment the individual will need, whether or not they will respond to a treatment, whether or not and/or when they will suffer a disease episode, recurrence or relapse, and the severity or duration of a symptom or a disease episode, recurrence or relapse.

The method comprises measuring OSM and/or OSMR in an individual. In some cases both OSM and OSMR are measured and compared with reference OSM and OSMR levels or the OSM and OSMR levels of a reference sample to determine the OSM index (OSMi). The OSMi approximates the relative probability of active OSM-OSMR signalling in two or more directly comparable samples. The theoretical basis of the OSMi is as follows: based on published literature, the dominant receptor for OSM in human tissue is a heterodimer comprised of one gp130 chain and one OSMR chain. Gp130 is promiscuously and highly expressed in most human cell types and tissues; in contrast, OSMR expression is more tightly regulated and restricted to specific cell types and conditions. Therefore, OSMR is the limiting factor in the OSM receptor complex. OSM is similarly expressed in a controlled fashion; therefore, OSM and OSMR, which interact with a 1:1 stoichiometry, are the major limiting factors controlling OSM pathway activity. Relative OSM or OSMR expression in a tissue sample corresponds directly to the theoretical likelihood of active OSM signaling in that system. The OSMi is the product of the relative expression of OSM and OSMR in a sample within a dataset comprised of directly comparable samples.

An example of calculating the OSMi is as follows: We have two intestinal mucosal biopsies, one from a control patient, and one from an IBD patient. Using quantitative PCR, we find the mRNA levels of both OSM and OSMR in the samples relative to their corresponding housekeeping gene levels (e.g. RPLP0). These numbers are:
Control:
OSM—0.000058; OSMR—0.00083
IBD:
OSM—0.0022; OSMR—0.0073

The expression of OSM in the IBD specimen is 38-fold higher than that of the control sample. The expression of OSMR in the IBD specimen is 8.8-fold higher than that of the control sample. Therefore, if we designate the OSMi of the control sample as 1, the OSMi of the IBD specimen, rounded to two significant figures, =38×8.8=330.

To interpret the OSMi correctly, the input values (ie, relative OSM and OSMR expression) must be calculated relative to an appropriate reference value. This could take several forms depending on circumstances. In the example here, the logical comparator for the IBD specimen is the healthy control sample. In the data included in the examples below, the OSMi values are calculated using median values within the given dataset as the comparator. To calculate the OSMi in clinical scenarios a consistent reference sample may be used for each assay, such as the average OSM/OSMR expression in a panel of immortalized cell lines. The diagnostic or prognostic methods of the invention may be carried out in conjunction with one or more other assays or tests to refine the diagnosis or prognosis. For example, other markers may be included in the analysis. An example is serum C-reactive protein (CRP) for the diagnosis/prognosis of IBD. S100A8 is a biomarker of intestinal inflammation severity. Faecal calprotectin is commonly assayed in the clinic as an indicator of mucosal inflammation.

In some cases, the method of diagnosis or prognosis is a method for predicting whether or not an individual in remission from chronic intestinal inflammation and/or IBD will have a disease recurrence. Predicting whether or not the individual will have a recurrence includes determining the likelihood that the individual will have a recurrence, and/or predicting when they will have a recurrence. In some cases the individual is in remission following treatment with an anti-TNFα therapy, e.g. an anti-TNFα therapy as described herein.

In some cases, the method of prognosis is a method for predicting whether or not an individual will respond to an anti-TNFα therapy or an anti-OSM or anti-OSMR therapy, e.g. an antagonist of OSM and/or OSMR. Predicting whether or not an individual will respond includes determining the likelihood that the individual will respond, and/or predicting the extent to which the individual will respond, for example, the extent to which the individual's symptoms will be alleviated by the treatment.

Predicted responsiveness in an individual to anti-TNFα or anti-OSM/OSMR therapy means that the individual is expected to derive benefit, or a sufficient extent of benefit, from receiving the anti-TNFα or anti-OSM/OSMR therapy. Predicted non-responsiveness in an individual to anti-TNFα or anti-OSM/OSMR therapy means that the individual is not expected to derive benefit, or a sufficient extent of benefit, from receiving the anti-TNFα or anti-OSM/OSMR therapy. The method for predicting the response may be carried out before administration of anti-TNFα or anti-OSM/OSMR therapy. The prediction may then be taken into account when selecting or recommending a suitable treatment for the individual. Alternatively, the method may be carried out after treatment with anti-TNFα or anti-OSM/OSMR therapy and used to monitor and predict the individual's response to treatment. Typically the method is for predicting whether or not the individual will have a primary response to treatment with an anti-TNFα or anti-OSM/OSMR therapy, i.e. whether or not the individual will respond when first receiving the treatment. In some cases the method is for predicting secondary non-responsiveness, i.e. whether or not an individual who initially responds to treatment will later stop responding to treatment or will respond less well to the treatment.

According to the present invention, an increased level of OSM, OSMR, and/or OSMi in an individual, as compared with a reference sample or reference level, indicates a positive diagnosis relating to the presence of disease, for example that the individual has the relevant disease or condition or has more severe disease. An increased level of OSM, OSMR, and/or OSMi indicates a negative prognosis, that is a poor predicted outcome for the individual, for example that the individual will not respond to an anti-TNFα therapy, that an individual in remission from disease will have a recurrence or that the individual is at increased risk of developing the disease or condition. Conversely, a decreased level of OSM, OSMR, and/or OSMi indicates a negative diagnosis, for example that the individual does not have the relevant disease or condition or has less severe disease. A decreased level of OSM, OSMR, and/or OSMi indicates a positive prognosis, that is a good outcome for the patient, for example that the individual will respond to an anti-TNFα therapy or that an individual in remission from the disease will not have a recurrence or is not at increased risk of developing the disease or condition. For diagnosing whether or not an individual has the disease or condition, the reference sample or level typically represents a baseline level of OSM, OSMR or OSMi in an individual who does not have the relevant disease or condition, or who is suspected of having the disease or condition, but is subsequently confirmed to not have the disease or condition. A suitable reference sample or level can likewise be selected for the other methods of diagnosis or prognosis described herein.

The method of diagnosis or prognosis may include selecting or recommending a suitable treatment for the individual, i.e. based on the diagnosis or prognosis. The selected or recommended treatment may then be administered to the individual. For example, in some cases a reduced level of OSM, OSMR, and/or OSMi, as compared with a reference sample or reference level, indicates that the individual will respond to an anti-TNFα therapy. An anti-TNFα therapy may then be selected or recommended, and may then further be administered to the individual. In other cases, an elevated level of OSM, OSMR, and/or OSMi, as compared with a reference sample or reference level, indicates that the individual will not respond to an anti-TNFα therapy. The anti-TNFα therapy is then not administered to the individual. Further, a therapeutic treatment other than anti-TNFα therapy may be selected or recommended for treatment of the individual, and may then further be administered to the individual.

In all aspects of the invention, an individual having a disease or condition (e.g. IBD or chronic intestinal inflammation) includes an individual suspected of having the disease or condition and/or an individual at risk of developing the disease or condition. For example, the individual may not have been formally diagnosed but may be suspected of having the disease or condition because of the presence of one or more symptoms. Symptoms of IBD and/or chronic intestinal inflammation include abdominal or pelvic pain, cramps or muscle spasms, vomiting, diarrhea, rectal bleeding, weight loss, fever and anemia. The individual may be considered at risk of developing the disease or condition if they have one or more risk factors associated with the disease or condition and/or one or more predispositions which increase their susceptibility to the disease or condition. Risk factors for IBD and/or chronic intestinal inflammation include genetic predisposition and treatment with antibiotics.

The method preferably further comprises measuring TNFα and/or IL-1β in the individual, and thereby diagnosing or prognosing the chronic intestinal inflammation and/or IBD in the individual. The method preferably further comprises measuring both of TNFα and IL-1β. The TNFα and/or IL-1β may be measured in any of the ways discussed below for OSM and/or OSMR. The method preferably further comprises measuring TNFα and/or IL-1β in the individual, comparing the TNFα and/or IL-1β levels with reference TNFα and/or IL-1β levels or the TNFα and/or IL-1β levels of a reference sample, and determining the TNFα and/or IL-1β (TNFα i and/or IL-1βi). An elevated level of TNFα and/or IL-1β or TNFα i and/or IL-1βi, as compared with or calculated using a reference sample or reference level(s), typically indicates a positive diagnosis, a negative prognosis and/or that the individual will have a recurrence. A reduced level of TNFα and/or IL-1β or TNFαi and/or IL-1βi, as compared with or calculated using a reference sample or reference level(s), indicates a negative diagnosis, positive prognosis and/or that the individual will not have a recurrence.

The invention also provides a method of determining the severity of chronic intestinal inflammation and/or IBD in an individual. The invention also provides a method of determining the likelihood that an individual with chronic intestinal inflammation and/or IBD will need surgery. Both of these methods comprise measuring OSM and/or OSMR in the individual. The method typically comprises measuring OSM and OSMR in the individual, comparing the OSM and OSMR levels with reference OSM and OSMR levels or the OSM and OSMR levels of a reference sample, and determining the OSM index (OSMi). This can be achieved as discussed above. An elevated level of OSM, OSMR, and/or OSMi, as compared with or calculated using a reference sample or reference level(s), indicates that the disease is severe and/or that the individual is likely to need surgery. A reduced level of OSM, OSMR, and/or OSMi, as compared with or calculated using a reference sample or reference level(s), indicates that the disease is not severe and/or that the individual is not likely to need surgery.

Severity in this context refers to disease intensity as currently determined by standard endoscopic and histopathological assessment. This is related to treatment-refractory status in patients, whereby patients with greater disease severity are less likely to respond to pharmacological intervention and are therefore at higher risk for requiring surgical intervention. Surgery generally involves the removal of the affected regions of the GI tract and repair of associated complications, which is variable depending on the specific situation. For example, patients with Crohn's disease (CD) frequently require removal of discrete fibrotic regions of bowel, whereas some ulcerative colitis (UC) patients may require complete removal of the colon. Some patients will require additional surgical interventions such as correction of fistulae or construction of a stoma.

For determining severity of disease or the likelihood of surgery, the reference sample or level typically represents a baseline level of OSM, OSMR or OSMi in an individual who has a mild form of the disease or condition that does not require surgery. The reference sample or level may represent a baseline level of OSM, OSMR or OSMi in an individual who does not have the relevant disease or condition, or who is suspected of having the disease or condition, but is subsequently confirmed to not have the disease or condition.

The individual concerned is typically a mammal, for example a primate, rodent (including mice and rats), or other common laboratory, domestic or agricultural animal, including but not limited to rabbits, dogs, cats, horses, cows, sheep, goats, pigs etc. The individual may be a human.

Detection of OSM and/or OSMR

The level of OSM or OSMR is typically measured in vitro in a biological sample obtained from the individual. The sample may comprise a body fluid of the individual. A fluid sample may for example be a sample of blood, plasma, serum, stool, urine, cerebrospinal fluid or joint fluid.

Alternatively, the sample may comprise a tissue sample. Typically the tissue sample is from a part of the body that is affected by the disease or condition. For example, where the disease or condition is IBD or chronic intestinal inflammation, the tissue sample may be an intestinal biopsy (e.g. an intestinal mucosal biopsy) or a surgical resection sample.

The sample may be processed prior to being assayed, for example by centrifugation or extraction of DNA, RNA or protein. The sample may also be stored prior to assay, preferably below $-70°$ C.

Standard methods known in the art may be used to assay the level of OSM or OSMR. These methods typically involve using an agent that binds to or reacts with the relevant protein. The agent may be contacted with the sample from the individual and complex formation or a reaction between the agent and the relevant protein is measured. The agent typically binds specifically to the protein. The agent may be an antibody specific for the protein or an aptamer that binds to the protein. An antibody or other agent as described herein "specifically binds" to a protein when it binds with preferential or high affinity to that protein but does not substantially bind, does not bind or binds with only low affinity to other proteins. For example, an antibody or similar agent binds with preferential or high affinity if it binds with a Kd of $1 \times 10^{-7}$ M or less, more preferably $5 \times 10^{-8}$ M or less, more preferably $1 \times 10^{-8}$ M or less or more preferably $5 \times 10^{-9}$ M or less. An antibody binds with low affinity if it binds with a Kd of $1 \times 10^{-6}$ M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more. A variety of protocols for competitive binding or immunoradiometric assays to determine the specific binding capability of compounds, such as antibodies or antibody constructs and oligonucleotides are well known in the art (see for example Maddox et al, J. Exp. Med. 158, 1211-1226, 1993). Methods to assess OSM or OSMR level include antigen-capture dipstick assays and Enzyme-linked Immunosorbant Assay (ELISA). ELISA is typically carried out using the sandwich technique or the competitive technique, which are known to those in the art. The invention may also employ antibodies to OSM or OSMR in direct sensing techniques including but not limited to those based upon surface plasmon resonance, surface acoustic wave, quartz crystal microbalance, microcalorimetry or electrochemical impedance spectroscopy. A specific OSM mAb could be used in a a monoclonal antibody based immunochromatographic strip test for the detection of OSM levels in biological fluids. A modified oligonucleotide Aptamer could be used as part of a multiplex analyte detection system using the Somalogic Platform. OSMR expression levels could be determined by, for example, flow cytometry or by quantitative immunohistochemistry analysis on histological sections of patient intestinal tissue. Both OSM and OSMR mRNA levels can be accurately quantified by RNA analysis methods including qRT-PCR and next generation sequencing.

Antibodies

An antibody used in a method of the invention may either be a whole antibody or a fragment thereof which is capable of binding to the relevant protein. The antibody may be monoclonal or polyclonal. The antibody may be produced by any suitable method known in the art. For example, polyclonal antibodies may be obtained by immunising a mammal, typically a rabbit or a mouse, with HBP under suitable conditions and isolating antibody molecules from, for example, the serum of said mammal. Monoclonal antibodies may be obtained by hybridoma or recombinant methods.

Typically the antibody is a mammalian antibody, such as a primate, human, rodent (e.g. mouse or rat), rabbit, ovine, porcine, equine or camel antibody. The antibody may be a camelid antibody or shark antibody. The antibody may be a nanobody (a single domain antibody; sdAbs). The antibody can be any class or isotype of antibody, for example IgM, but is preferably IgG. The fragment of whole antibody that can be used in the method comprises an antigen binding site, e.g. Fab or F(ab)2 fragments or ScFV. The whole antibody or fragment may be an isolated antibody or fragment thereof or may be associated with or complexed with other moieties or may be in the form of a fusion protein. In one embodiment the antibody is a chimeric antibody comprising sequence from different natural antibodies, for example a humanised antibody.

Pharmaceutical Compositions and Modes of Administration

The agents for use in the methods of treatment described herein may be formulated in pharmaceutical compositions. These compositions may comprise, in addition to the therapeutically active ingredient(s), a pharmaceutically acceptable excipient, carrier, diluent, buffer, stabiliser or other materials well known to those skilled in the art. Such materials should be non-toxic and should not interfere with the efficacy of the active ingredient. The pharmaceutical carrier or diluent may be, for example, an isotonic solution.

The precise nature of the carrier or other material may depend on the route of administration, e.g. oral, intravenous, cutaneous or subcutaneous, nasal, intramuscular and intraperitoneal routes. Examples of suitable compositions and methods of administration are provided in Esseku and Adeyeye (2011) and Van den Mooter G. (2006). For example, solid oral forms may contain, together with the active substance, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, gum arabic, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film-coating processes.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the pharmaceutical composition is lyophilised, the lyophilised material may be reconstituted prior to administration, e.g. a suspension. Reconstitution is preferably effected in buffer.

Capsules, tablets and pills for oral administration to an individual may be provided with an enteric coating comprising, for example, Eudragit "S", Eudragit "L", cellulose acetate, cellulose acetate phthalate or hydroxypropylmethyl cellulose.

Liquid dispersions for oral administration may be syrups, emulsions or suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active substance, a pharmaceutically acceptable carrier, e.g. sterile water, olive oil, ethyl oleate, glycols, e.g. propylene glycol, and if desired, a suitable amount of lidocaine hydrochloride.

Solutions for intravenous administration or infusion may contain as carrier, for example, sterile water or preferably they may be in the form of sterile, aqueous, isotonic saline solutions.

For suppositories, traditional binders and carriers may include, for example, polyalkylene glycols or triglycerides; such suppositories may be formed from mixtures containing the active ingredient in the range of 0.5% to 10%, preferably 1% to 2%.

Polynucleotide or oligonucleotide inhibitors maybe naked nucleotide sequences or be in combination with cationic lipids, polymers or targeting systems. They may be delivered by any available technique. For example, the polynucleotide or oligonucleotide may be introduced by needle injection, preferably intradermally, subcutaneously or intramuscularly. Alternatively, the polynucleotide or oligonucleotide may be delivered directly across the skin using a delivery device such as particle-mediated gene delivery. The polynucleotide or oligonucleotide may be administered topically to the skin, or to mucosal surfaces for example by intranasal, oral, or intrarectal administration.

Uptake of polynucleotide or oligonucleotide constructs may be enhanced by several known transfection techniques, for example those including the use of transfection agents. Examples of these agents include cationic agents, for example, calcium phosphate and DEAE-Dextran and lipofectants, for example, lipofectam and transfectam. The dosage of the polynucleotide or oligonucleotide to be administered can be altered.

Administration is typically in a "prophylactically effective amount" or a "therapeutically effective amount" (as the case may be, although prophylaxis may be considered therapy), this being sufficient to show benefit to the individual, e.g. an effective amount to prevent or delay onset of the disease or condition, to ameliorate one or more symptoms, to induce or prolong remission, or to delay relapse or recurrence.

The dose may be determined according to various parameters, especially according to the substance used; the age, weight and condition of the individual to be treated; the route of administration; and the required regimen. A physician will be able to determine the required route of administration and dosage for any particular individual. A typical daily dose is from about 0.1 to 50 mg per kg of body weight dependent on the conditions mentioned above. The dose may be provided as a single dose or may be provided as multiple doses, for example taken at regular intervals, for example 2, 3 or 4 doses administered hourly. Typically polynucleotide or oligonucleotide inhibitors are administered in the range of 1 pg to 1 mg, preferably to 1 pg to 10 μg nucleic acid for particle mediated delivery and 10 μg to 1 mg for other routes.

Examples of the techniques and protocols mentioned above can be found in Remington's Pharmaceutical Sciences, 20th Edition, 2000, pub. Lippincott, Williams & Wilkins.

A composition may be administered alone or in combination with other therapeutic compositions or treatments, for example as adjunct therapy. The other therapeutic compositions or treatments may for example be one or more of those discussed herein, and may be administered either simultaneously or sequentially with the composition or treatment of the invention.

Standard current therapies for chronic intestinal inflammation include 5-ASA (aminosalicylic acid), various antibiotics, corticosteroids (e.g. budesonide, dexamethasone, hydrocortisone, methylprednisolone, prednisolone, and prednisone), azathioprine, 6-mercaptopurine, methotrexate, cyclosporine, anti-TNF antibodies (e.g. infliximab, adalimumab, certolizumab, golimumab), anti-α4β7 integrin antibodies (e.g. vedolizumab). Agents targeting OSM and/or OSMR or an antagonist of OSM and/or OSMR may be used in combination with any of the above agents. Clinical data suggest that IBD patients receiving combinations of anti-TNF therapy and non-biological therapies experience higher clinical response rates than those receiving anti-TNF or non-biologics alone (Colombel et al, 2010, *N Engl J Med;* 1383-95 and Panaccione et al, 2014, *Gastroenterology;* 392-400). Although data on combining distinct biological therapies are limited, there is scientific reason to believe that combining anti-OSM/OSMR agents with anti-TNF therapies may be beneficial, in that OSM and TNF can exert synergistic effects on target cells (e.g. OSM and TNF synergistically induce IL-6 expression by colonic stromal cells). Alternatively, a single-agent biological therapy with two or more target specificities (e.g. a bispecific antibody targeting both OSM and TNF) could be used. An OSM-targetted therapeutic could also be used in combination with other classes of therapeutics e.g. a small molecule or oligonucleotide therapeutic.

Kits

The invention further provides a diagnostic kit that comprises means (e.g. reagents) for measuring the OSM and/or OSMR level in an individual and instructions for use of the kit in accordance with methods of the invention. The kit may also comprise details regarding which individuals the method may be carried out upon. The kit typically contains one or more agents that specifically bind OSM or OSMR, e.g. an antibody. The kit may additionally comprise means for the measurement of other laboratory or clinical parameters. For example the kit may comprise means for measuring C-reactive protein (CRP).

The kit may additionally comprise one or more other reagents or instruments which enable the method to be carried out. Such reagents or instruments include one or more of the following: suitable buffer(s) (aqueous solutions), means to isolate OSM and/or OSMR from a sample, means to obtain a sample from the individual (such as a vessel or an instrument comprising a needle) or a support comprising wells on which quantitative reactions can be done.

Other Aspects

Accordingly, in a first aspect the invention provides a method of treating or preventing psoriasis or a Th17-mediated disease or condition in an individual, the method comprising administering to the individual an antagonist of OSM and/or OSMR, and thereby treating or preventing psoriasis or a Th17-mediated disease or condition in the individual.

The invention further provides:
an antagonist of OSM and/or OSMR for use in a method of treating or preventing psoriasis or a Th17-mediated disease or condition in an individual; and
use of an antagonist of OSM and/or OSMR in the manufacture of a medicament for use in a method of treating or preventing psoriasis or a Th17-mediated disease or condition in an individual.

In some cases, the individual has been diagnosed or prognosed in accordance with the methods set out below.

In a further aspect, the invention provides a method of diagnosing or prognosing psoriasis or a Th17-mediated disease or condition in an individual, which method comprises measuring OSM and/or OSMR in the individual, and thereby diagnosing or prognosing the psoriasis or a Th17-mediated disease or condition in the individual.

The potential strength of a cytokine signalling pathway is determined by the relative abundance of both the ligand and the receptor. Therefore it is useful in some cases to measure both OSM and OSMR in the individual and determine the OSM index (OSMi) (the product of relative OSM and OSMR).

The inventors have shown that OSMR remains highly expressed during disease remission. Furthermore, OSM is suppressed following successful anti-TNFα therapy. This suggests that OSM signalling plays a role in disease recurrence. Therefore, in some cases the method of diagnosing or prognosing psoriasis or a Th17-mediated disease or condition is a method of predicting whether or not an individual in remission from psoriasis or a Th17-mediated disease or condition will have a recurrence.

In some cases, an elevated level of OSM, OSMR, and/or OSMi, as compared with a reference sample or reference level, indicates a positive diagnosis, a negative prognosis and/or that the individual will have a recurrence. In other cases, a reduced level of OSM, OSMR, and/or OSMi, as compared with a reference sample or reference level, indicates a negative diagnosis, a positive prognosis and/or that the individual will not have a recurrence.

In another aspect, the invention provides a method of treating or preventing psoriasis or a Th17-mediated disease or condition in an individual, the method comprising
    (c) diagnosing or prognosing psoriasis or a Th17-mediated disease or condition in the individual according to the method above; and
    (d) administering to the individual an agent useful in the treatment of psoriasis or a Th17-mediated disease or condition.

In some cases the agent is an antagonist of OSM and/or OSMR. The OSM and/or OSMR antagonist may be antagonist of OSM or OSMR activity or expression, such as an anti-OSM or anti-OSMR antibody, or an OSM or OSMR fusion protein.

The invention further provides:
an agent for use in a method of treating or preventing psoriasis or a Th17-mediated disease or condition in an individual, in which psoriasis or a Th17-mediated disease or condition in the individual has been diagnosed or prognosed according to the method above;
use of an agent in the manufacture of a medicament for use in a method of treating or preventing psoriasis or a Th17-mediated disease or condition in an individual, in which psoriasis or a Th17-mediated disease or condition in the individual has been diagnosed or prognosed according to the method above.
products containing:
    means for determining the level of OSM and/or OSMR in an individual having or suspected of having or being at risk of developing psoriasis or a Th17-mediated disease or condition; and
    an agent for treatment of psoriasis or a Th17-mediated disease or condition.

A further aspect provides an assay for measuring the level of OMS and/or OMSR in an individual having or suspected of having or being at risk of developing psoriasis or a Th17-mediated disease or condition, comprising contacting a biological sample from the individual with an agent that binds to OSM or OSMR, measuring complex formation between the agent and OSM or OSMR, optionally calculating the OSMi, comparing the measured value or the OSMi value with a reference value, and thereby diagnosing or prognosing the psoriasis or a Th17-mediated disease or condition in the individual.

A further aspect provides a system comprising
(e) a measuring module for quantifying the level of OSM and/or OSMR in a biological sample from an individual having psoriasis or a Th17-mediated disease or condition;
(f) a storage module configured to store data output from the measuring module and reference and/or control data;
(g) a computation module configured to compute the value of the data output from the measuring module and the reference or control data; and
(h) an output module configured to display a diagnosis or prognosis for the individual having psoriasis or a Th17-mediated disease or condition, based on the value of the output data.

Any of the embodiments discussed above with reference to chronic intestinal inflammation and/or IBD and TNFα therapy equally apply to the embodiments concerning psoriasis or a Th17-mediated disease or condition. The Th17-mediated disease or condition may be, for example, IBD, psoriasis, atopic dermatitis, rheumatoid arthritis, juvenile idiopathic arthritis, ankylosing spondylitis, multiple sclerosis, type I diabetes, autoimmune uveitis, or cancer.

EXAMPLES

Methods
Gene Expression Analysis in Human Cohorts

All human tissue collection was performed under ethical approval from the Oxford Gastrointestinal Illness Biobank (reference number 11/YH/0020). We collected intestinal mucosal specimens from consenting IBD patients or healthy controls (undergoing endoscopy for non-IBD conditions) who were treated at the John Radcliffe Hospital (Oxford, UK), and extracted RNA for cDNA synthesis and quantitative real-time reverse transcription polymerase chain reaction (qPCR) analysis. As a complementary approach, we assessed data derived from publically available gene expression studies accessed via the Gene Expression Omnibus website (http://www.ncbi.nlm.nih.gov/geo/). Where such studies are utilized, the relevant accession numbers are referenced. In some figures we have included the OSM index (OSMi) as a measurable. This is calculated as the product of relative OSM and OSMR expression in a dataset. Because the potential strength of a cytokine signalling pathway is determined by the relative abundance of both the ligand and the receptor (and because OSM and OSMR interact with 1:1 stoichiometry), the relative OSMi corresponds to the theoretical signalling potential for this receptor-ligand pair.

Human Monocytes Analyses

Peripheral blood monocytes from healthy human donors were isolated using standard ficoll-gradient centrifugation followed by magnetic activated cell sorting (MACS) for CD14$^+$ cells. This routinely resulted in a monocyte purity of ≥95% based on flow cytometry analysis. Monocytes were cultured in RPMI medium with 10% fetal calf serum. Specific treatments are described in the figure captions. Monocyte responses were assessed either by qPCR (for mRNA) or by enzyme-linked immunosorbent assay (ELISA) for secreted products.

Human CD4$^+$ T Cell Analyses

Peripheral blood leukocytes were isolated from healthy human blood using ficoll-gradient centrifugation. Non-CD4$^+$ T cells were then depleted using MACS and the remaining fraction purified into naïve CD4$^+$CD45RA$^+$CD45RO$^-$CCR7$^+$ and memory CD4$^+$CD45RA$^-$CD45RO$^+$ T helper cell fractions using fluorescence activated cell sorting (FACS). T cells were activated and expanded for 5-7 days in the presence of different polarizing cytokines using anti-CD3/anti-CD28 beads. Polarizing cytokine combinations used are as follows: Th0 (neutral, no cytokines), Th1 (IFNγ+IL-12), Th2 (IL-4), Th9 (TGFβ+IL-4), Th22 (TNFα+IL-6), Treg (TGFβ), and Th17 (IL-1β+TGFβ+IL-6+IL-23). Neutralizing antibodies to IFNγ and/or IL-4 were used as appropriate for naïve T cell expansion. Base media for Th17 conditions was IMDM+5% human serum; media for all other conditions was RPMI+5% human serum. T cells were analyzed by qPCR or flow cytometry as specified in figure captions.

Mice

Wild type C57BL/6, C57BL/6.Rag$^{-/-}$, Il23r$^{gfp}$ reporter mice, and C57BL/6.Osm$^{-/-}$ mice were bred and maintained under specific pathogen free conditions in accredited animal facilities at the University of Oxford. C57BL/6.Osm$^{-/-}$ were originally acquired from the Jackson Laboratory (stock #022338). All procedures were conducted in accordance with the UK Scientific Procedures Act of 1986. Mice were negative for *Helicobacter* species and other known intestinal pathogens, were age and sex-matched, and more than 6 weeks old when first used. Both male and female mice were used in roughly equal proportions for all experiments. Mice were randomized to different treatments and all treatments were represented in a given cage of animals.

*Helicobacter hepaticus*/Anti-IL-10R Colitis Model

This model of T-cell dependent colitis involves oral infection of mice with the commensal bacterium *Helicobacter hepaticus* (Hh) in conjunction with antibody blockade of the IL-10 receptor (IL-10R), which impairs normal immune regulatory function resulting in colitis (Schiering and Krausgruber et al, *Nature*, 2014). Attenuation of TNF, IL-6, or IL-1β through pharmacological or genetic means has negligible therapeutic efficacy in this model (unpublished observations and FIG. 24), making this a model of highly treatment-refractory disease that is insensitive to anti-TNF therapy. Briefly, 6-12 week old C57BL/6 mice are given 1×10$^8$ colony forming units (cfu) of Hh in an oral gavage delivered by a 22 G curved blunted needle on days 0 and 1 of the experiment. IL-10R blocking antibody is administered as an intraperitoneal (IP) 1 mg injection on days 0 and 7. Mice are sacrificed at day 14, which corresponds to the peak of disease severity. In some experiments, mice were additionally administered recombinant murine OSM (daily IP injection of 1 μg (approximately equal to 0.04 mg/kg) from day 7 to 13) to assess whether additional OSM can influence the course of disease. This was compared with mice that received injections of PBS alone as a mock treatment. In other experiments, mice were treated with a recombinant murine OSM receptor fusion protein (O-RFP) incorporating OSMR, gp130, and the Fc region of murine IgG2A. O-RFP was administered as 150 μg IP injections every 2 days (equivalent to approximately 6 mg/kg) from day 7 to day 13. As a control treatment, mice were treated according to the same schedule with a molar equivalent dose of IgG2A-Fc manufactured under the same conditions as O-RFP. Finally, some mice were also treated with an anti-TNFα neutralizing antibody at a total weekly dose of 600 μg per animal. In our experience, this dose is sufficient to fully neutralize disease in other Hh-driven models of colitis.

Because the microflora can have profound effects on the outcome of preclinical studies and vary between animals and facilities, mice in all experiments were randomized to different treatment arms and co-housed prior to and for the duration of the experiment. In experiments involving Osm knockout mice, knockout animals were co-housed with and compared to wild type littermates. Finally, both therapeutic and Osm knockout experiments were replicated in two different animal housing facilities to demonstrate reproducibility between environments with distinct microbiota, animal diets, and enrichment.

Histological Assessment of Experimental Colitis

Mice were scored for disease severity as described (Izcue et al, *Immunity*, 2008). Briefly, formalin-fixed paraffin-embedded cross-sections of proximal, middle, and distal colon are stained with haematoxylin and eosin and graded on a scale of 0 to 3 for four parameters: epithelial hyperplasia and goblet cell depletion, leukocyte infiltration, area affected, and features of severe disease activity. Common severity features include crypt abscess formation, submucosal leukocyte infiltration, and interstitial oedema. Scores for each criterion are added to give an overall score of 0 to 12 per colon section. Data from the three colon regions are averaged to give an overall score for colon inflammation. Scoring was conducted in a blinded fashion and confirmed by an independent blinded observer. Interobserver Pearson correlation coefficients ranged from 0.90 to 0.95.

Intestinal Tissue Preparation and Cell Isolation

Mouse colons were washed with EDTA to remove epithelium and digested with collagenase VIII to liberate cell populations as described (Uhlig et al, *J. Immunol*, 2006). Tissue digests were separated by centrifugation on a 30%/40%/70% percoll gradient. Cells at the 30/40 interface were collected as the stroma/epithelium-enriched fraction, whilst cells at the 40/70 interface were collected as the lamina propria leukocyte enriched fraction and prepared for culture or flow cytometry analysis as indicated in figure legends. For ex vivo stromal culture, stromal fractions were plated and cultured as described (Schiering and Krausgruber et al, *Nature*, 2014).

Human intestinal biopsies or surgical resections were first washed for 15 minutes at room temperature with 1 mM DTT (dithiothreitol) solution to remove mucus. If necessary, surgical resection specimens were first prepared by separating mucosa from the underlying tissue and removing as much residual submucosal matter as possible. Resection tissues were then washed three times at room temperature for 30 minutes each in 0.75 mM EDTA (ethylenediaminetetraacetic acid) solution in (HBSS (Hank's balanced salt solution)) to remove the majority of epithelial cells. Remaining tissue was washed in HBSS to remove residual EDTA, cut into small pieces, and digested overnight in 0.1 mg/ml collagenase A solution in RPMI media+10% foetal calf serum. For biopsy preparation, tissues were digested immediately following DTT washing for 1 hour using 1 mg/ml collagenase A solution in a small volume. All solutions contained antibiotics as described (Owens et al, *Front Immunol*, 2013). Digested cells were filtered and separated on a percoll gradient as described (Geremia et al, *J Exp Med*, 2011). Stromal cells were plated and cultured as per previously described protocols (Owens et al, *Front Immunol*, 2013).

Statistics

All statistics were calculated using Graphpad Prism software. Parametric and non-parametric analyses, along with multiple testing corrections, were used as appropriate and are specified in figure legends, with $\alpha=0.05$ for all tests. Unless otherwise specified, all bar charts with error bars represent means±standard error.

Example 1 Identification of OSM as a Strong Disease Correlate in Preclinical Models of IBD The data shown in FIG. 1 demonstrate that only a small number of cytokine are consistently over-expressed in mechanistically distinct models of IBD, including TNF (the target of several successful IBD drugs, e.g. infliximab) and OSM. The DSS model involves oral gavage with dextran sodium sulphate, which irritates the intestinal mucosa and produces a pathology that resembles human UC. TNBS (2,4,6-trinitrobenzenesulfonic acid) is an alternative chemical colitis model in which the chemical is administered intra-rectally, resulting in pathology that resembles human CD. Finally, Abcb1a$^{-/-}$ mice develop spontaneous colitis that is accelerated upon intestinal colonization by *Helicobacter bilis*. The resulting colitis in this model bears features similar to both UC and CD (Maggio-Price et al, *Am J Path*, 2002). Importantly, each dataset used for this analysis was derived from animals with distinct genetic backgrounds and involved distinct analytical platforms. Therefore, OSM is reproducibly and strongly increased in colitis models with distinct mechanisms of action representing all major subtypes of human IBD, independently of animal strain or analytical strategy.

Example 2 OSM and OSMR Expression in Hh+αIL10R Colitis Model

Figure 2:
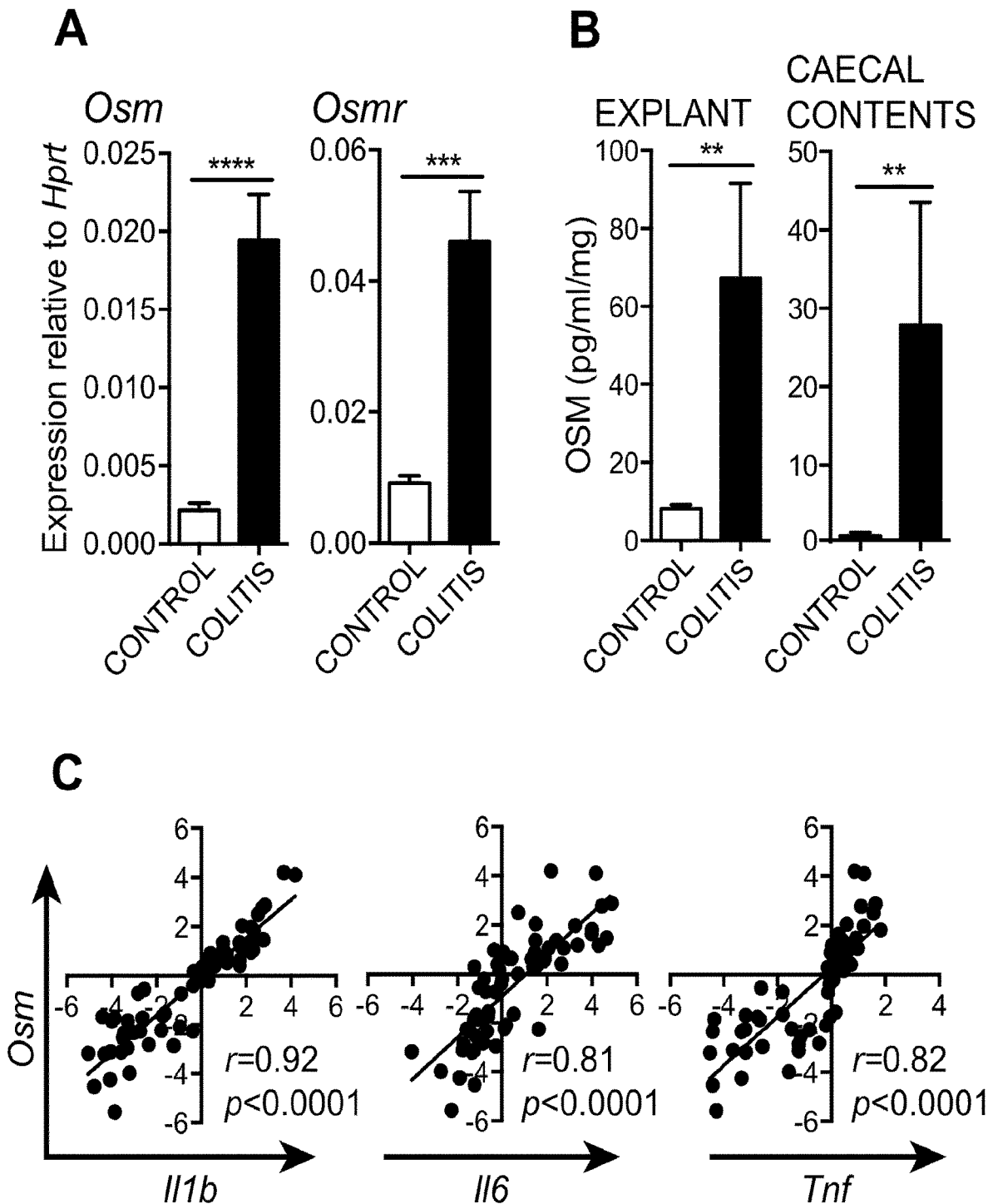
Figure 3:
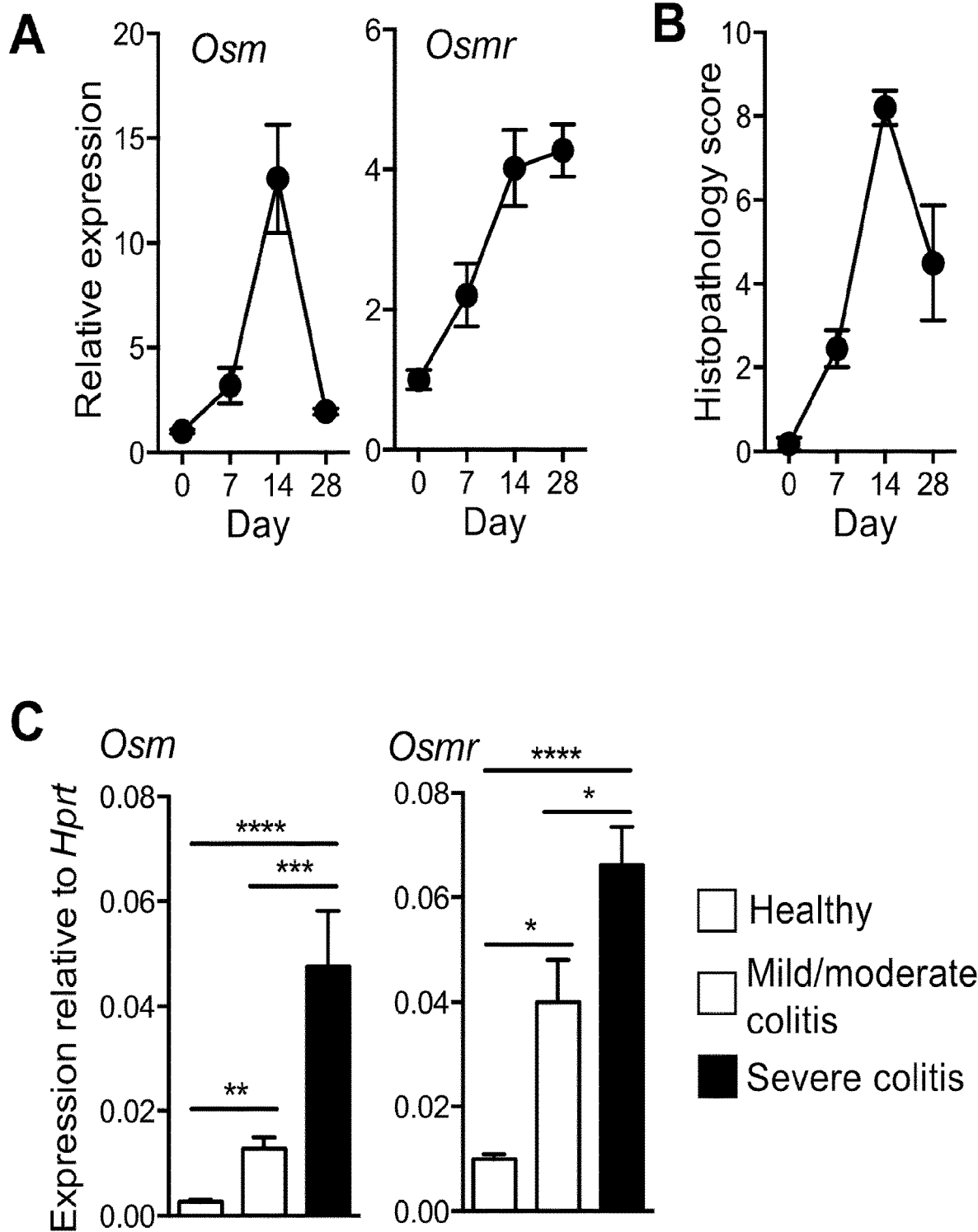

The data shown in FIG. 2 demonstrate that in the Hh+αIL10R model, expression of both OSM and its receptor OSMR are increased in colitic animals at both the mRNA and protein level (readily detectable in both tissue and faecal matter). OSM expression correlates closely with that of IL-10, IL-6, and TNF, suggesting that OSM is a previously unrecognized member of a core group of co-regulated inflammatory cytokines. Data shown in FIG. 3 demonstrate that induction of OSM and OSMR expression in this model correlates with the kinetics of pathology progression, as well as overall pathology severity. Expression of OSM and OSMR is therefore tightly correlated with disease in this setting.

Example 3 OSM and OSMR Expression in Human IBD Intestinal Mucosa

Figure 4:
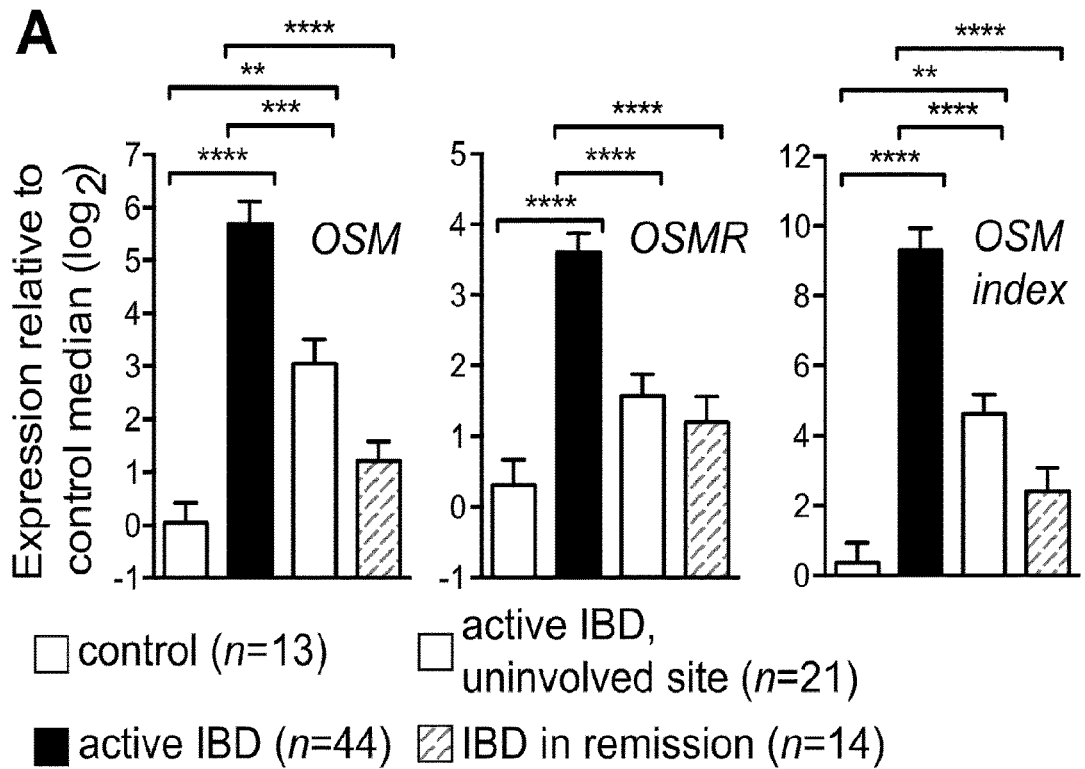
Figure 4:
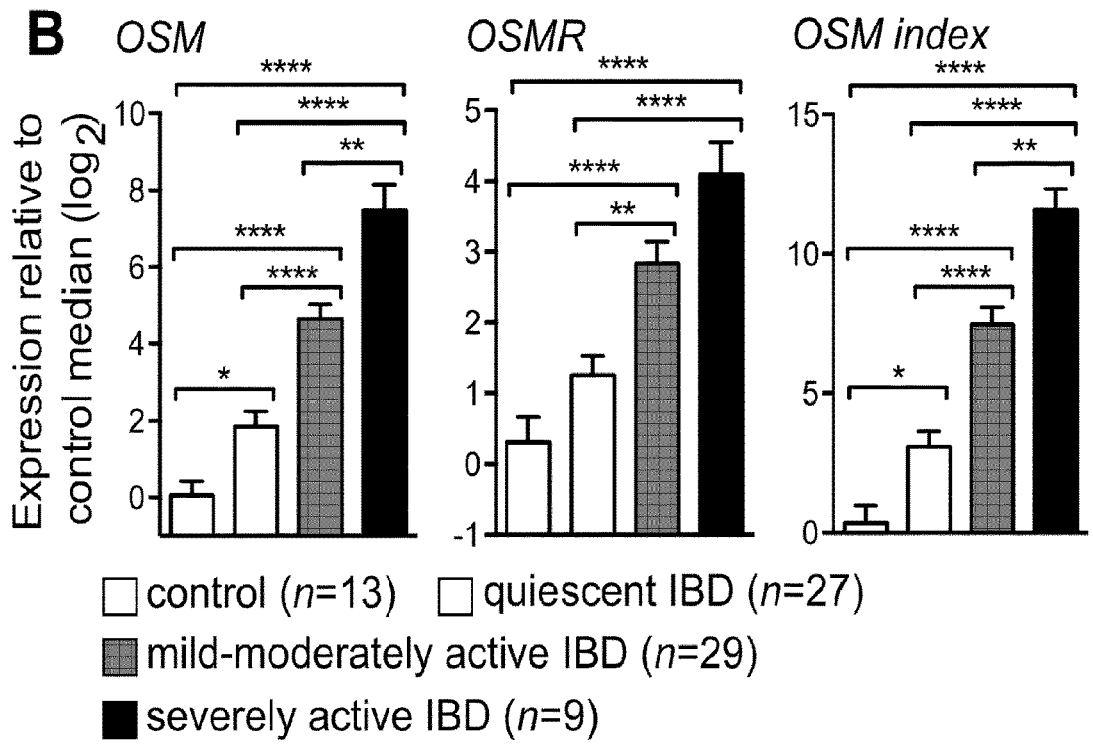

The data shown in FIG. 4 demonstrate that OSM, OSMR, and the OSM index are highly enriched in the intestinal mucosa during active disease in the majority of IBD patients. This is clear based on both endoscopic and histological measures of disease activity. Notably, OSM and OSMR expression increase in direct correlation with increasing histological disease severity.

Figure 5:
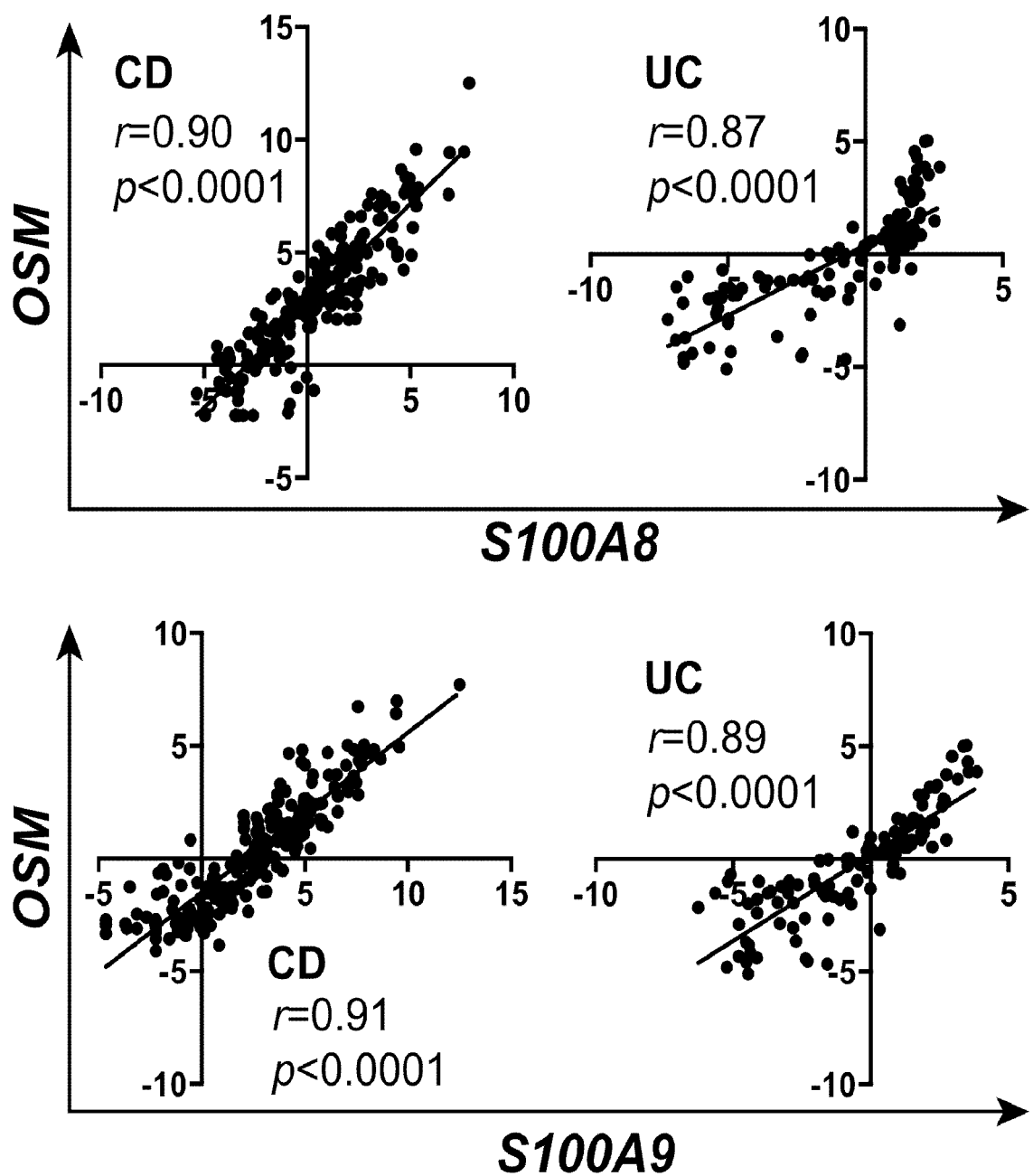
Figure 6:
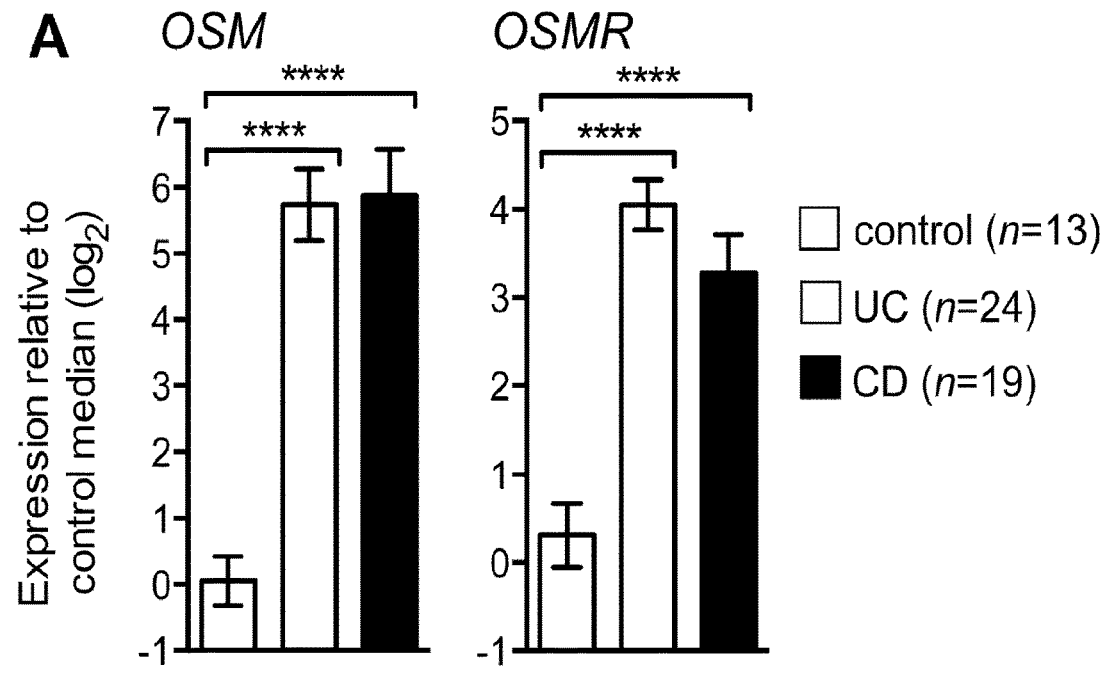
Figure 6:
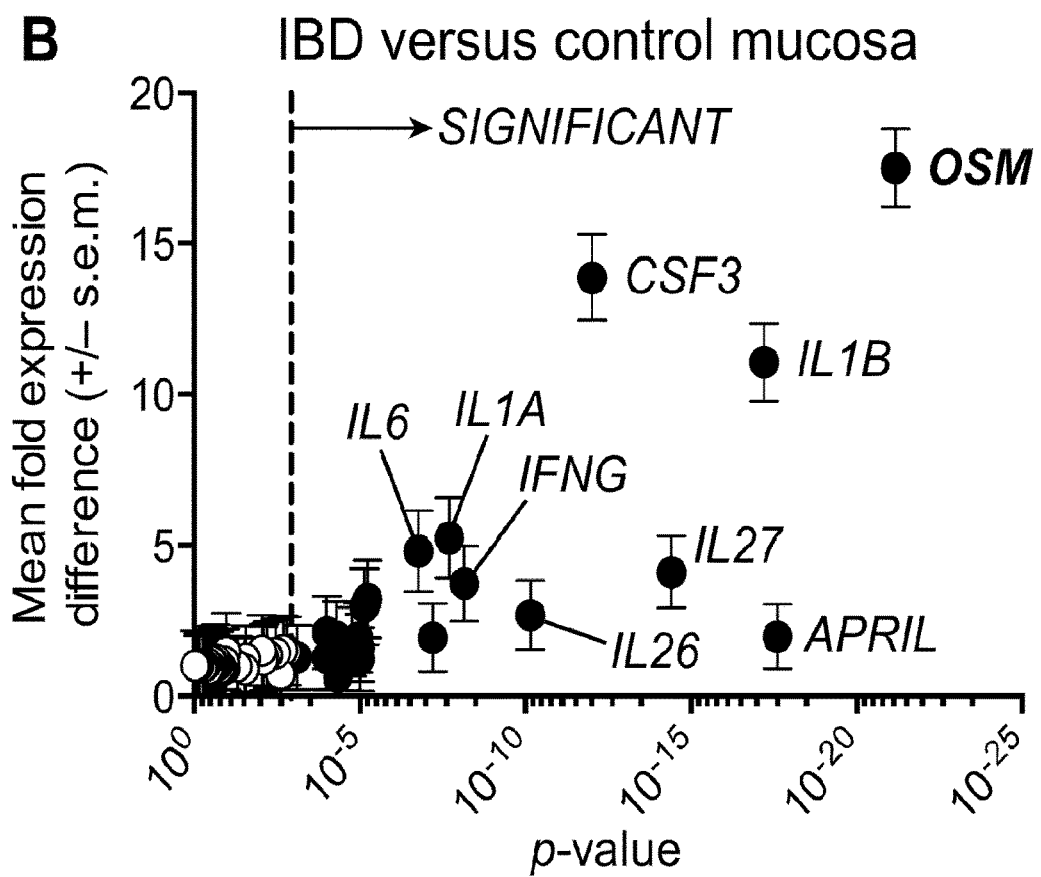
Figure 7:
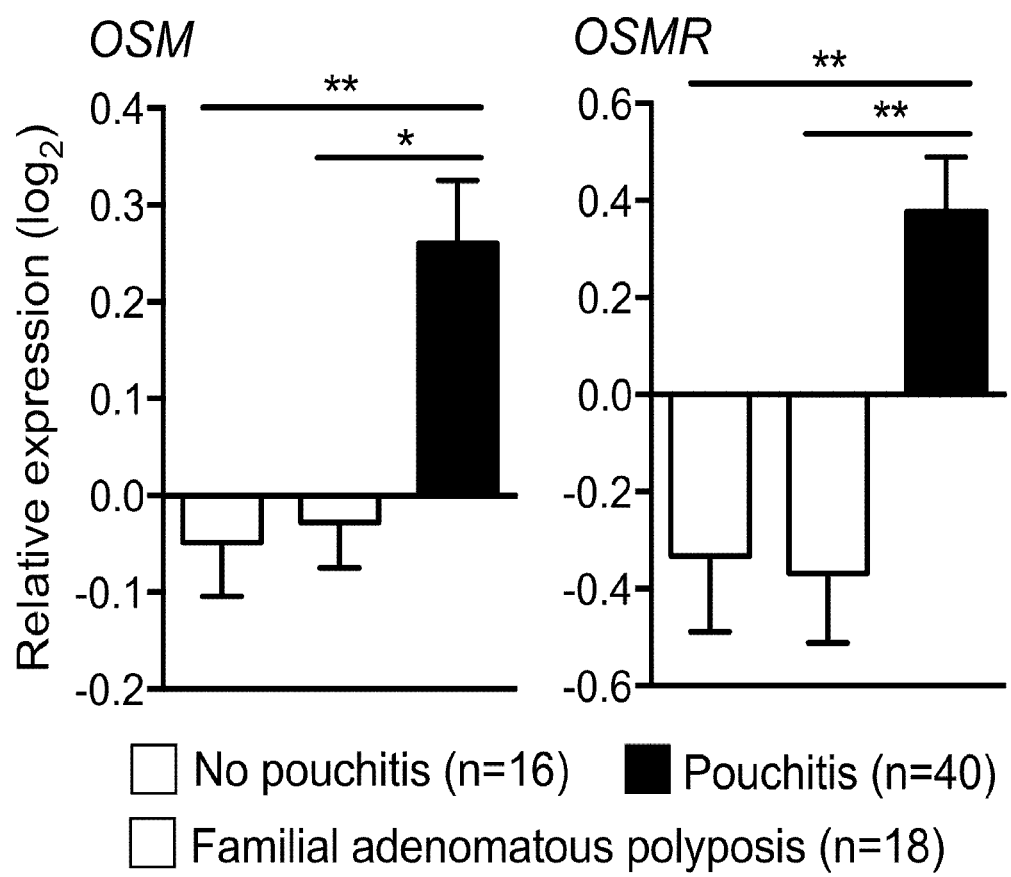

FIG. 5 demonstrates that OSM is closely correlated with expression of known biomarkers of intestinal mucosal inflammation, S100A8 and S100A9, which together form the faecal protein biomarker calprotectin. FIG. 6 demonstrates that OSM and OSMR expression is equivalent in both UC and CD patients. Furthermore, OSM is perhaps the most consistently over-expressed member of classical cytokine families in IBD. Finally, OSM and OSMR are both enriched in the pouch tissue of patients with inflamed ileal pouch-anal anastomoses, for whom pouch inflammation is a common and problematic complication of surgery (FIG. 7).

Example 4 OSM and OSMR Expression in Independent IBD Cohorts

Table 1 summarizes the fold changes and significance of OSM and OSMR expression in intestinal mucosal biopsies from IBD patients versus healthy controls. In total, Table 1 displays data from 5 geographically distinct patient groups spanning UC, CD, and both adult and paediatric IBD. The total sample sizes are 118 healthy controls and 370 IBD patients. These data demonstrate that OSM and OSMR are over-expressed in IBD patient intestinal mucosa with a high degree of reproducibility in distinct patients populations.

OSMR, and the OSM index may thus be useful biomarkers for predicting therapeutic outcome with current regimens, particularly anti-TNFα therapy. Furthermore, OSM may serve as a therapeutic target for anti-TNF refractory patients.

TABLE 1

Mean fold changes in OSM and OSMR expression in active IBD intestinal mucosa versus healthy controls in independent cohorts.

| Country | Data type* | Disease | Control n | IBD n | OSM Mean Δ (95% CI) | p-value | OSMR Mean Δ (95% CI) | p-value |
|---|---|---|---|---|---|---|---|---|
| England | RT-qPCR | Ulcerative colitis[1] | 13 | 24 | 71.2 (19.0-266) | $2.1 \times 10^{-8}$ | 7.99 (3.33-19.1) | $2.3 \times 10^{-9}$ |
|  | RT-qPCR | Crohn's[1] | 13 | 19 | 37.7 (8.29-171) | $2.9 \times 10^{-7}$ | 4.37 (1.70-11.2) | $3.0 \times 10^{-5}$ |
| North America[†] | RNA-Seq | Crohn's (ileal)[2] | 42 | 162 | 17.5 (10.4-29.5) | $6.6 \times 10^{-22}$ | 1.61 (1.31-1.98) | $1.0 \times 10^{-5}$ |
| Belgium | Microarray[‡] | Ulcerative colitis[3] | 11 | 74 | 2.02 (1.51-3.36) | <0.0001 | 7.31 (5.61-10.8) | <0.0001 |
|  | Microarray | Ulcerative colitis[4] | 6 | 24 | 9.89 (3.68-26.6) | $5.6 \times 10^{-5}$ | 6.15 (3.85-9.82) | $1.1 \times 10^{-8}$ |
|  | Microarray | Crohn's (colonic)[4] | 6 | 19 | 3.05 (0.656-14.2) | $1.5 \times 10^{-1}$ | 3.75 (2.09-6.75) | $1.0 \times 10^{-4}$ |
|  | Microarray | Crohn's (ileal)[4] | 6 | 18 | 14.6 (3.68-57.9) | $6.0 \times 10^{-4}$ | 1.91 (1.19-3.07) | $9.8 \times 10^{-3}$ |
| Hungary | Microarray | Mixed IBD[5] | 8 | 15 | 6.13 (2.82-13.3) | $8.6 \times 10^{-5}$ | 2.43 (1.77-3.33) | $8.8 \times 10^{-6}$ |
| Spain | Microarray[‡] | Ulcerative colitis[6] | 13 | 15 | 1.38 (1.03-1.68) | 0.0002 | 8.44 (5.49-16.1) | <0.0001 |
|  |  | Total n | 118 | 370 |  |  |  |  |

*All data derived from intestinal mucosa
[†]RISK: inception cohort representing paediatric patients from 28 sites across North America
[‡]Data not normally distributed. Results depict differences in medians and significance values derived from non-parametric Mann-Whitney U-tests
[1]West et al, unpublished data. 2015.
[2]Haberman et al, *J Clin Invest* 124: 3617-33. 2014.
[3]Vanhove et al, *Inflamm Bowel Dis* 21: 2673-82. 2015.
[4]Arijs et al, *PLoS ONE* 4: e7984. 2009.
[5]Galamb et al, *Dis Markers* 25: 1-16. 2008.
[6]Planell et al, *Gut* 62: 967-76. 2013.

Example 5 Correlation of OSM and OSMR with Clinical Features in IBD

Figure 8:
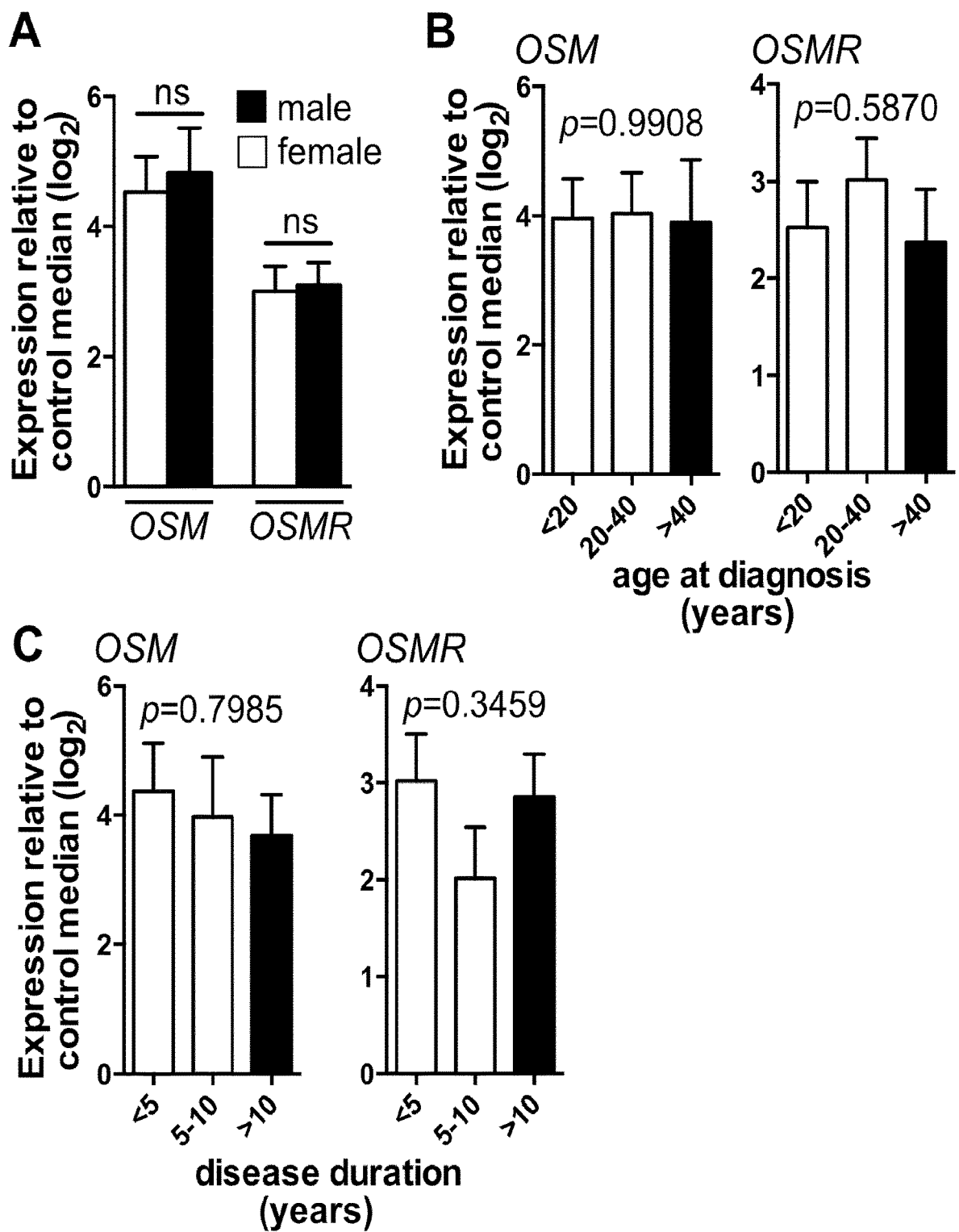
Figure 9:
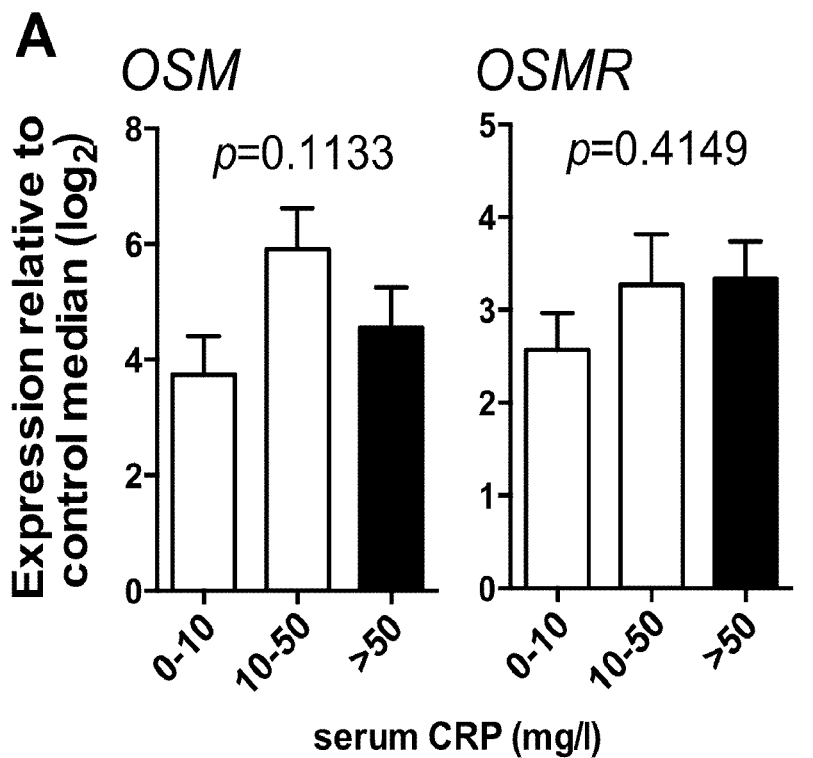
Figure 9:
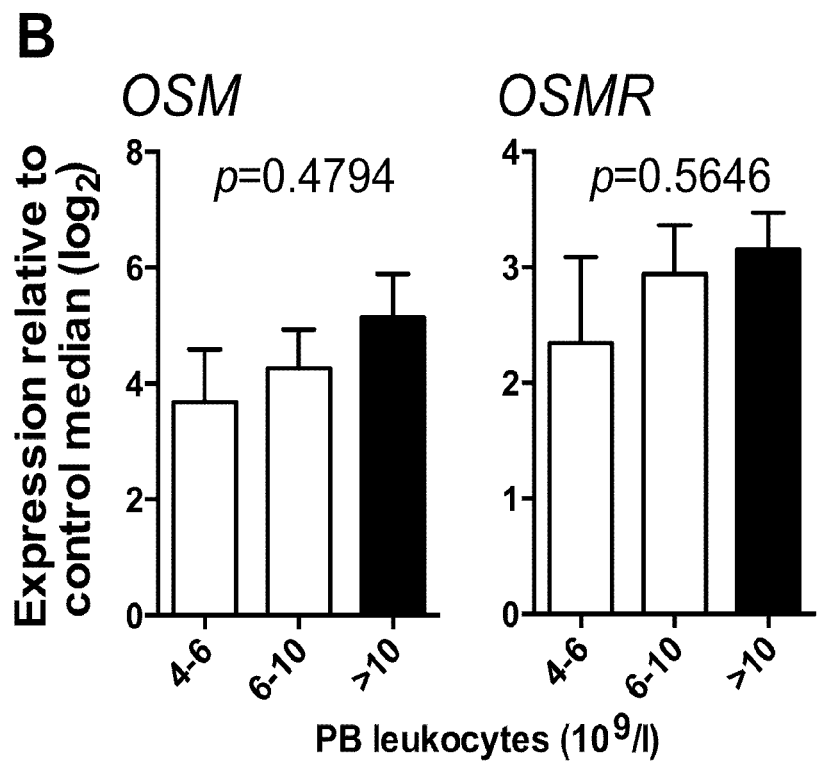
Figure 10:
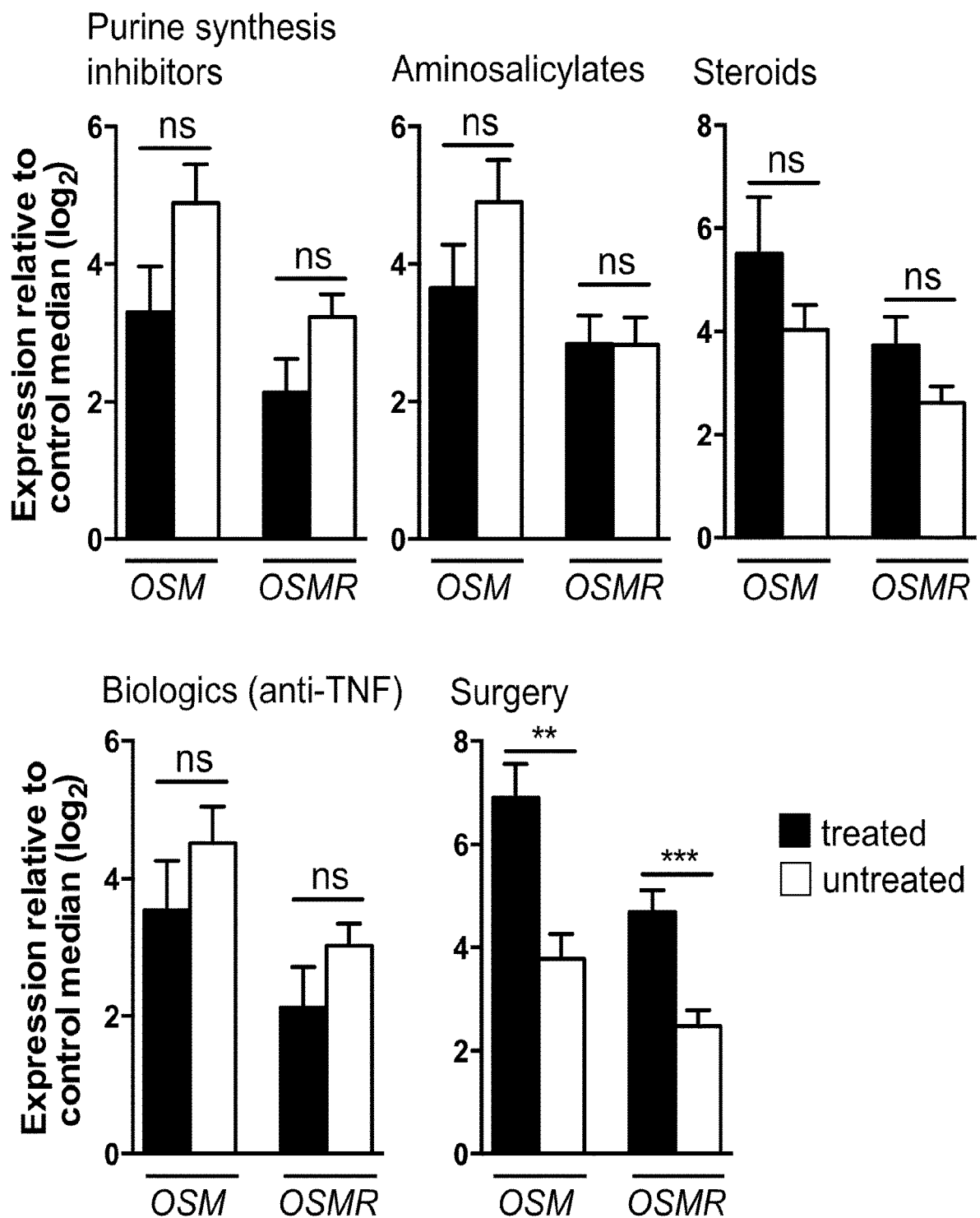

Data shown in FIG. 8 and FIG. 9 demonstrate that OSM and OSMR are expressed at equivalent levels in the mucosa of IBD patients irrespective of patient gender, age at diagnosis, disease duration, or systemic disease biomarkers such as serum CRP (C-reactive protein) and peripheral blood leukocyte counts. Of the various treatment classes given to patients in this study, OSM and OSMR expression were significantly associated only with a greater need for surgical intervention (with a trend towards increased steroid use), suggesting that activation of the OSM pathway is associated with aggressive treatment-refractory disease (FIG. 10). Together, these data suggest that OSM and OSMR are markers of tissue pathology that may be superior to conventional biomarkers such as serum CRP. Furthermore, OSM and OSMR expression is not restricted to specific subgroups of IBD patients.

Figure 11:
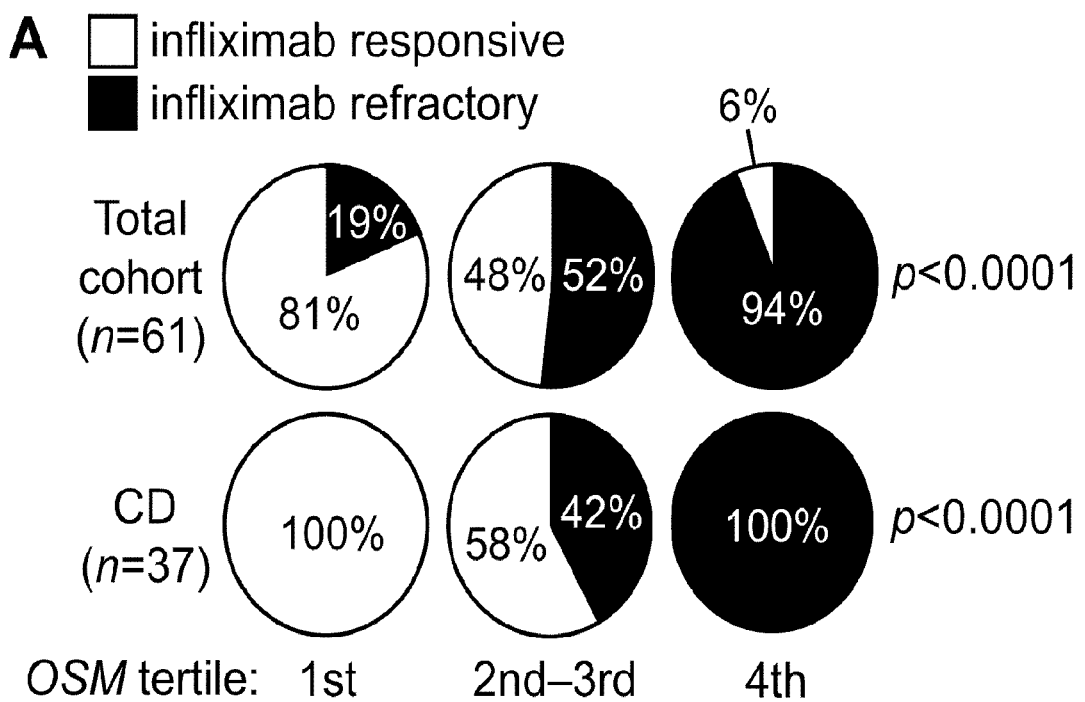
Figure 11:
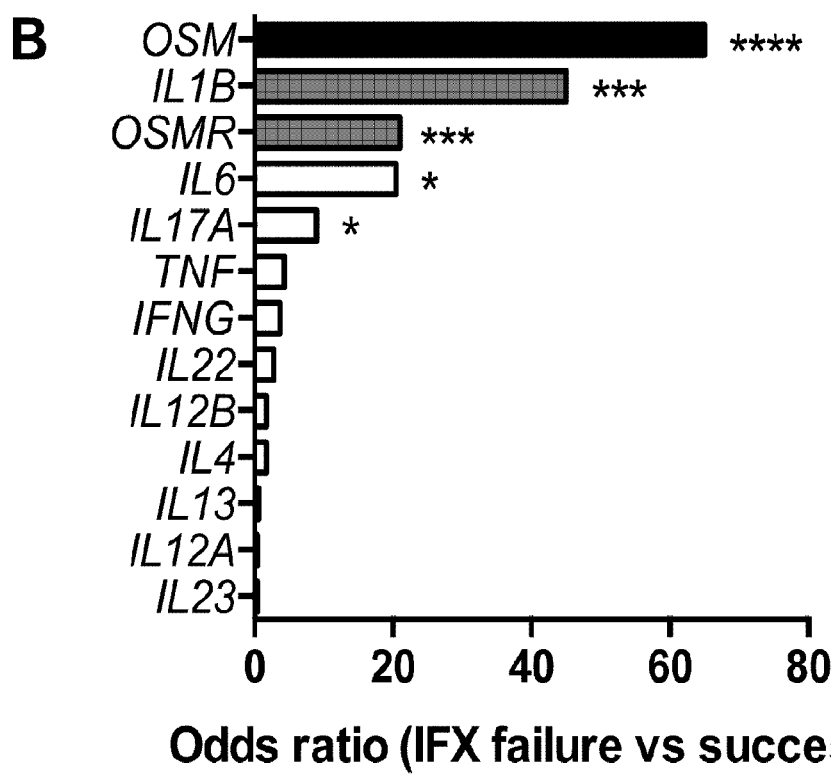
Figure 12:
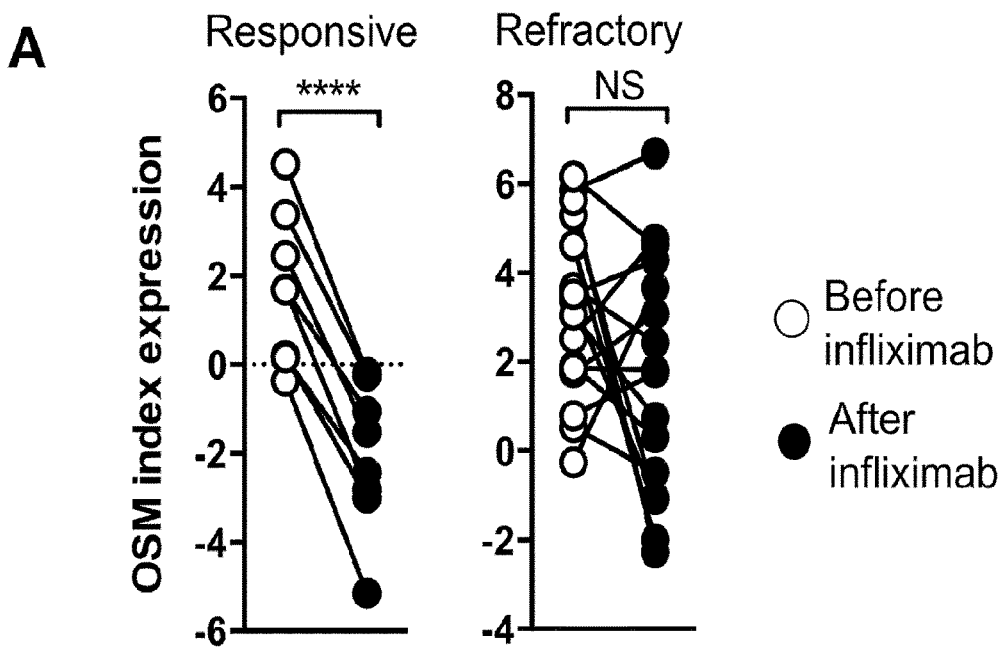
Figure 12:
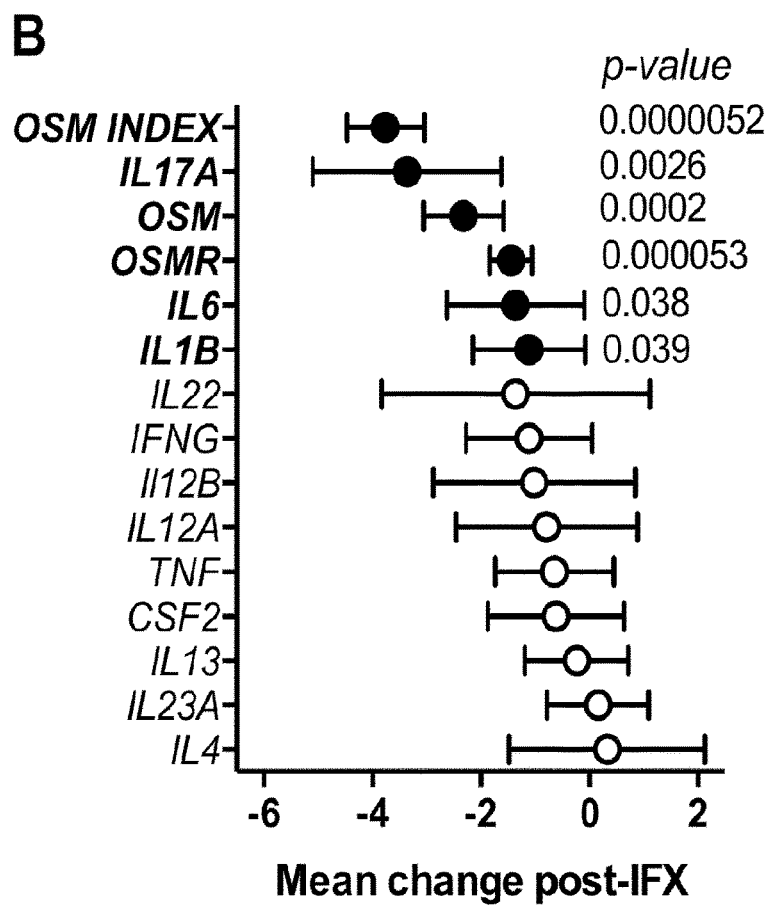
Figure 13:
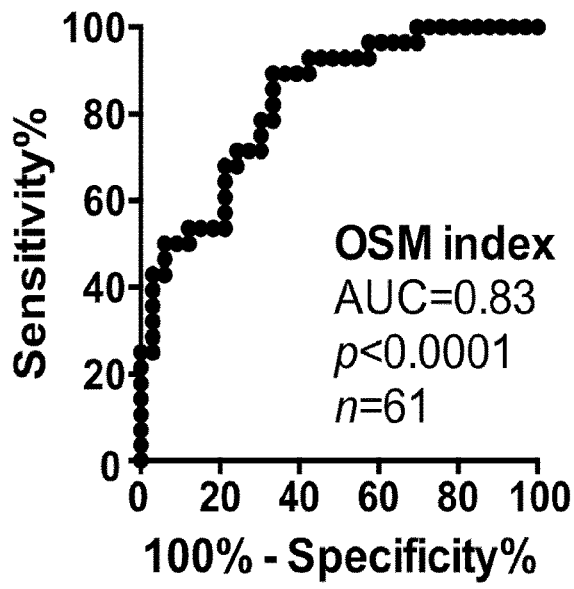
Figure 13:
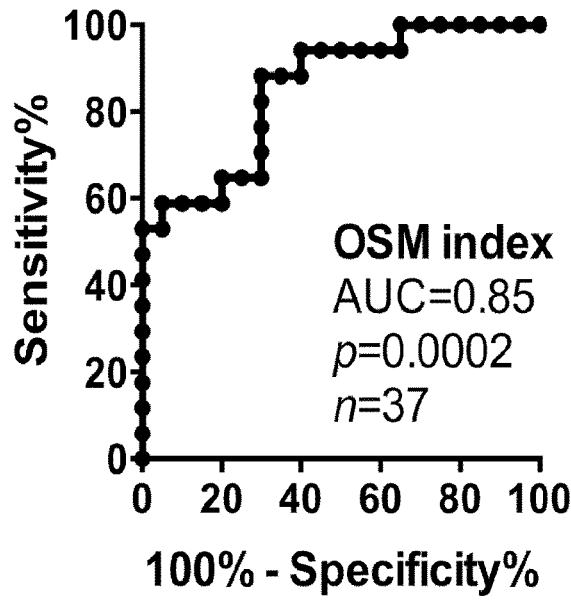
Figure 13:
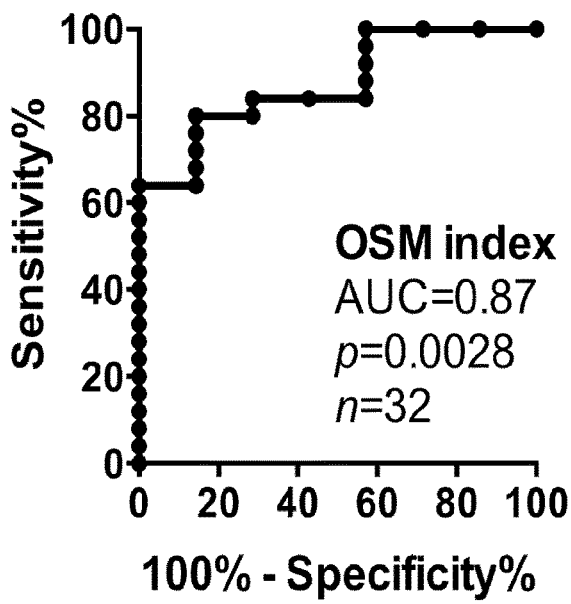
Figure 13:
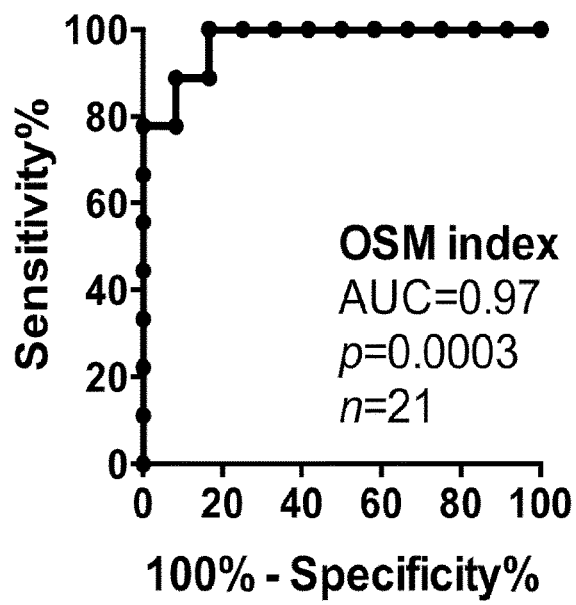
Figure 14:
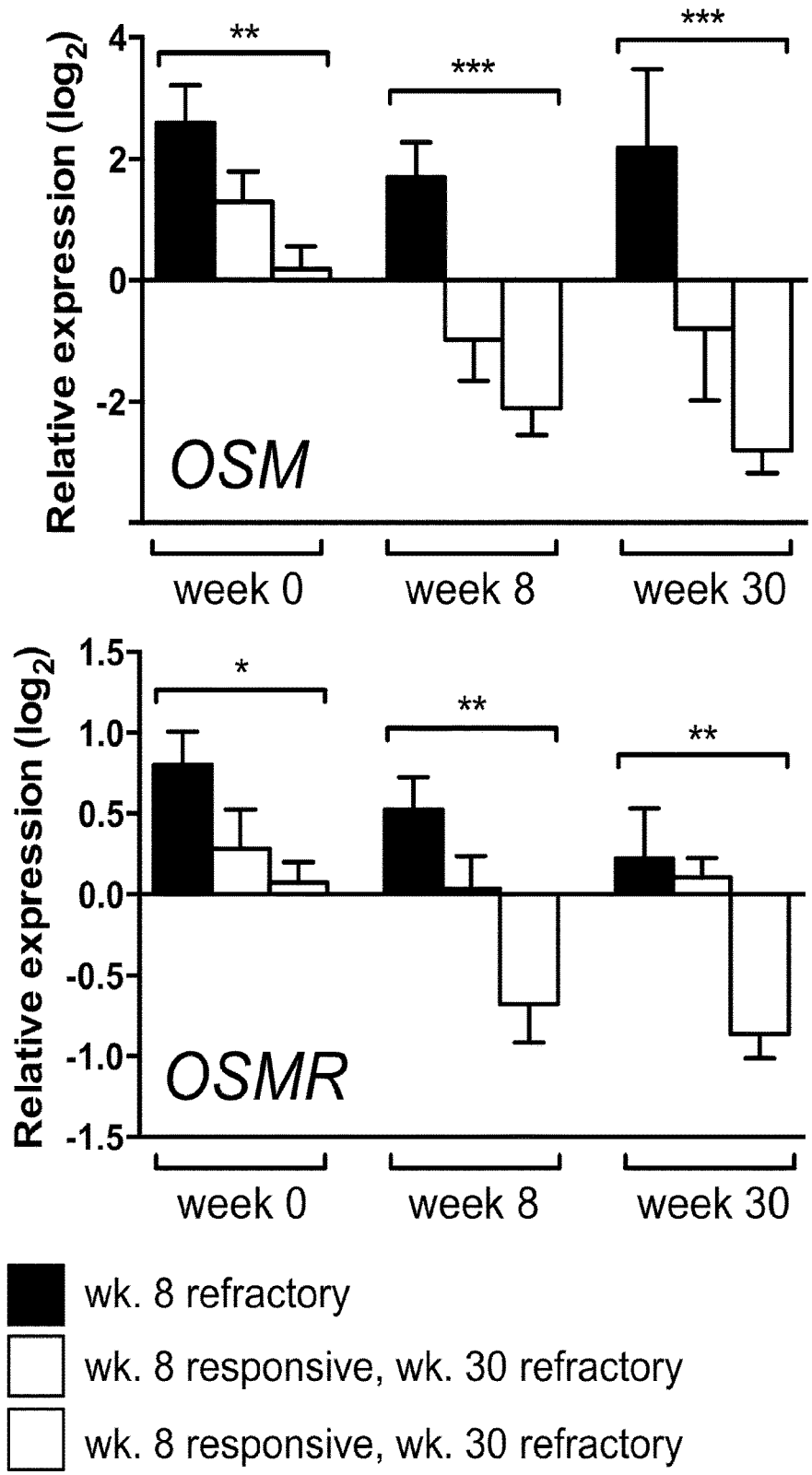
Figure 15:
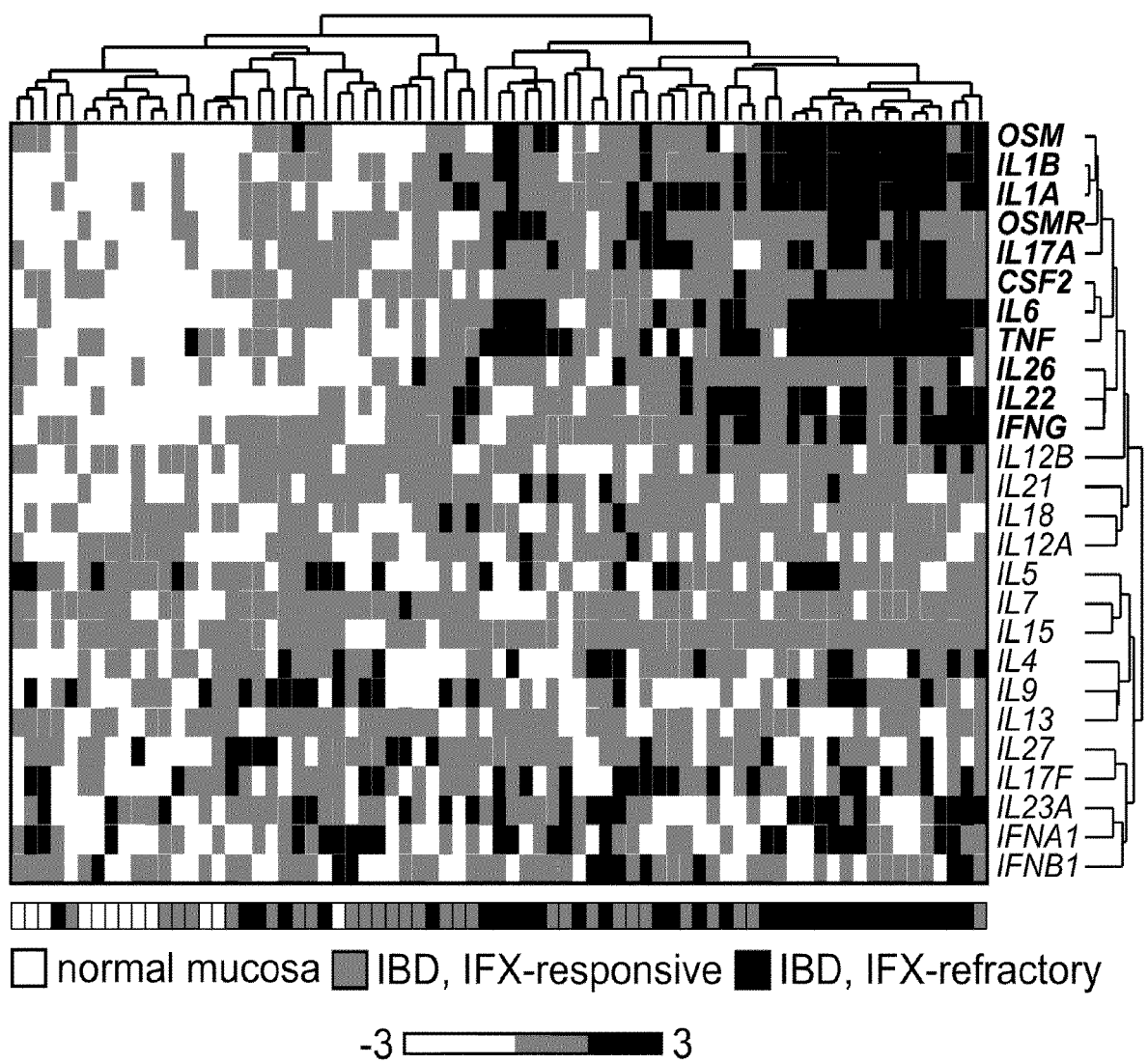
Figure 16:
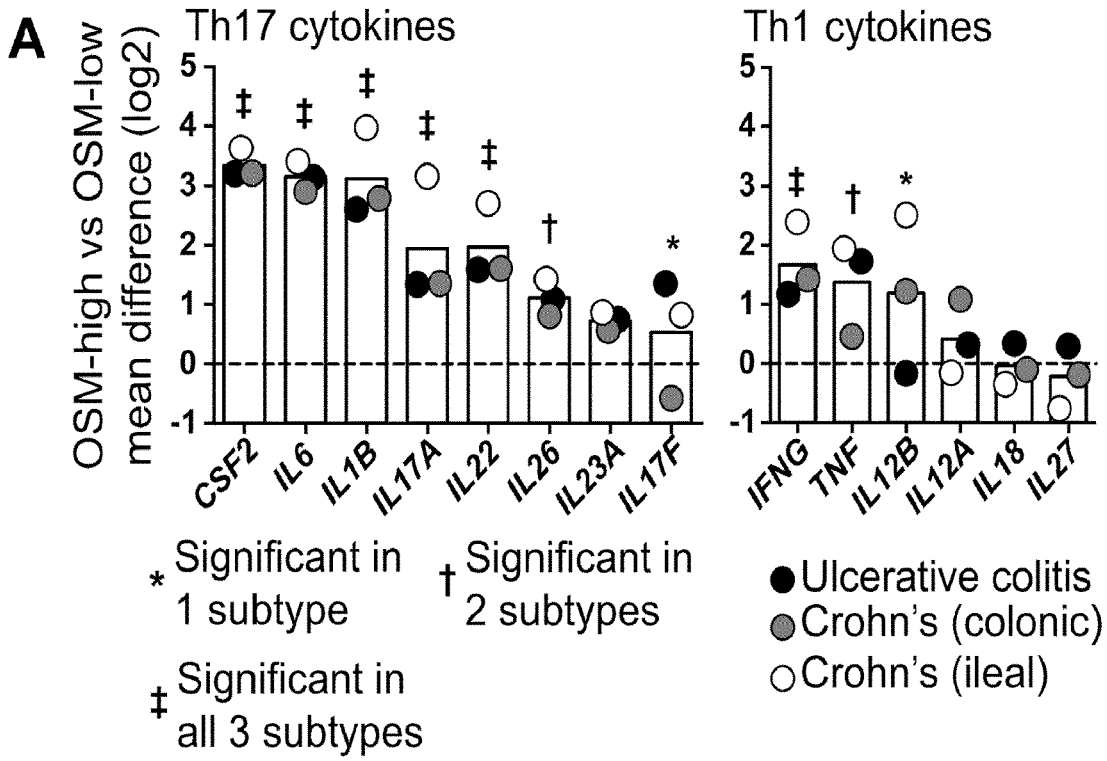
Figure 16:
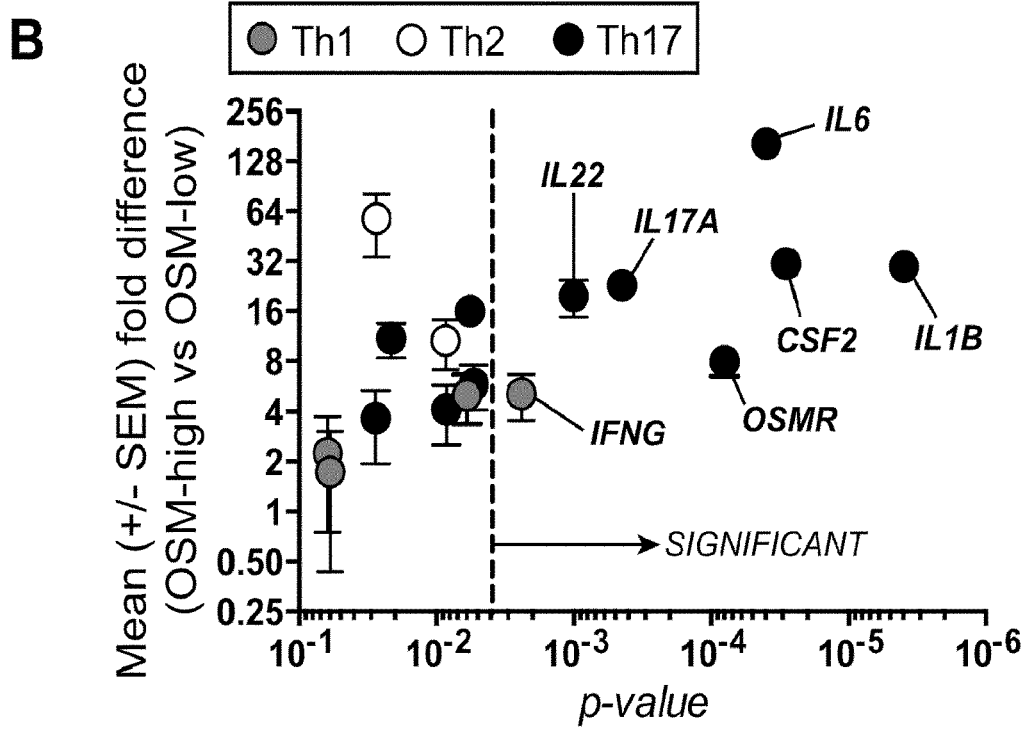

Example 6 the OSM Pathway is Associated with Clinical Response to Anti-TNFα Therapy in Human IBD The data shown in FIG. 11, FIG. 12, and FIG. 13 demonstrate that high expression of OSM and OSMR in the intestinal mucosa is robustly predictive of primary non-responsiveness to gold-standard biological therapy (infliximab) in IBD. Furthermore, OSM is a stronger predictor of treatment failure than other cytokines of clinical interest, and is one of the only cytokines that is reproducibly suppressed following successful anti-TNFα therapy. Notably, FIG. 14 demonstrates that OSM and OSMR are not only related to short-term infliximab response, but are also predictors of durable responses at time-points up to week 30. OSM, Example 7 OSM is Expressed in Association with a Mixed Th17/Th1 Cytokine Signature in IBD Deranged Th1 and Th17 T helper cell activity is thought to be critical for the pathogenesis of IBD. The data in FIG. 15 and FIG. 16 demonstrate that expression of OSM and OSMR is closely related to expression of cytokines that i) contribute to Th17 development (IL6, IL1B, IL23) or ii) are produced by Th1 and/or Th17 cells (IL17A, IFNG, CSF2, IL22). This is consistent across multiple cohorts and in all subtypes of IBD. Therefore, OSM is expressed in the context of what are believed to be pathogenic immune responses in the human intestine.

Figure 18:
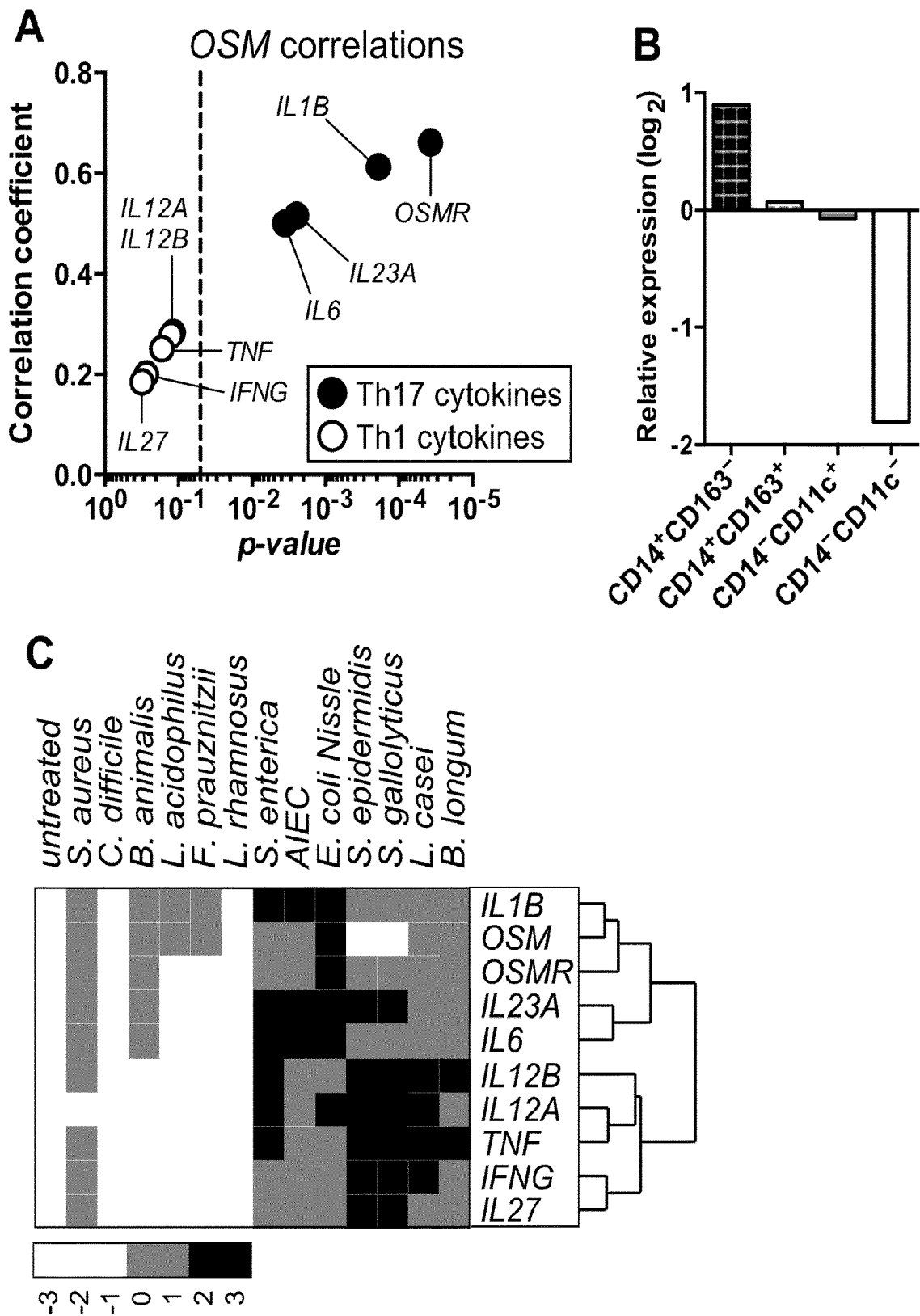

Example 8 OSM is Expressed in Association with Th17-Polarizing Cytokines by Bacteria-Stimulated Human Monocytes Antigen presenting cells, including monocytes, are critical for the activation and differentiation of naïve CD4[+] T cells and in the re-stimulation of memory CD4[+] T cells. The cytokines that they express in the context of antigen presentation are the primary determinants of the differentiation pathway and thus effector function of a helper T cell. The data in FIG. 17 show that OSM expression is strongly induced by human monocytes upon exposure to various bacterial molecules, as well as a wide range of whole bacteria representing diverse genera found on human mucosal surfaces, including both pathogenic and commensal species. FIG. 18 demonstrates that OSM is expressed in association with the Th17-polarizing cytokines IL-6, IL-1β, and IL-23 in monocytes following bacterial challenge. Furthermore, OSM is highly expressed by an antigen presenting cell subtype found in the human intestine that has strong Th17-inducing capacity. Collectively, these data implicate OSM as a previously unknown component of the Th17 induction pathway that is strongly induced by human antigen-presenting cells upon exposure to microbial stimuli, a process that is thought to occur at increased levels in the intestinal tissue of IBD patients.

Example 9 OSM is Expressed in Human Memory CD4+ T Cells

Figure 19:
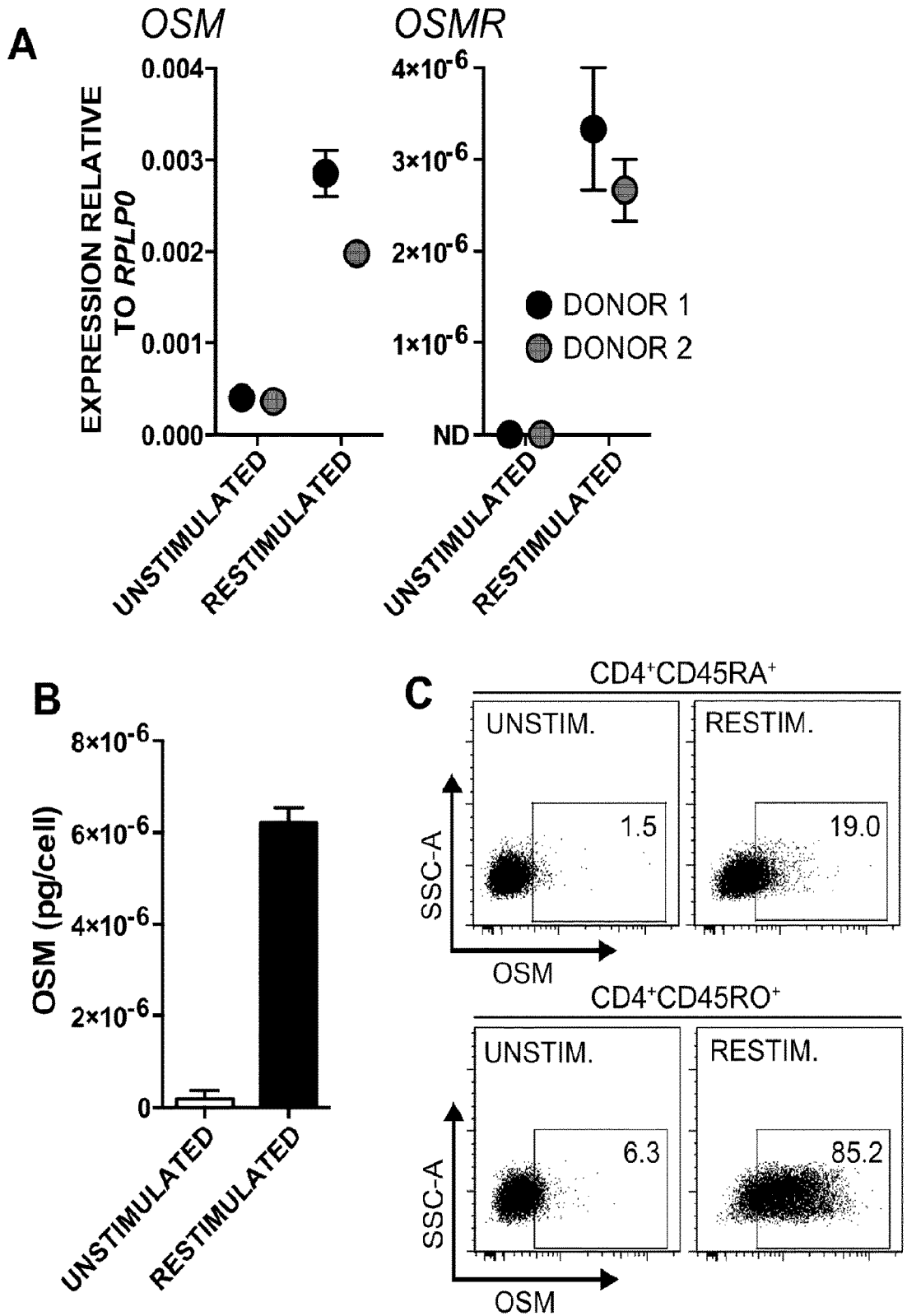

The data in FIG. 19 demonstrate that OSM is expressed at the mRNA and protein level by CD4+ T cells following stimulation. Furthermore, while resting CD4+ T cells do not express detectable OSMR, they induce OSMR expression upon activation. OSM expression is primarily a feature of memory (CD45RO+) cells. CD4+ T cells are therefore both a source and potential target cell of OSM in humans.

Example 10 OSM Enhances Human Th17 Differentiation and Expansion

Figure 20:
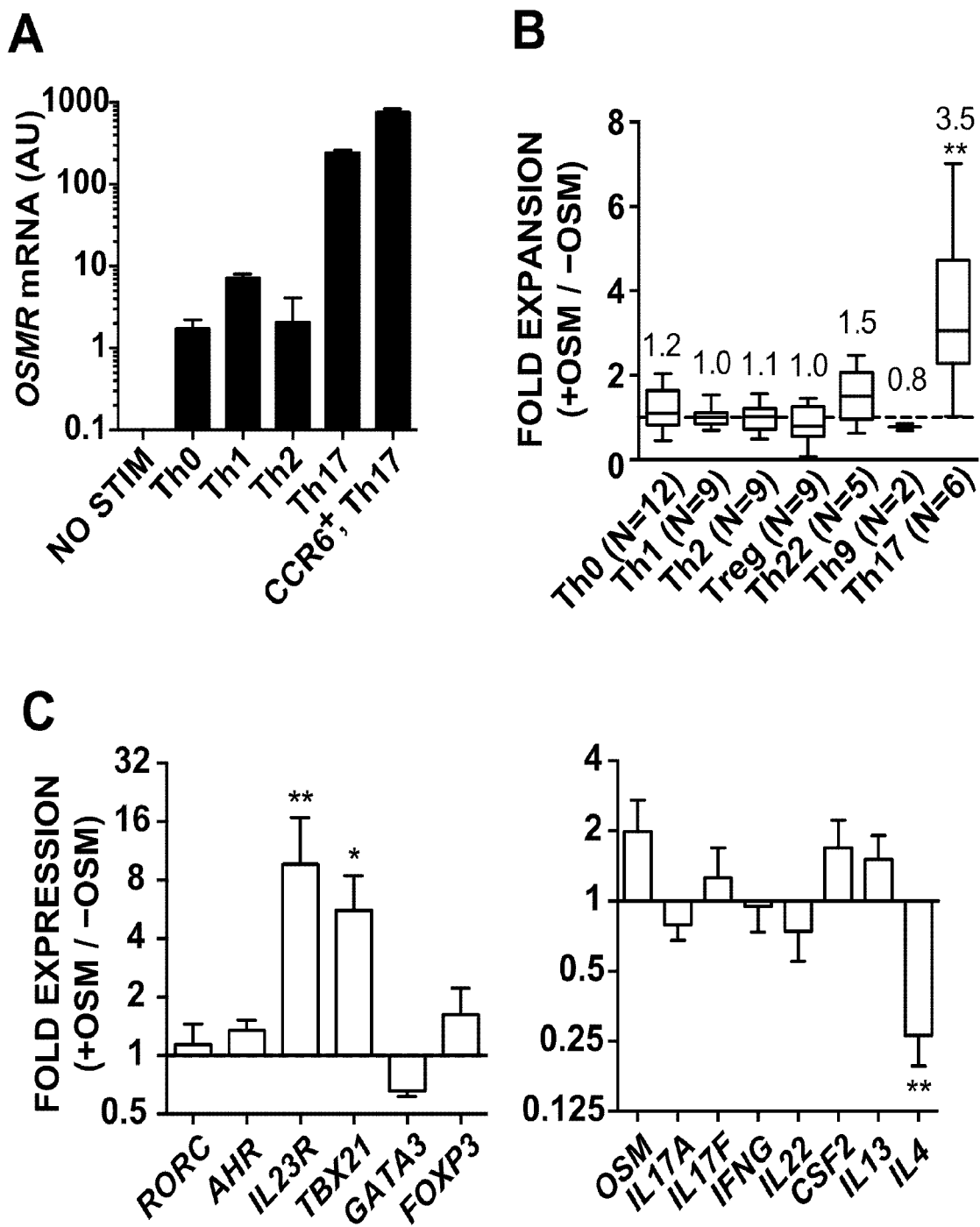

The data in FIG. 20 show that Th17-polarized CD4+ T cells express elevated levels of OSMR, and that OSM enhances the expansion of naïve CD4+ T cells activated under Th17 conditions. CFSE (carboxyfluorescein succinimidyl ester) and PI (propidium iodide) staining suggests that this is due to an enhancement of cell survival, rather than proliferation (not shown). OSM suppresses expression of the master Th2 transcription factor GATA3, as well as the signature Th2 cytokine IL-4 in Th17 cells, and thus enhances the purity of the resulting Th17 phenotype. Furthermore, OSM enhances expression of the IL-23 receptor in Th17 cells, which may render them more prone to developing IL-23-dependent pathogenic functions. These data suggest that OSM could play an important role in enhancing pathogenic Th17 responses in humans.

Example 11 OSM is Necessary for Aggressive Colitis In Vivo

Figure 21:
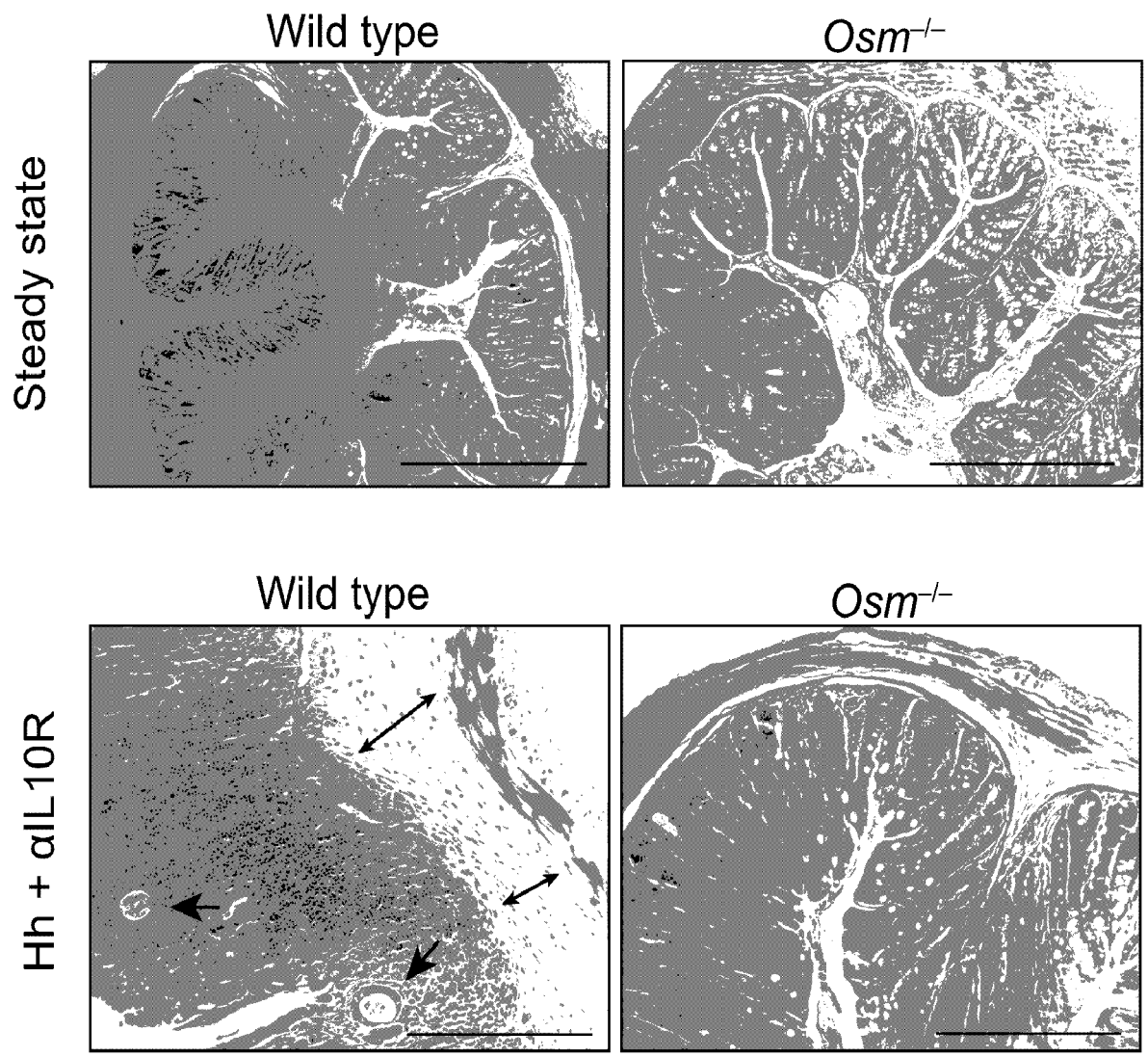
Figure 22:
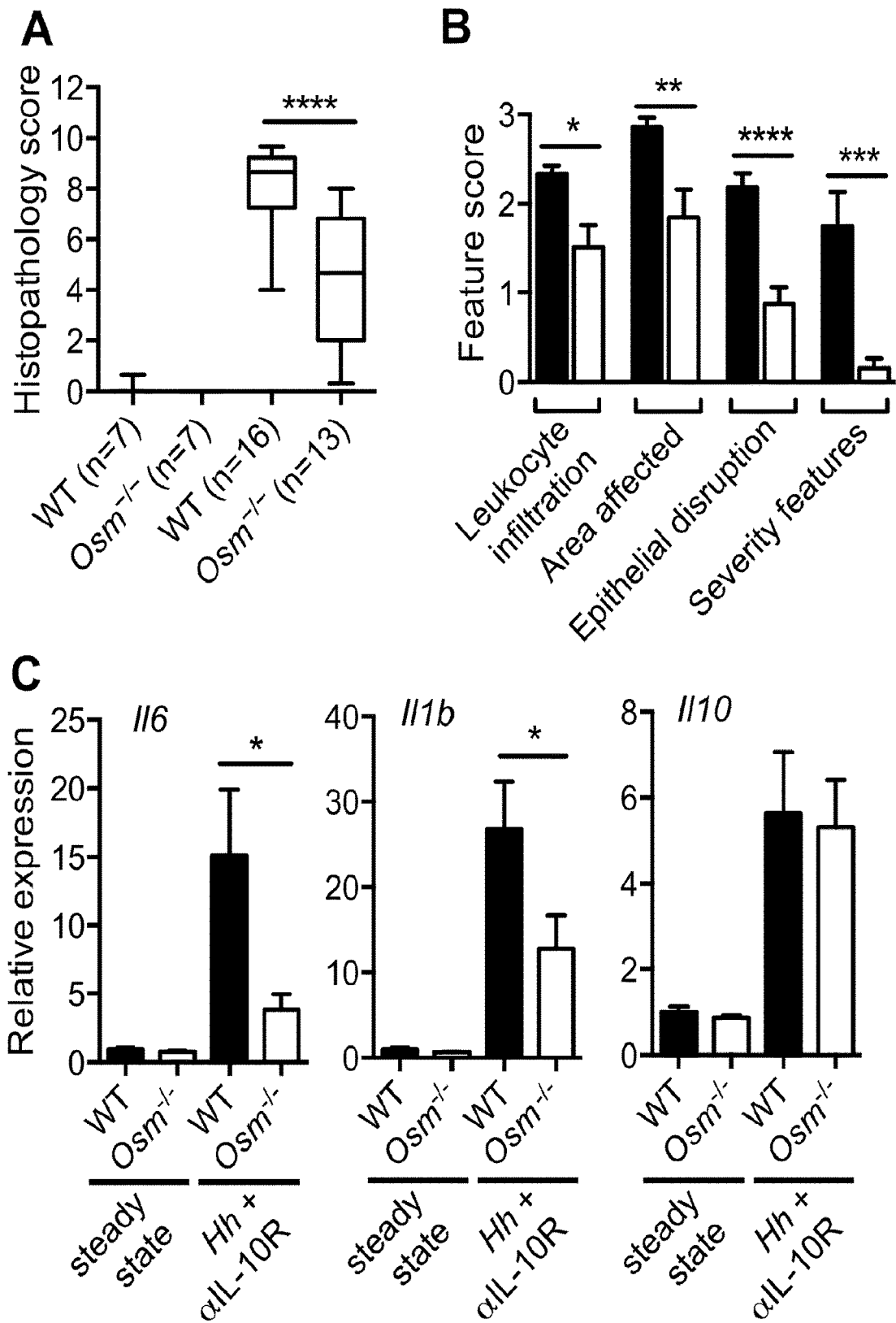

The data in FIG. 21 and FIG. 22 demonstrate that in mice with genetic deletion of OSM, the Hh+αIL10R colitis protocol leads to substantially attenuated disease relative to wild type littermate controls. While this is evident for all major parameters of histological assessment (including epithelial/goblet cell disruption and leukocyte infiltration), this is particularly clear at the level of severe disease manifestations, such as abscess formation, submucosal inflammation, and interstitial oedema. Furthermore, the absence of OSM attenuates expression of other inflammatory cytokines in the intestine, notably IL-6 and IL-10, without impairing induction of the anti-inflammatory cytokine IL-10. Therefore, OSM appears to be an upstream driver of more classical pro-inflammatory pathways such as IL-6, but it is not required for induction of beneficial immunoregulatory pathways. Importantly, detailed examination of multiple lymphoid and peripheral organs revealed that Osm$^{-/-}$ mice show no overt immunological phenotypes at steady state, nor is the intestinal architecture abnormal (unpublished, not shown). Furthermore, Osm$^{-/-}$ and wild type littermates show equivalent *H. hepaticus* colonization in the intestine, demonstrating that the protective effect of Osm deletion in this colitis model is not due to altered bacterial handling (unpublished, not shown).

Example 12 Neutralization Efficacy of O-RFP, a Novel Mouse OSM Blockade Reagent

Figure 23:
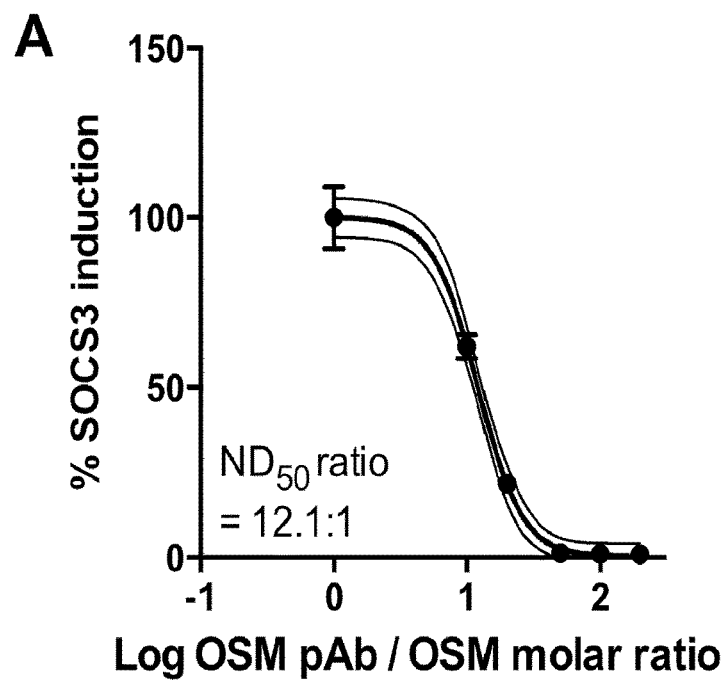
Figure 23:
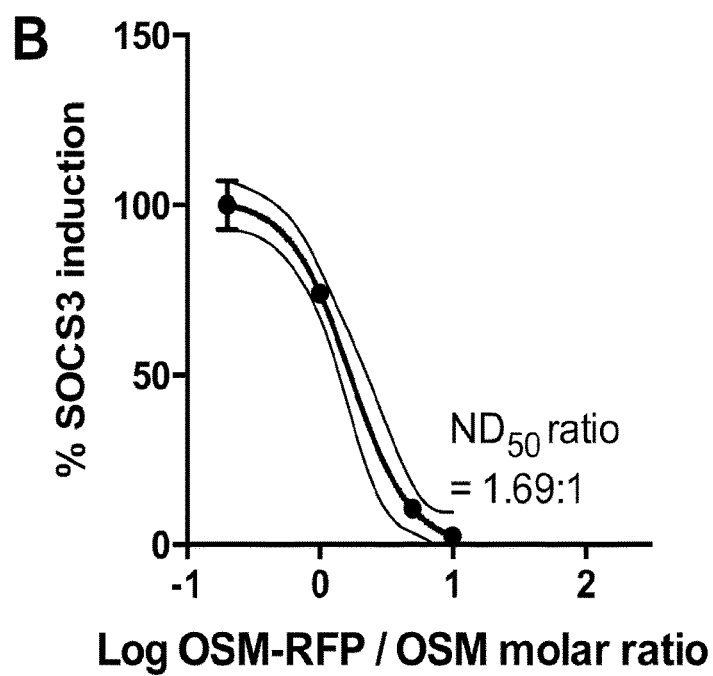

The data in FIG. 23 demonstrate the capacity for O-RFP (see Methods and FIG. 23 description) to neutralize mouse OSM in vitro. This protein has superior neutralization capacity as compared to commercially available polyclonal antisera.

Example 13 Therapeutic OSM Blockade Attenuates Colitis In Vivo

Figure 24:
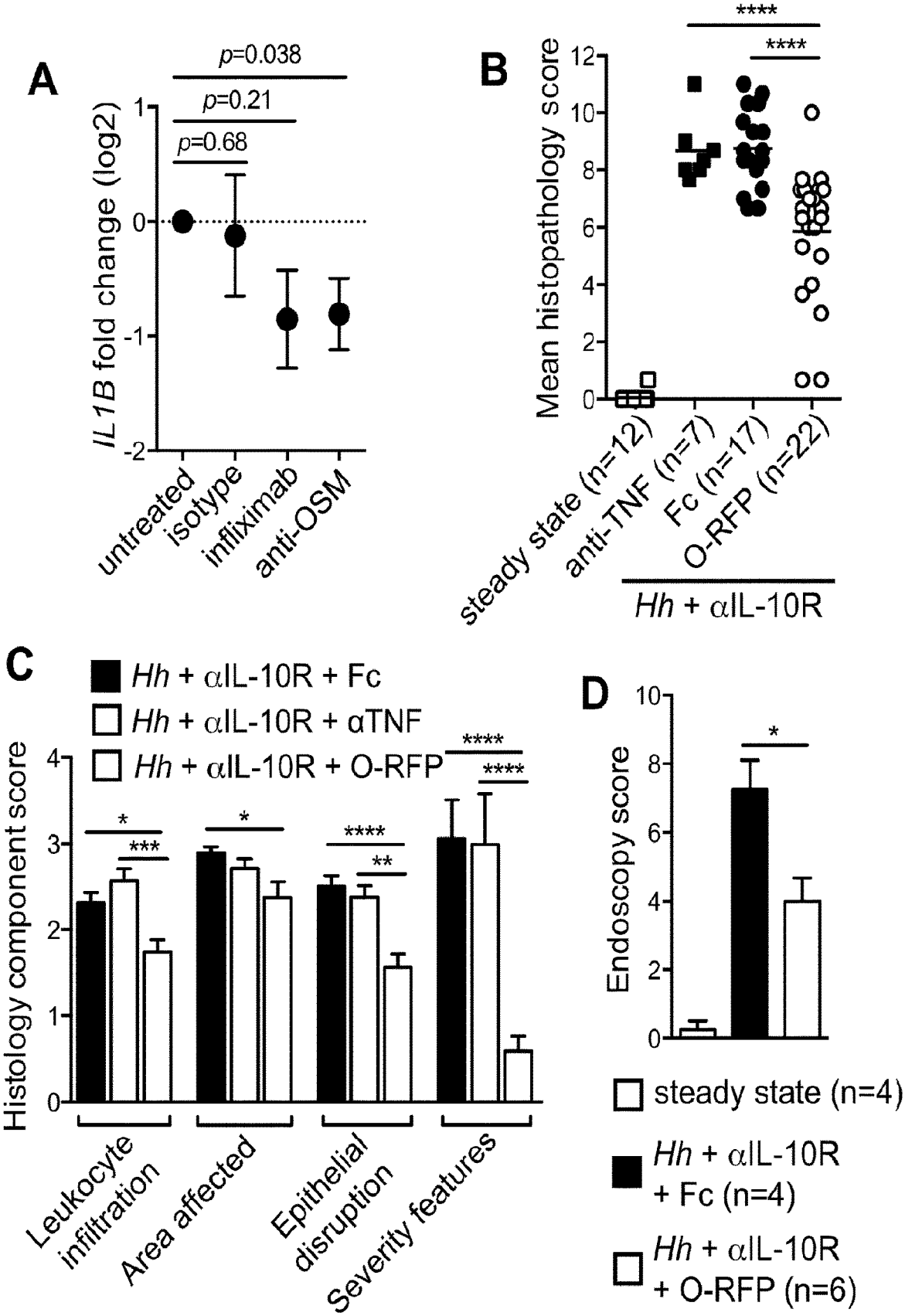

The data in FIG. 24 demonstrate that therapeutic blockade of OSM using O-RFP in mice with established colitis (treatment initiated at day 7 of the Hh+αIL10R protocol) reduces disease severity as determined by both endoscopic and histological criteria. This therapeutic effect is superior to that of TNF blockade. Consistent with the results obtained from OSM knockout mice (see Example 11), the clearest OSM-dependent parameter in these experiments was the manifestation of severe disease features. Furthermore, blockade of human OSM using a specific monoclonal antibody in intestinal mucosal explant cultures from 5 different human CD patients significantly attenuates tissue inflammation as demonstrated by reduced IL-10 expression. This effect is comparable to that of infliximab. Together, these data suggest that OSM is a potentially valuable clinical target for IBD, particularly for aggressive disease phenotypes that are resistant to anti-TNF therapy.

Targeting OSM in the context of therapeutic intervention for IBD is thus a valid strategy.

Figure 25:
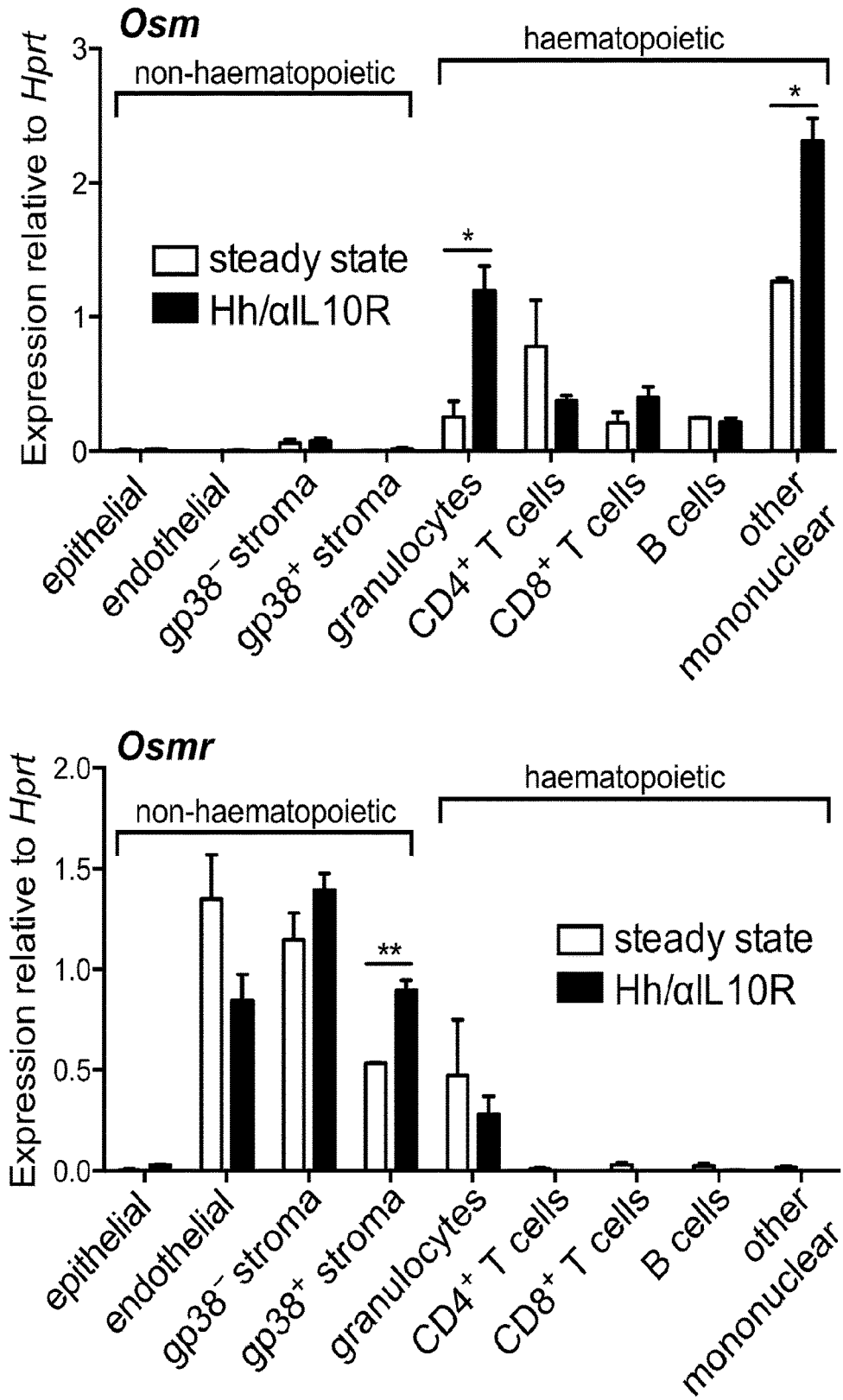
Figure 26:
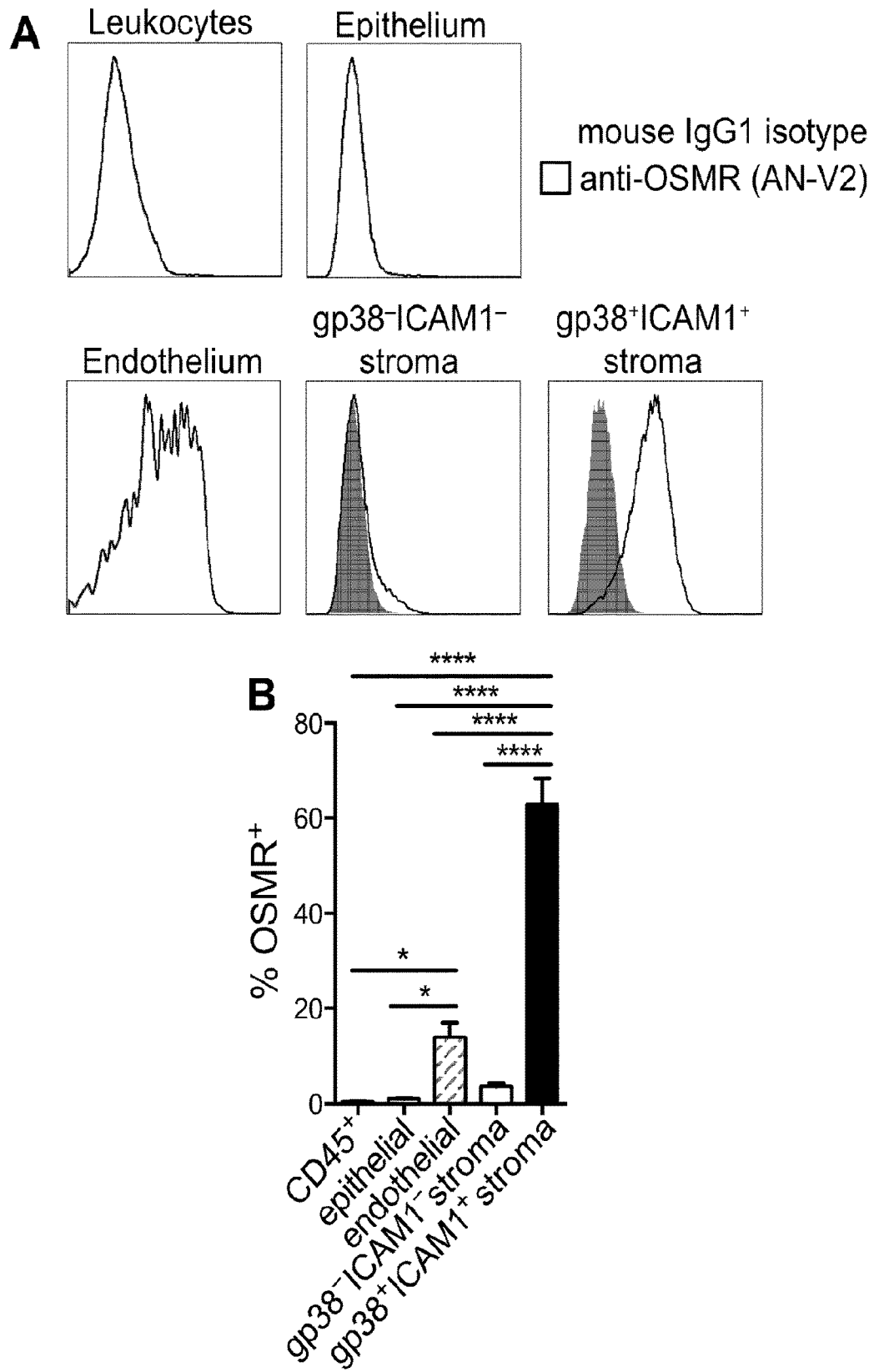

Example 14 OSM is Expressed Widely by Haematopoietic Populations, while Non-Haematopoietic Stromal Cells are a Major OSM-Responsive Cell Type in the Intestine Data in FIG. 25 show that in wild type mice, OSM production in the intestine can be attributed to various leukocyte subtypes such as CD4+ T cells and antigen presenting cells. Notably, the highest expression levels of OSMR are observed on intestinal stromal cells and endothelial cells. In contrast, OSMR is expressed at much lower levels in haematopoietic populations and epithelial cells. Data in FIG. 26 demonstrate similar results in human intestinal cell populations, where OSMR staining by flow cytometry analysis reveals a restricted staining pattern that includes only stromal cells and, to a lesser extent, endothelial cells. OSMR+ stromal cells also bear gp38 and ICAM-1, markers of an immunologically active "lymphoid tissue-like" stromal population (Owens, *Front Immunol*, 2015). Because this stromal cell subset substantially outnumbers endothelial cells in the tissue, we conclude that gp38+ ICAM-1+ stromal cells are the dominant OSM-responsive cell type in both the mouse and human intestine. As expected, staining for OSM protein expression in human intestinal tissue revealed production by diverse haematopoietic populations including T cells and antigen presenting cells (not shown).

Example 15 Intestinal Stromal Cells are Highly Responsive to OSM

Figure 27:
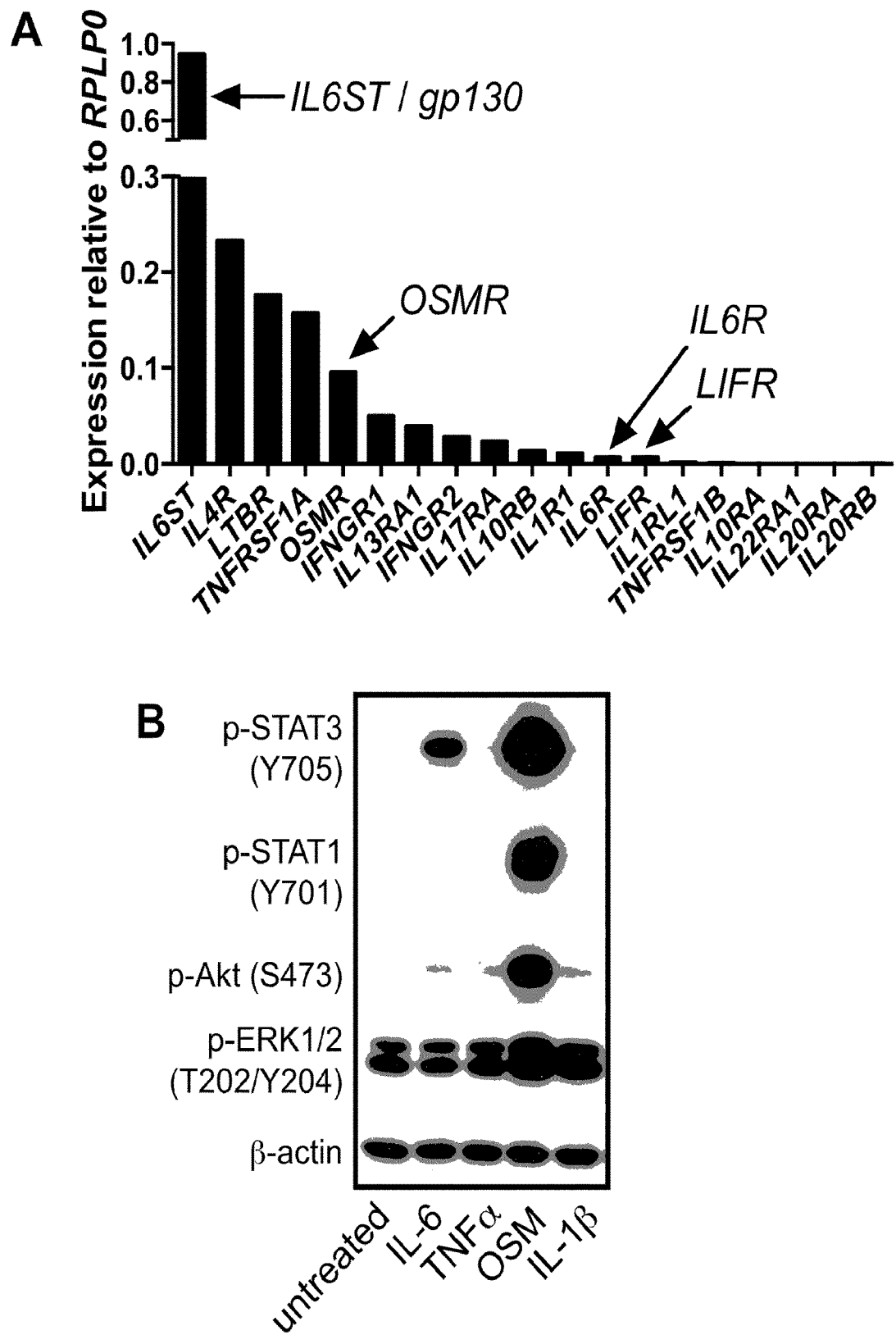

Data shown in FIG. 27 demonstrate that relative to other cytokine receptors, OSMR is expressed at high levels by primary human intestinal stromal cells. Similarly, the heterodimeric partner of OSMR (gp130) is very highly expressed. In contrast, other receptors of the OSMR family are expressed at low levels, such as IL-6 receptor and LIF receptor. Consistent with high OSMR/gp130 expression, OSM stimulates rapid and strong signal transduction responses via diverse pathways in intestinal stromal cells, whereas the response to IL-6 is much lower. Therefore, OSM appears to be an important member of its family with respect to intestinal stromal cell biology.

Figure 28:
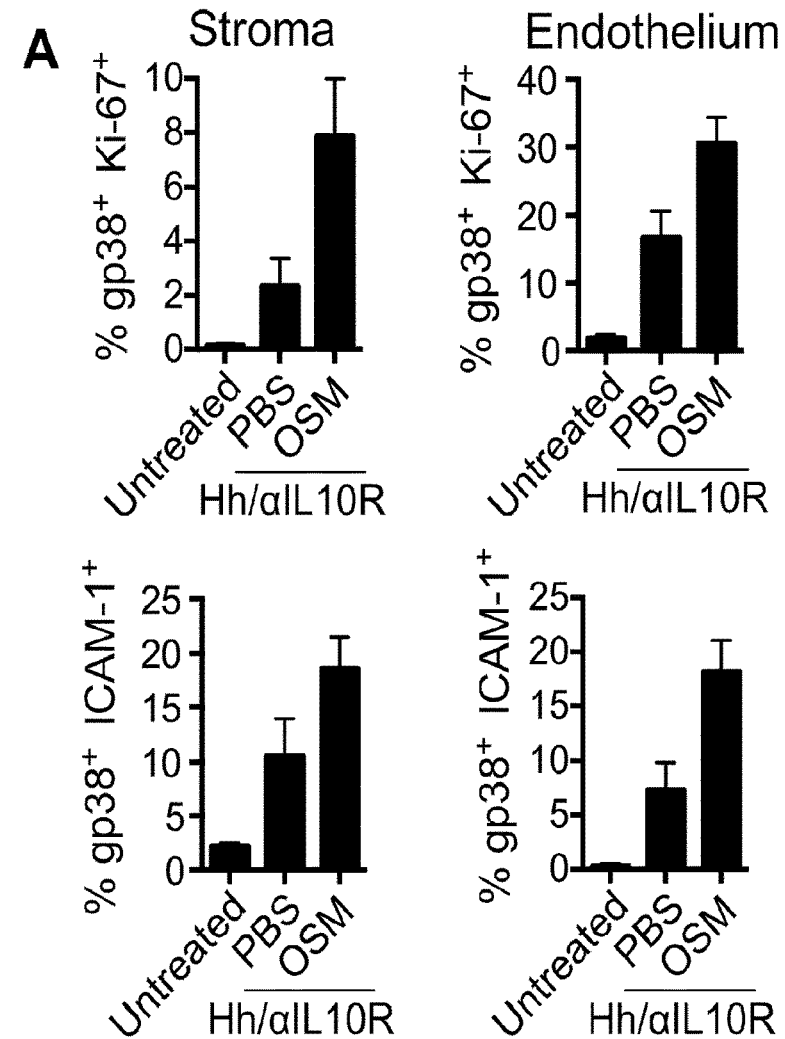
Figure 28:
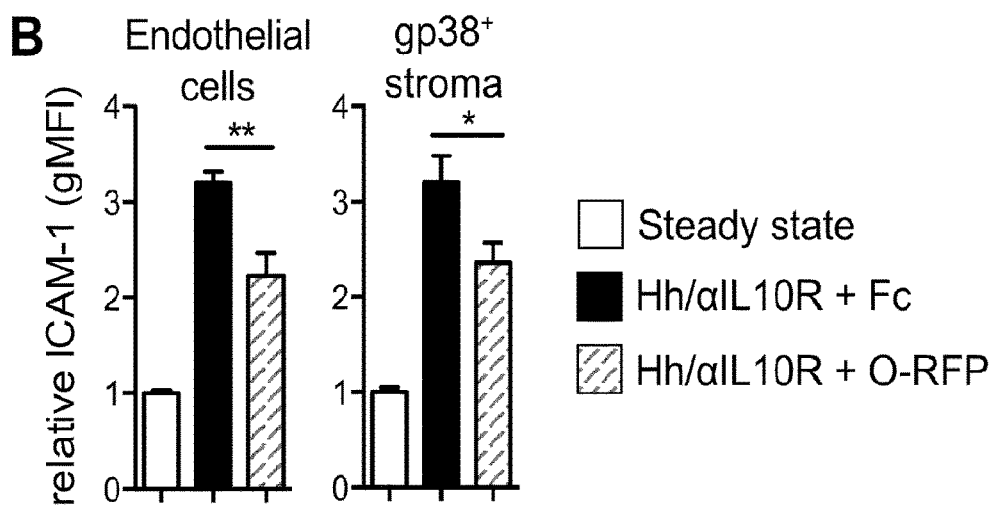

Example 16 Intestinal Stromal Cells and Endothelial Cells are Modulated by OSM In Vivo The data in FIG. 28 indicate that i) intestinal stromal cells and endothelial cells are activated (based on ICAM-1 surface expression) and show enhanced proliferation during murine colitis and; ii) that OSM further promotes their activation and proliferation when administered systemically during the course of Hh+αIL10R colitis. Systemic OSM treatment also results in a stronger colitis phenotype featuring exacerbated leukocyte recruitment and worsened histological disease severity (not shown). When mice are subjected to Hh+αIL10R colitis, OSM blockade with O-RFP significantly attenuates accumulation of ICAM-1 on the surface of both endothelial cells and gp38$^+$ICAM-1$^+$ stromal cells. Similar results are observed using OSM knockout mice (not shown). Therefore, OSM modulates the inflammatory activation state of stromal/endothelial populations in vivo and may be an important mechanism by which OSM promotes colitis severity.

Figure 29:
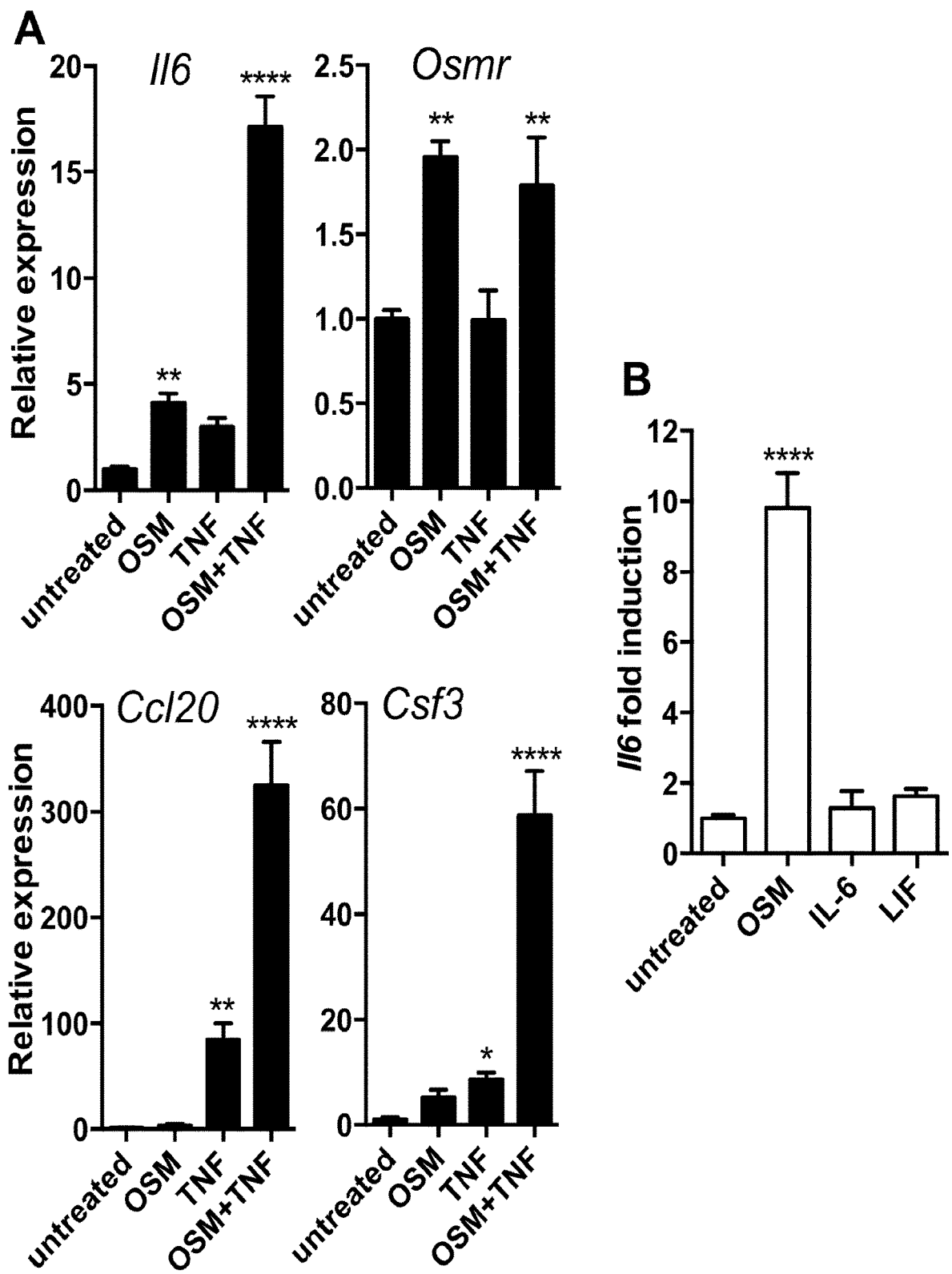

Example 17 OSM Activates Cytokine and Chemokine Expression in Mouse Intestinal Stromal Cells in Synergy with TNF Data in FIG. 29 demonstrate that mouse colonic intestinal stromal cells cultured ex vivo are responsive to OSM and express several relevant inflammatory factors in response to OSM stimulation. Notably, several response genes are induced at very high levels when cells are co-stimulated with OSM and TNF, suggesting that OSM and TNF constitute a functional pro-inflammatory axis in the intestine. Although intestinal stromal cells are highly responsive to OSM, they are largely non-responsive to the closest homologues of OSM: IL-6 and LIF.

Figure 30:
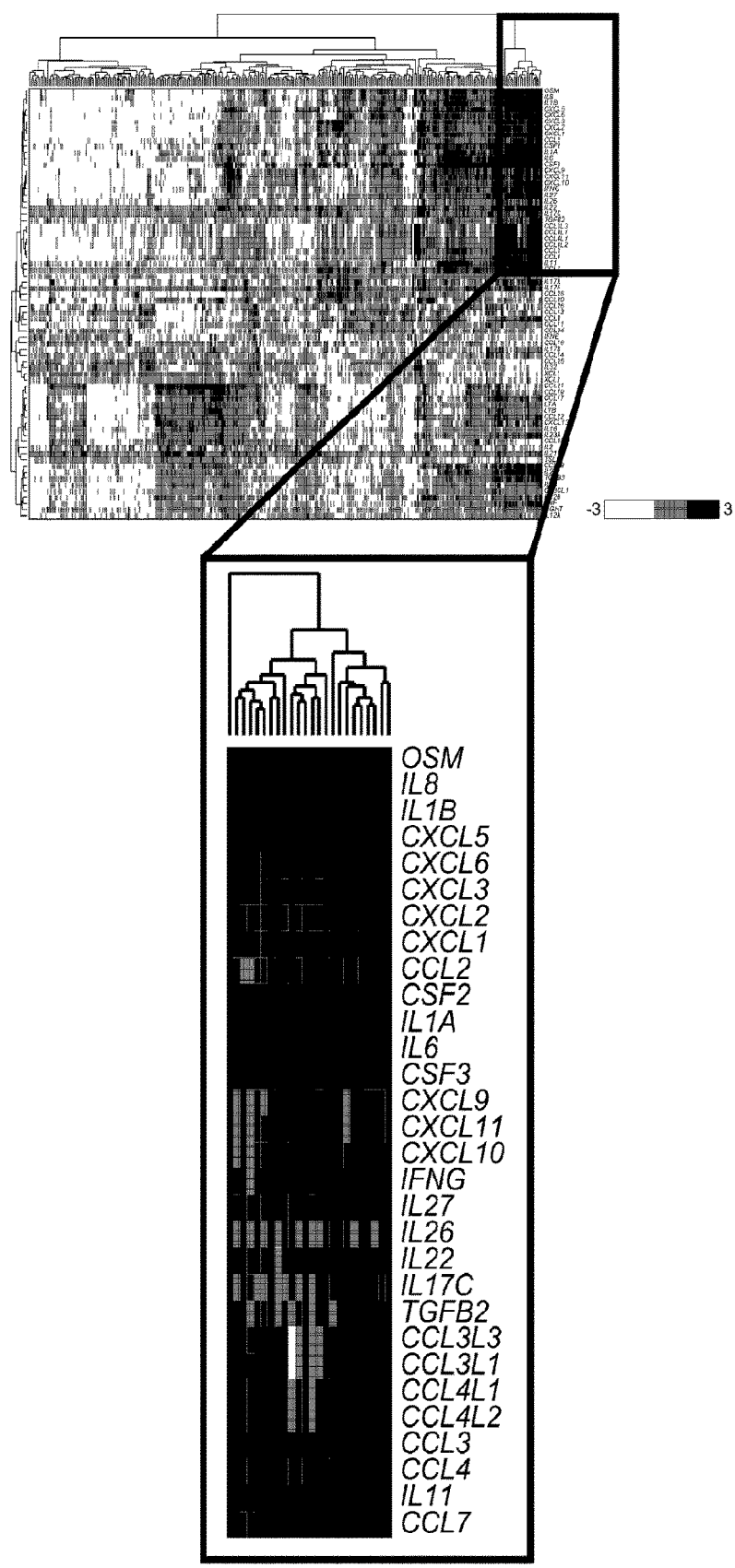
Figure 31:
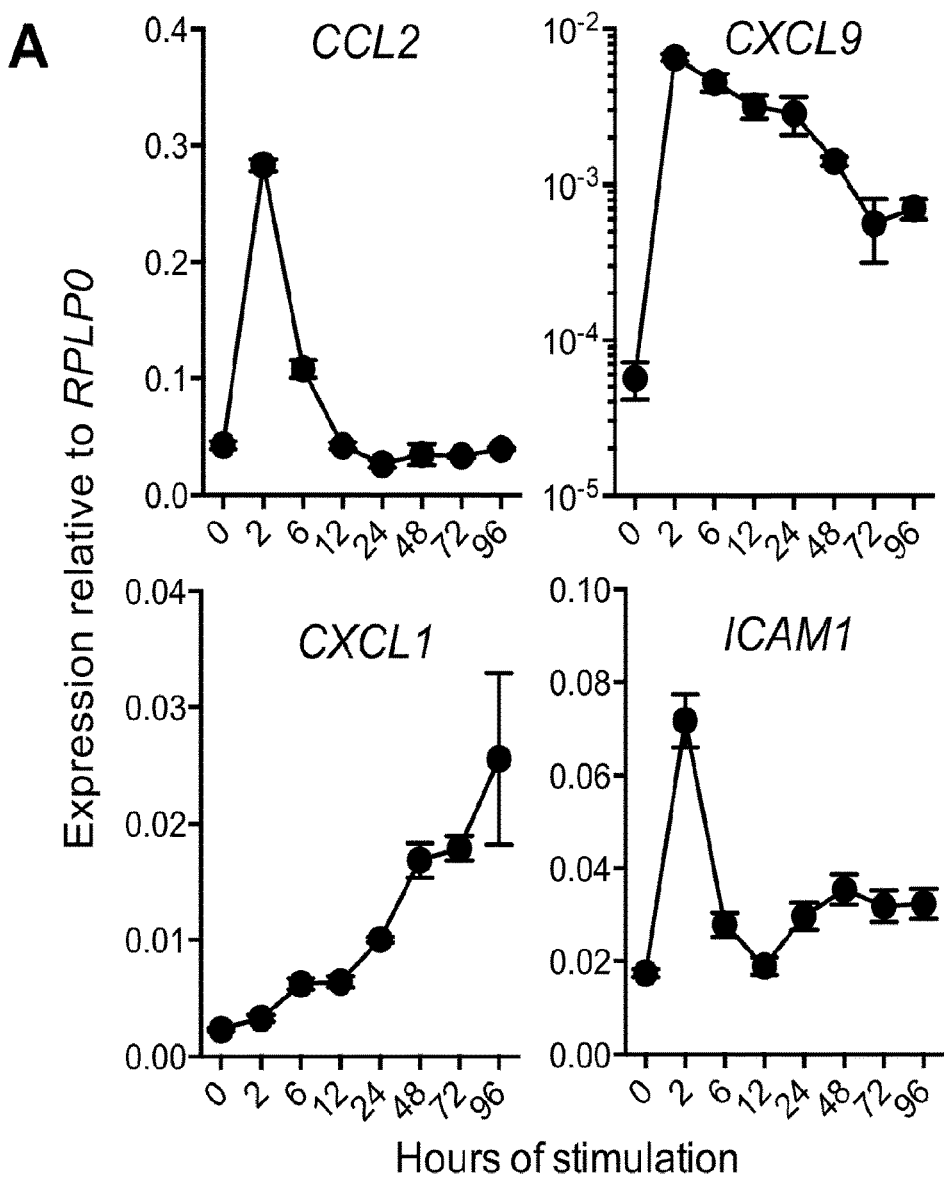
Figure 31:
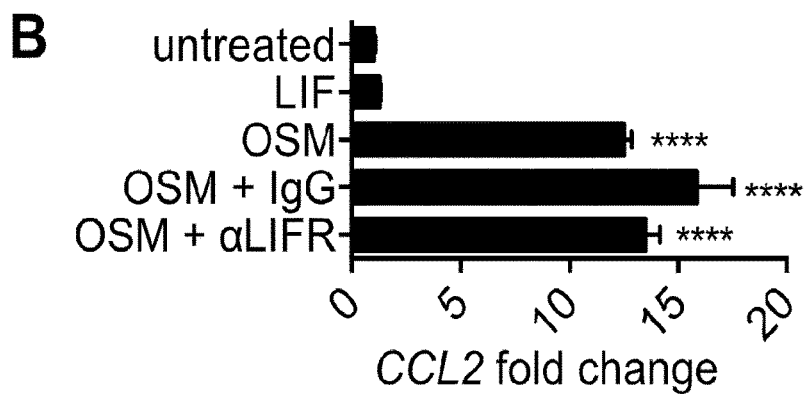
Figure 33:
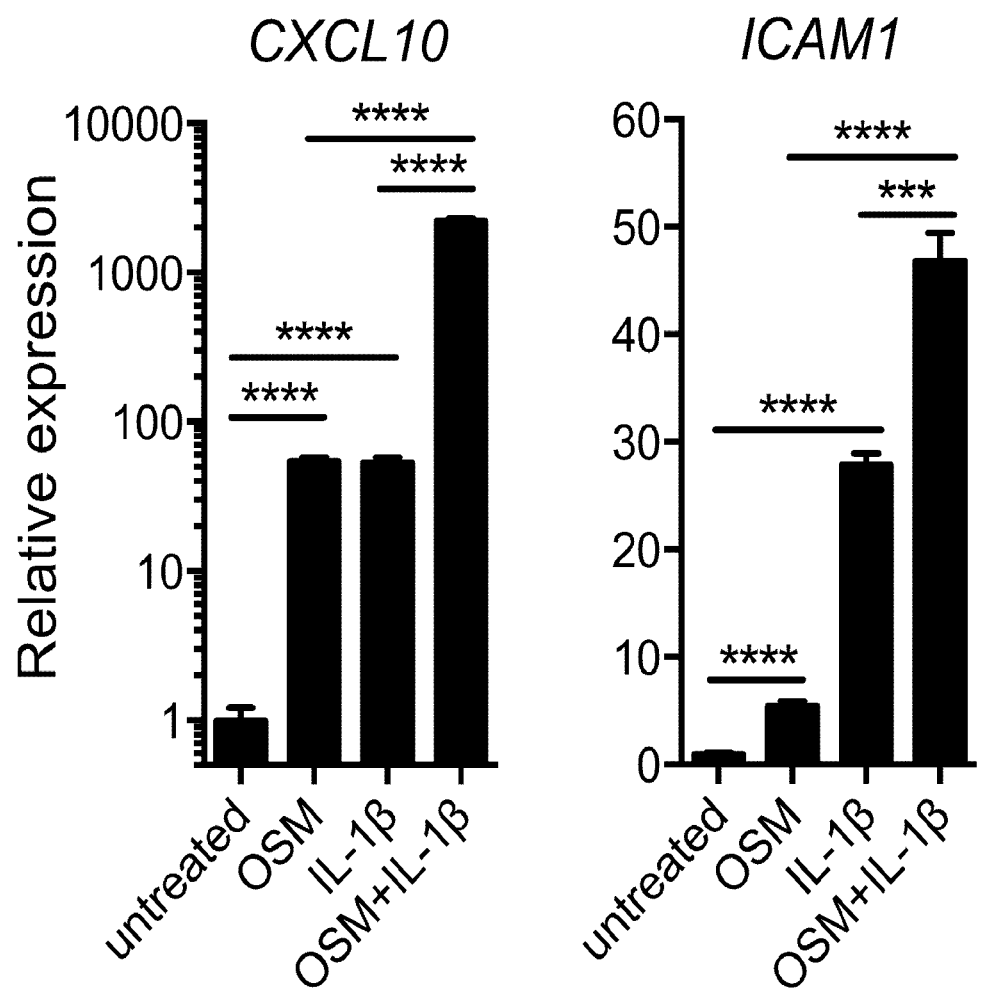
Figure 34:
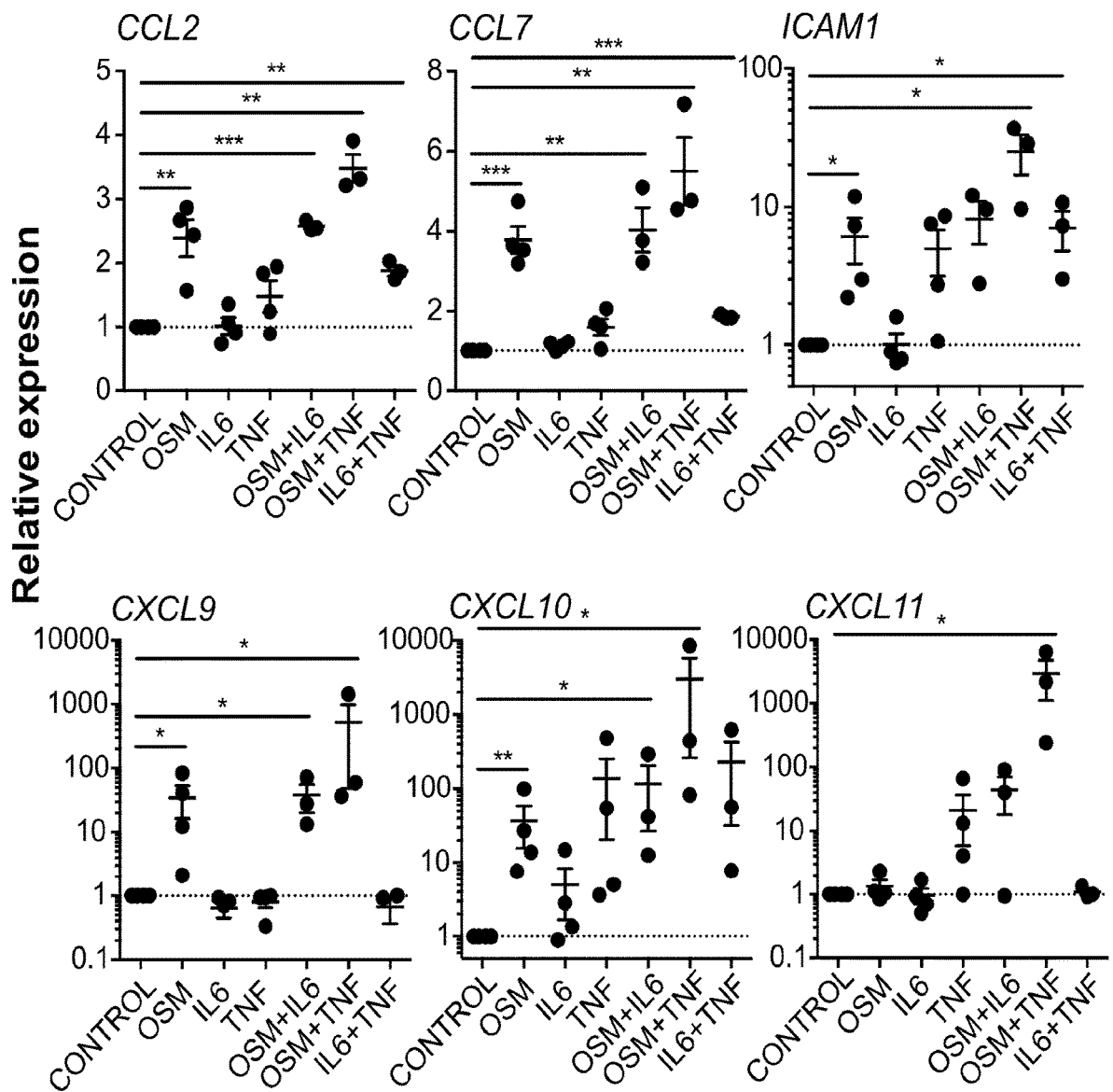

Example 18 OSM Stimulation of Human Intestinal Stromal Cells Triggers Activation of a Clinically Relevant Inflammatory Signature FIGS. 30 to 33 demonstrate that OSM correlates closely with a discrete group of cytokines and chemokines in a large cohort of IBD patients (FIG. 30). Enrichment of this gene signature generally denotes patients with features of severe disease, such as deep intestinal ulcerations, and is enriched in patients refractory to infliximab. Several genes in the signature, which execute various biological functions relevant to T cell and myeloid cell recruitment and retention, are directly regulated by OSM with varying kinetics in intestinal stromal cells (FIG. 31). As in mouse stromal cells, we observe clear evidence of functional synergy between OSM and TNF, particularly with respect to chemokines that promote Th1 cell recruitment (CXCL9/10/11) (FIG. 32). We observe similar synergy between OSM and IL-1β (FIG. 33). Notably, the effects of OSM on intestinal stromal cells are not mediated by the LIFR pathway, indicating that the gp130-OSMR heterodimer is the relevant OSM receptor complex in intestinal stromal cells (FIG. 31B). Data shown in FIG. 34 confirm using primary intestinal stromal cultures from several donors that OSM directly modulates expression of several genes found in the clinical expression signature (FIG. 30), whereas IL-6 generally has much weaker effects. Collectively, these data argue that an important aspect of the OSM/OSMR axis in the intestine is its potential to sustain or amplify inflammatory stromal activation involving heightened chemokine and cytokine production, with the likely consequence of increased leukocyte infiltration and retention in the intestinal tissue and delayed resolution of inflammation.

OSMR is expressed by several cell types at various levels and OSM thus exerts pleiotropic effects. For example, OSMR is highly expressed under healthy conditions by endothelial cells and mesenchymal stromal cells, including those present in the intestine. OSMR levels can also increase during inflammation in these cell types. OSM stimulation of these cell types results in a variety of responses, including expression/activation of leukocyte adhesion receptors such as ICAM-1, increased proliferation, and expression of pro-inflammatory cytokines or chemokines such as IL-6 and CCL2. Aberrant activation and numerical expansion of stromal populations is a critical aspect of pathogenic fibrosis, and OSM-OSMR signalling may therefore promote damaging fibrotic responses such as those observed in Crohn's disease. Similarly, through its ability to promote cytokine/chemokine production, proliferation, and adhesion receptor expression in these cell types, OSM can enhance tissue vascularity, recruitment and retention of leukocytes, and local inflammatory processes. Furthermore, enhancement of epithelial proliferation by OSM, either directly or indirectly, may promote onset of dysplasia and neoplasia, a serious adverse event associated with chronic intestinal inflammation.

Haematopoietic cell types generally do not express high levels of OSMR under steady state conditions. However, OSMR expression is inducible in these cell types when cells are exposed to appropriate stimuli. In the case of T cells, OSMR expression requires activation via the T cell receptor (TCR) in combination with appropriate polarizing cytokines, such as IL-6. IL-6 is critical for the development of inflammatory Th17 CD4$^+$ T cells, which are thought to promote pathogenic inflammatory responses in various disorders including IBD, multiple sclerosis, arthritis, psoriasis, and cancer. When activated under Th17-polarizing conditions, CD4$^+$ T cells expand (increase in number) more efficiently in the presence of OSM, and express lower levels of genes related to alternative polarization states, such as the cytokine IL-4, a product of Th2 cells. In the inflamed human intestine, OSM is expressed in conjunction with cytokines known to promote Th17 development, including IL-6 and IL-1β. Intriguingly, while T cells express high levels of OSM upon activation, this is further enhanced by exposure to exogenous sources of OSM, as would occur in the context of interaction with stimulated antigen presenting cells. OSM may thus contribute to pathogenic inflammation through the augmentation of Th17-driven immune responses.

Like T cells, mononuclear phagocytes such as monocytes have low levels of OSMR expression while at rest, but can increase OSMR 10 to 100-fold when exposed to activating stimuli such as whole bacteria or purified bacterial molecules. They also produce high levels of OSM upon activation. Consistent with observations from intestinal tissue, OSM expression by microbe-stimulated monocytes is highly correlated with expression of Th17-polarizing cytokines such as IL-6, IL-1β, and IL-23. Furthermore, stimulation of bacteria-stimulated monocytes with OSM can increase their expression of inflammatory cytokines such as IL-23.

Collectively therefore, several lines of evidence based on analysis of human tissue, in vitro experiments, and preclinical in vivo models support the concept that OSM can act broadly to promote pathogenic inflammation, particularly in the context of mucosal surfaces where microbial stimuli are prominent, such as IBD and other gastrointestinal disorders. Because the primary in vivo colitis model used in this study (Hh+αIL10R) is refractory to TNF blockade (as well as blockade of IL-6 and IL-1β, OSM may be a particularly valuable clinical target for patients who fail currently approved biological therapies.

The invention claimed is:

1. A method of treating chronic intestinal inflammation and/or inflammatory bowel disease (IBD) in an individual, the method comprising:
   administering to the individual an antagonist of oncostatin-M (OSM) and/or an antagonist of OSM receptor-β (OSMR),
   wherein the antagonist is an anti-OSM or anti-OSMR antibody, antisense molecule, interfering RNA or aptamer, or a polynucleic acid encoding an anti-OSM or anti-OSMR antibody, or aptamer.

2. The method of treating chronic intestinal inflammation and/or IBD according to claim 1, wherein
   (i) the individual has been diagnosed or prognosed by a method that comprises measuring an increase in OSM and/or OSMR levels in the individual, and thereby diagnosing or prognosing the chronic intestinal inflammation and/or IBD in the individual, or
   (ii) the antagonist of OSM and/or OSMR inhibits Th17 CD4$^+$ T cells or development of the Th17 pathway.

3. The method of claim 1, in which the antagonist of OSM and/or OSMR is selected from the group consisting of: an anti-OSM antibody or an anti-OSMR antibody.

4. The method of claim 2, in which the measuring of OSM or OSMR in the individual is carried out on a biological sample from the individual, optionally wherein the biological sample is a blood sample, a serum sample, a stool sample, an intestinal biopsy, or a surgical resection sample.

* * * * *

SEQUENCE LISTING

```
<160> NUMBER OF SEQ ID NOS: 6

<210> SEQ ID NO 1
<211> LENGTH: 1686
<212> TYPE: DNA
<213> ORGANISM: Homo sapiens

<400> SEQUENCE: 1
cagacgctcc ctcagcaagg acagcagagg accagctaag agggagagaa gcaactacag      60
accccccctg aaaacaaccc tcagacgcca catcccctga caagctgcca ggcaggttct     120
cttcctctca catactgacc cacggctcca ccctctctcc cctggaaagg acaccatgag     180
cactgaaagc atgatccggg acgtggagct ggccgaggag gcgctcccca agaagacagg     240
ggggccccag ggctccaggc ggtgcttgtt cctcagcctc ttctccttcc tgatcgtggc     300
aggcgccacc acgctcttct gcctgctgca ctttggagtg atcggccccc agagggaaga     360 gttcccagg gacctctctc taatcagccc tctggcccag gcagtcagat catcttctcg      420
aaccccgagt gacaagcctg tagcccatgt tgtagcaaac cctcaagctg aggggcagct     480
ccagtggctg aaccgccggg ccaatgccct cctggccaat ggcgtggagc tgagagataa     540
ccagctggtg gtgccatcag agggcctgta cctcatctac tcccaggtcc tcttcaaggg     600
ccaaggctgc ccctccaccc atgtgctcct caccacacc atcagccgca tcgccgtctc      660
ctaccagacc aaggtcaacc tcctctctgc catcaagagc cctgccaga gggagacccc      720 agaggggct gaggccaagc cctggtatga gcccatctat ctgggagggg tcttccagct     780
ggagaagggt gaccgactca cgcgctgagat caatcggccc gactatctcg actttgccga    840
gtctgggcag gtctactttg ggatcattgc cctgtgagga ggacgaacat ccaaccttcc     900
caaacgcctc ccctgcccca tccctttat taccccctcc ttcagacacc ctcaacctct     960
tctggctcaa aaagagaatt gggggcttag ggtcggaacc caagcttaga actttaagca    1020
acaagaccac cacttcgaaa cctgggattc aggaatgtgt ggcctgcaca gtgaagtgct    1080
ggcaaccact aagaattcaa actggggcct ccagaactca ctggggccta cagctttgat    1140
ccctgacatc tggaatctgg agaccaggga gcctttggtt ctggccagaa tgctgcagga    1200
cttgagaaga cctcacctag aaattgacac aagtggacct taggccttcc tctctccaga    1260
tgtttccaga cttccttgag acacggagcc cagccctccc catggagcca gctccctcta    1320
tttatgtttg cacttgtgat tatttattat ttatttatta tttatttatt tacagatgaa    1380
tgtatttatt tgggagaccg gggtatcctg ggggacccaa tgtaggagct gccttggctc    1440
agacatgttt tccgtgaaaa cggagctgaa caataggctg ttcccatgta gccccctggc    1500
ctctgtgcct tcttttgatt atgttttta aaatatttat ctgattaagt tgtctaaaca    1560
atgctgattt ggtgaccaac tgtcactcat tgctgagcct ctgctcccca ggggagttgt    1620
gtctgtaatc gccctactat tcagtggcga gaaataaagt ttgcttagaa aagaaaaaaa    1680
aaaaaa                                                                1686

<210> SEQ ID NO 2
<211> LENGTH: 233
<212> TYPE: PRT
<213> ORGANISM: Homo sapiens
```

<400> SEQUENCE: 2

| | | | | | | | | | | | | | | |
|---|---|---|---|---|---|---|---|---|---|---|---|---|---|---|
|Met|Ser|Thr|Glu|Ser|Met|Ile|Arg|Asp|Val|Glu|Leu|Ala|Glu|Ala|
|1| | | |5| | | | |10| | | | |15|
|Leu|Pro|Lys|Lys|Thr|Gly|Gly|Pro|Gln|Gly|Ser|Arg|Arg|Cys|Leu|Phe|
| | | | |20| | | | |25| | | | |30|
|Leu|Ser|Leu|Phe|Ser|Phe|Leu|Ile|Val|Ala|Gly|Ala|Thr|Thr|Leu|Phe|
| | | | |35| | | | |40| | | | |45|
|Cys|Leu|Leu|His|Phe|Gly|Val|Ile|Gly|Pro|Gln|Arg|Glu|Glu|Phe|Pro|
|50| | | | |55| | | | |60| | | | |
|Arg|Asp|Leu|Ser|Leu|Ile|Ser|Pro|Leu|Ala|Gln|Ala|Val|Arg|Ser|Ser|
|65| | | | |70| | | | |75| | | | |80|
|Ser|Arg|Thr|Pro|Ser|Asp|Lys|Pro|Val|Ala|His|Val|Val|Ala|Asn|Pro|
| | | | |85| | | | |90| | | | |95|
|Gln|Ala|Glu|Gly|Gln|Leu|Gln|Trp|Leu|Asn|Arg|Arg|Ala|Asn|Ala|Leu|
| | | |100| | | | |105| | | | |110| |
|Leu|Ala|Asn|Gly|Val|Glu|Leu|Arg|Asp|Asn|Gln|Leu|Val|Val|Pro|Ser|
| | | |115| | | | |120| | | | |125| |
|Glu|Gly|Leu|Tyr|Leu|Ile|Tyr|Ser|Gln|Val|Leu|Phe|Lys|Gly|Gln|Gly|
| | |130| | | | |135| | | | |140| | |
|Cys|Pro|Ser|Thr|His|Val|Leu|Leu|Thr|His|Thr|Ile|Ser|Arg|Ile|Ala|
|145| | | |150| | | | |155| | | | |160|
|Val|Ser|Tyr|Gln|Thr|Lys|Val|Asn|Leu|Leu|Ser|Ala|Ile|Lys|Ser|Pro|
| | | | |165| | | | |170| | | | |175|
|Cys|Gln|Arg|Glu|Thr|Pro|Glu|Gly|Ala|Glu|Ala|Lys|Pro|Trp|Tyr|Glu|
| | | |180| | | | |185| | | | |190| |
|Pro|Ile|Tyr|Leu|Gly|Gly|Val|Phe|Gln|Leu|Glu|Lys|Gly|Asp|Arg|Leu|
| | |195| | | | |200| | | | |205| | |
|Ser|Ala|Glu|Ile|Asn|Arg|Pro|Asp|Tyr|Leu|Asp|Phe|Ala|Glu|Ser|Gly|
| | |210| | | | |215| | | | |220| | |
|Gln|Val|Tyr|Phe|Gly|Ile|Ile|Ala|Leu|
|225| | | |230| | | | |

<210> SEQ ID NO 3
<211> LENGTH: 1869
<212> TYPE: DNA
<213> ORGANISM: Homo sapiens

<400> SEQUENCE: 3

```
gtcaccccca gcgggcgcgg gccggagcac gggcacccag catgggggta ctgctcacac    60
agaggacgct gctcagtctg gtccttgcac tcctgtttcc aagcatggcg agcatggcgg   120
ctataggcag ctgctcgaaa gagtaccgcg tgctccttgg ccagctccag aagcagacag   180
atctcatgca ggacaccagc agactcctgg acccctatat acgtatccaa ggcctggatg   240
ttcctaaaact gagagagcac tgcagggagc gccccggggc cttccccagt gaggagaccc   300
tgaggggggct gggcaggcgg ggcttcctgc agaccctcaa tgccacactg gctgcgtcc   360
tgcacagact ggccgactta gagcagcgcc tccccaaggc ccaggatttg agaggtctg   420
ggctgaacat cgaggacttg agaagctgc agatggcgag ccgaacatc ctcgggctca   480
ggaacaacat ctactgcatg gcccagctgc tggacaactc agacacggct gagcccacga   540
aggctggccg gggggcctct cagccgccca ccccacccc tgcctcggat gcttttcagc   600
gcaagctgga gggctgcagg ttcctgcatg ctaccatcg cttcatgcac tcagtggggc   660
gggtcttcag caagtggggg gagagcccga accggagccg gagacacagc ccccaccagg   720
```

-continued

```
ccctgaggaa gggggtgcgc aggaccagac cctccaggaa aggcaagaga ctcatgacca    780
ggggacagct gccccggtag cctcgagagc accccttgcc ggtgaaggat gcggcaggtg    840
ctctgtggat gagaggaacc atcgcaggat gacagctccc gggtcccaa acctgttccc     900 ctctgctact agccactgag aagtgcactt taagaggtgg gagctgggca gacccctcta    960
cctcctccag gctgggagac agagtcaggc tgttgcgctc ccacctcagc cccaagttcc   1020
ccaggcccag tggggtggcc gggcgggcca cgcgggaccg actttccatt gattcagggg   1080
tctgatgaca caggctgact catggccggg ctgactgccc ccctgccttg ctccccgagg   1140
cctgccggtc cttccctctc atgacttgca gggccgttgc ccccagactt cctcctttcc   1200
gtgtttctga aggggaggtc acagcctgag ctggcctcct atgcctcatc atgtcccaaa   1260
ccagacacct ggatgtctgg gtgacctcac tttaggcagc tgtaacagcg gcagggtgtc   1320
ccaggagccc tgatccgggg gtccagggaa tggagctcag gtcccaggcc agccccgaag   1380
tcgccacgtg gcctggggca ggtcacttta cctctgtgga cctgttttct ctttgtgaag   1440
ctagggagtt agaggctgta caaggccccc actgcctgtc ggttgcttgg attccctgac   1500
gtaaggtgga tattaaaaat ctgtaaatca ggacaggtgg tgcaaatggc gctgggaggt   1560
gtacacggag gtctctgtaa aagcagaccc acctcccagc gccgggaagc ccgtcttggg   1620
tcctcgctgc tggctgctcc ccctggtggt ggatcctgga attttctcac gcaggagcca   1680
ttgctctcct agagggggtc tcagaaactg cgaggccagt tccttggagg gacatgacta   1740
atttatcgat tttatcaat ttttatcagt tttatattta taagccttat ttatgatgta    1800
tatttaatgt taatattgtg caaacttata tttaaaactt gcctggtttc taaaaaaaaa   1860
aaaaaaaaa                                                           1869
```

<210> SEQ ID NO 4
<211> LENGTH: 252
<212> TYPE: PRT
<213> ORGANISM: Homo sapiens

<400> SEQUENCE: 4

```
Met Gly Val Leu Leu Thr Gln Arg Thr Leu Leu Ser Leu Val Leu Ala
1               5                   10                  15

Leu Leu Phe Pro Ser Met Ala Ser Met Ala Ala Ile Gly Ser Cys Ser
            20                  25                  30

Lys Glu Tyr Arg Val Leu Leu Gly Gln Leu Gln Lys Gln Thr Asp Leu
        35                  40                  45

Met Gln Asp Thr Ser Arg Leu Leu Asp Pro Tyr Ile Arg Ile Gln Gly
    50                  55                  60

Leu Asp Val Pro Lys Leu Arg Glu His Cys Arg Glu Arg Pro Gly Ala
65                  70                  75                  80

Phe Pro Ser Glu Glu Thr Leu Arg Gly Leu Gly Arg Arg Gly Phe Leu
                85                  90                  95

Gln Thr Leu Asn Ala Thr Leu Gly Cys Val Leu His Arg Leu Ala Asp
            100                 105                 110

Leu Glu Gln Arg Leu Pro Lys Ala Gln Asp Leu Glu Arg Ser Gly Leu
        115                 120                 125

Asn Ile Glu Asp Leu Glu Lys Leu Gln Met Ala Arg Pro Asn Ile Leu
    130                 135                 140

Gly Leu Arg Asn Asn Ile Tyr Cys Met Ala Gln Leu Leu Asp Asn Ser
145                 150                 155                 160

Asp Thr Ala Glu Pro Thr Lys Ala Gly Arg Gly Ala Ser Gln Pro Pro
```

```
            165                 170                 175
Thr Pro Thr Pro Ala Ser Asp Ala Phe Gln Arg Lys Leu Glu Gly Cys
            180                 185                 190

Arg Phe Leu His Gly Tyr His Arg Phe Met His Ser Val Gly Arg Val
            195                 200                 205

Phe Ser Lys Trp Gly Glu Ser Pro Asn Arg Ser Arg His Ser Pro
210                 215                 220

His Gln Ala Leu Arg Lys Gly Val Arg Arg Thr Arg Pro Ser Arg Lys
225                 230                 235                 240

Gly Lys Arg Leu Met Thr Arg Gly Gln Leu Pro Arg
            245                 250

<210> SEQ ID NO 5
<211> LENGTH: 5556
<212> TYPE: DNA
<213> ORGANISM: Homo sapiens

<400> SEQUENCE: 5
gcgcttgccc cgcagctgat tcatagcccc ggcccgggcc gcctctgcac gtccgccccg      60
gagcccgcac ccgcgcccca cgcgccgccg aggactcggc ccggctcgtg gagcccttcg     120
cccgcggcgt gagtaccccc gacccgcccg tccccgctct gctcgcgccc tgccgctgcg     180
ccgccctcgg tggcttttcc gacgggcgag ccccgtgctg tgcgggaaag aatccgacaa     240
cttcgcagcc catcccggct ggacgcgacc gggagtgcag cagcccgttc ccctcctcgg     300
tgccgcctct gccagcgtt tgcttggctg ggctaccacc tgcgctcgga cggcgctcgg      360
agggtcctcg ccccggcct gcctacctga aaccagaac tgatggctct atttgcagtc       420
tttcagacaa cattcttctt aacattgctg tccttgagga cttaccagag tgaagtcttg     480
gctgaacgtt taccattgac tcctgtatca cttaaagttt ccaccaattc tacgcgtcag     540
agtttgcact acaatggac tgtccacaac cttccttatc atcaggaatt gaaaatggta      600
tttcagatcc agatcagtag gattgaaaca tccaatgtca tctgggtggg gaattacagc     660
accactgtga gtggaaccag ggttctgcat tggagctggg aatctgagct cccctttgga     720
tgtgccacac actttgtaag aataaagagt ttggtggacg atgccaagtt ccctgagcca     780
aatttctgga gcaactggag ttcctgggag gaagtcagtg tacaagattc tactggacag     840
gatatattgt tcgttttccc taagataag ctggtggaag aaggcaccaa tgttaccatt      900
tgttacgttt ctaggaacat tcaaaataat gtatcctgtt atttggaagg gaaacagatt     960
catggagaac aacttgatcc acatgtaact gcattcaact tgaatagtgt gcctttcatt    1020
aggaataaag ggacaaatat ctattgtgag gcaagtcaag gaaatgtcag tgaaggcatg    1080
aaaggcatcg ttcttttttgt ctcaaaagta cttgaggagc ccaaggactt ttcttgtgaa    1140
accgaggact tcaagacttt gcactgtact tgggatcctg ggacggacac tgccttgggg    1200
tggtctaaac aaccttccca agctacact ttatttgaat catttctgg ggaaaagaaa      1260 ctttgtacac acaaaaactg gtgtaattgg caaataactc aagactcaca agaaacctat    1320
aacttcacac tcatagctga aaattactta aggaagagaa gtgtcaatat ccttttaac     1380 ctgactcatc gagtttattt aatgaatcct tttagtgtca actttgaaaa tgtaaatgcc    1440
acaaatgcca tcatgacctg gaaggtgcac tccataagga taatttcac atatttgtgt    1500 cagattgaac tccatggtga aggaaaaatg atgcaataca atgttccat caaggtgaac    1560 ggtgagtact tcttaagtga actggaacct gccacagagt acatggcgcg agtacggtgt    1620
```

```
gctgatgcca gccacttctg gaaatggagt gaatggagtg gtcagaactt caccacactt    1680
gaagctgctc cctcagaggc ccctgatgtc tggagaattg tgagcttgga gccaggaaat    1740
catactgtga ccttattctg gaagccatta tcaaaactgc atgccaatgg aaagatcctg    1800
ttctataatg tagttgtaga aaacctagac aaaccatcca gttcagagct ccattccatt    1860
ccagcaccag ccaacagcac aaaactaatc cttgacaggt gttcctacca aatctgcgtc    1920
atagccaaca acagtgtggg tgcttctcct gcttctgtaa tagtcatctc tgcagacccc    1980
gaaaacaaag aggttgagga agaaagaatt gcaggcacag agggtggatt ctctctgtct    2040
tggaaacccc aacctggaga tgttataggc tatgttgtgg actggtgtga ccatacccag    2100
gatgtgctcg gtgatttcca gtggaagaat gtaggtccca ataccacaag cacagtcatt    2160
agcacagatg cttttaggcc aggagttcga tatgacttca gaatttatgg gttatctaca    2220
aaaaggattg cttgtttatt agagaaaaaa acaggatact ctcaggaact tgctccttca    2280
gacaaccctc acgtgctggt ggatacattg acatcccact ccttcactct gagttggaaa    2340
gattactcta ctgaatctca acctggtttt atacaagggt accatgtcta tctgaaatcc    2400
aaggcgaggc agtgccaccc acgatttgaa aaggcagttc tttcagatgg ttcagaatgt    2460
tgcaaataca aaattgacaa cccggaagaa aaggcattga ttgtggacaa cctaaagcca    2520
gaatccttct atgagttttt catcactcca ttcactagtg ctggtgaagg ccccagtgct    2580
acgttcacga aggtcacgac tccggatgaa cactcctcga tgctgattca tatcctactg    2640
cccatggttt tctgcgtctt gctcatcatg gtcatgtgct acttgaaaag tcagtggatc    2700
aaggagacct gttatcctga catccctgac ccttacaaga gcagcatcct gtcattaata    2760
aaattcaagg agaaccctca cctaataata atgaatgtca gtgactgtat cccagatgct    2820
attgaagttg taagcaagcc agaagggaca agatacagt tcctaggcac taggaagtca    2880
ctcacagaaa ccgagttgac taagcctaac tacctttatc tccttccaac agaaaagaat    2940
cactctggcc ctggccccctg catctgtttt gagaacttga cctataacca ggcagcttct    3000
gactctggct cttgtggcca tgttccagta tccccaaaag ccccaagtat gctgggacta    3060
atgacctcac ctgaaaatgt actaaaggca ctagaaaaaa actacatgaa ctccctggga    3120
gaaatcccag ctggagaaac aagtttgaat tatgtgtccc agttggcttc acccatgttt    3180
ggagacaagg acagtctccc aacaaaccca gtagaggcac cacactgttc agagtataaa    3240
atgcaaatgg cagtctccct gcgtcttgcc ttgcctcccc cgaccgagaa tagcagcctc    3300
tcctcaatta cccttttaga tccaggtgaa cactactgct aaccagcatg ccgatttcat    3360
accttatgct acacagacat taagaagagc agagctggca ccctgtcatc accagtggcc    3420
ttggtcctta atcccagtac gatttgcagg tctggtttat ataagaccac tacagtctgg    3480
ctaggttaaa ggccagaggc tatggaactt aacactcccc attggagcaa gcttgcccta    3540
gagacggcag gatcatggga gcatgcttac cttctgctgt tgttccagg ctcacccttta    3600 gaacaggaga cttgagcttg acctaaggat atgcattaac cactctacag actcccactc    3660
agtactgtac agggtggctg tggtcctaga agttcagttt ttactgagga aatatttcca    3720
ttaacagcaa ttattatatt gaaggcttta ataaaggcca caggagacat tactatagca    3780
tagattgtca aatgtaaatt tactgagcgt gttttataaa aaactcacag gtgtttgagg    3840
ccaaaacaga ttttagactt accttgaacg gataagaatc tatagttcac tgacacagta    3900
aaattaactc tgtgggtggg ggcgggggggc atagctctaa tctaatatat aaatgtgtg    3960 atgaatcaac aagatttcca caattcttct gtcaagctta ctacagtgaa agaatgggat    4020
```

-continued

```
tggcaagtaa cttctgactt actgtcagtt gtacttctgc tccatagaca tcagtattct   4080
gccatcattt ttgatgacta cctcagaaca taaaaaggaa cgtatatcac ataattccag   4140
tcacagtttt tggttcctct tttctttcaa gaactatata taaatgacct gttttcactt   4200
agcatccttt ggactctgca gtaggttgtc tgggtcaaga taactctcag tcacatttat   4260
attcatatta tgctaaaata gtaaaatgaa acctcattgt tggacataat ttagatataa   4320
ctaaaaagtt ctatgaagtg ggaaattccg tgttggctct ggagcagctt tgtctcctct   4380
gaaccaatat atcccaaacc aatatatgca aagcacctgg tacacaactg gtattttagt   4440
acatgttggt tcttttggtg caatctcagc tcactgcagc ttccgcctcc tagattcaaa   4500
caaacagttc tcctgcccca gcctccagag cacctaggac tccaggtgca tgctaccaca   4560
cctgactagt ttttatattt ttagtagaga ttgggtttta ccatattggc caggctggtc   4620
tcaaactcct gaccgcaggt gatccacctg cctcagcttc ccaagggct gggattacag   4680 gtgtgagcca ccatgcccag cctatttgtc acattatttg tcacatttat tttacttta   4740 tttattttt gagatgaaat ttcgctcttg ttgcccaggc tggagtgcaa tggtgcagcc   4800
ttggctcact gcaacctccg cctcccaggg tcaagcaatt ctcctgcctc agcctcctga   4860
gtagctggga ttacaggcat gcaccaccac acccaggtaa ttttgtatct ttagtagaga   4920
tggggtttca ccatgttggt caggctgttc tcgaactcct gacctcaggt gatctgcctg   4980
ccttggcctc ccaaagtgct gggattacag gcgtgagcca ctgcgcctag ccgtcacatt   5040
tctaaacaag catgaaaggg gttcattttt gtcttcttct tgcctgccgt cagcatggtg   5100
gaaatggctc tgcctatgct catgcttctg gtgcccaatg ccttgcactg tgccattcaa   5160
cactatgaag agaaacaagt agccacacct caaaataatg tggctgtcaa caactggcct   5220
aaataaacct acacaaacca gtacttgcct tttgctggaa acattgatta tgtgctcctc   5280
acgtagtaga aagcggtatc ctgattagtc taacagttgt gttagacttt agggccagta   5340
ttgtcagcat ttatttattt atgtaccttt gttatgatgg gatattttc atttgaaact   5400 tgttcataaa aatgtcaatg acattgatga ctgatttgta catattttc atatagtttt   5460 gtttaaaaaa taattcacgc aaaatcttga agtcattttt gctattgaaa taaaccttaa   5520
ttaaaatatt tcatcatcaa aaaaaaaaaa aaaaaa                            5556
```

<210> SEQ ID NO 6
<211> LENGTH: 979
<212> TYPE: PRT
<213> ORGANISM: Homo sapiens

<400> SEQUENCE: 6

```
Met Ala Leu Phe Ala Val Phe Gln Thr Thr Phe Phe Leu Thr Leu Leu
1               5                   10                  15

Ser Leu Arg Thr Tyr Gln Ser Glu Val Leu Ala Glu Arg Leu Pro Leu
                20                  25                  30

Thr Pro Val Ser Leu Lys Val Ser Thr Asn Ser Thr Arg Gln Ser Leu
            35                  40                  45

His Leu Gln Trp Thr Val His Asn Leu Pro Tyr His Gln Glu Leu Lys
        50                  55                  60

Met Val Phe Gln Ile Gln Ile Ser Arg Ile Glu Thr Ser Asn Val Ile
65                  70                  75                  80

Trp Val Gly Asn Tyr Ser Thr Thr Val Lys Trp Asn Gln Val Leu His
                85                  90                  95
```

```
Trp Ser Trp Glu Ser Glu Leu Pro Leu Glu Cys Ala Thr His Phe Val
            100                 105                 110

Arg Ile Lys Ser Leu Val Asp Asp Ala Lys Phe Pro Glu Pro Asn Phe
        115                 120                 125

Trp Ser Asn Trp Ser Ser Trp Glu Glu Val Ser Val Gln Asp Ser Thr
    130                 135                 140

Gly Gln Asp Ile Leu Phe Val Phe Pro Lys Asp Lys Leu Val Glu Glu
145                 150                 155                 160

Gly Thr Asn Val Thr Ile Cys Tyr Val Ser Arg Asn Ile Gln Asn Asn
                165                 170                 175

Val Ser Cys Tyr Leu Glu Gly Lys Gln Ile His Gly Glu Gln Leu Asp
            180                 185                 190

Pro His Val Thr Ala Phe Asn Leu Asn Ser Val Pro Phe Ile Arg Asn
        195                 200                 205

Lys Gly Thr Asn Ile Tyr Cys Glu Ala Ser Gln Gly Asn Val Ser Glu
    210                 215                 220

Gly Met Lys Gly Ile Val Leu Phe Val Ser Lys Val Leu Glu Glu Pro
225                 230                 235                 240

Lys Asp Phe Ser Cys Glu Thr Glu Asp Phe Lys Thr Leu His Cys Thr
                245                 250                 255

Trp Asp Pro Gly Thr Asp Thr Ala Leu Gly Trp Ser Lys Gln Pro Ser
            260                 265                 270

Gln Ser Tyr Thr Leu Phe Glu Ser Phe Ser Gly Glu Lys Lys Leu Cys
        275                 280                 285

Thr His Lys Asn Trp Cys Asn Trp Gln Ile Thr Gln Asp Ser Gln Glu
    290                 295                 300

Thr Tyr Asn Phe Thr Leu Ile Ala Glu Asn Tyr Leu Arg Lys Arg Ser
305                 310                 315                 320

Val Asn Ile Leu Phe Asn Leu Thr His Arg Val Tyr Leu Met Asn Pro
                325                 330                 335

Phe Ser Val Asn Phe Glu Asn Val Asn Ala Thr Asn Ala Ile Met Thr
            340                 345                 350

Trp Lys Val His Ser Ile Arg Asn Asn Phe Thr Tyr Leu Cys Gln Ile
        355                 360                 365

Glu Leu His Gly Glu Gly Lys Met Met Gln Tyr Asn Val Ser Ile Lys
    370                 375                 380

Val Asn Gly Glu Tyr Phe Leu Ser Glu Leu Glu Pro Ala Thr Glu Tyr
385                 390                 395                 400

Met Ala Arg Val Arg Cys Ala Asp Ala Ser His Phe Trp Lys Trp Ser
                405                 410                 415

Glu Trp Ser Gly Gln Asn Phe Thr Thr Leu Glu Ala Ala Pro Ser Glu
            420                 425                 430

Ala Pro Asp Val Trp Arg Ile Val Ser Leu Glu Pro Gly Asn His Thr
        435                 440                 445

Val Thr Leu Phe Trp Lys Pro Leu Ser Lys Leu His Ala Asn Gly Lys
    450                 455                 460

Ile Leu Phe Tyr Asn Val Val Val Glu Asn Leu Asp Lys Pro Ser Ser
465                 470                 475                 480

Ser Glu Leu His Ser Ile Pro Ala Pro Ala Asn Ser Thr Lys Leu Ile
                485                 490                 495

Leu Asp Arg Cys Ser Tyr Gln Ile Cys Val Ile Ala Asn Asn Ser Val
            500                 505                 510

Gly Ala Ser Pro Ala Ser Val Ile Val Ile Ser Ala Asp Pro Glu Asn
```

```
            515                 520                 525
Lys Glu Val Glu Glu Arg Ile Ala Gly Thr Glu Gly Phe Ser
        530                 535                 540

Leu Ser Trp Lys Pro Gln Pro Gly Asp Val Ile Gly Tyr Val Val Asp
545                 550                 555                 560

Trp Cys Asp His Thr Gln Asp Val Leu Gly Asp Phe Gln Trp Lys Asn
                565                 570                 575

Val Gly Pro Asn Thr Thr Ser Thr Val Ile Ser Thr Asp Ala Phe Arg
                580                 585                 590

Pro Gly Val Arg Tyr Asp Phe Arg Ile Tyr Gly Leu Ser Thr Lys Arg
                595                 600                 605

Ile Ala Cys Leu Leu Glu Lys Lys Thr Gly Tyr Ser Gln Glu Leu Ala
                610                 615                 620

Pro Ser Asp Asn Pro His Val Leu Val Asp Thr Leu Thr Ser His Ser
625                 630                 635                 640

Phe Thr Leu Ser Trp Lys Asp Tyr Ser Thr Glu Ser Gln Pro Gly Phe
                645                 650                 655

Ile Gln Gly Tyr His Val Tyr Leu Lys Ser Lys Ala Arg Gln Cys His
                660                 665                 670

Pro Arg Phe Glu Lys Ala Val Leu Ser Asp Gly Ser Glu Cys Cys Lys
                675                 680                 685

Tyr Lys Ile Asp Asn Pro Glu Glu Lys Ala Leu Ile Val Asp Asn Leu
                690                 695                 700

Lys Pro Glu Ser Phe Tyr Glu Phe Phe Ile Thr Pro Phe Thr Ser Ala
705                 710                 715                 720

Gly Glu Gly Pro Ser Ala Thr Phe Thr Lys Val Thr Thr Pro Asp Glu
                725                 730                 735

His Ser Ser Met Leu Ile His Ile Leu Leu Pro Met Val Phe Cys Val
                740                 745                 750

Leu Leu Ile Met Val Met Cys Tyr Leu Lys Ser Gln Trp Ile Lys Glu
                755                 760                 765

Thr Cys Tyr Pro Asp Ile Pro Asp Pro Tyr Lys Ser Ser Ile Leu Ser
                770                 775                 780

Leu Ile Lys Phe Lys Glu Asn Pro His Leu Ile Ile Met Asn Val Ser
785                 790                 795                 800

Asp Cys Ile Pro Asp Ala Ile Glu Val Val Ser Lys Pro Glu Gly Thr
                805                 810                 815

Lys Ile Gln Phe Leu Gly Thr Arg Lys Ser Leu Thr Glu Thr Glu Leu
                820                 825                 830

Thr Lys Pro Asn Tyr Leu Tyr Leu Leu Pro Thr Glu Lys Asn His Ser
                835                 840                 845

Gly Pro Gly Pro Cys Ile Cys Phe Glu Asn Leu Thr Tyr Asn Gln Ala
                850                 855                 860

Ala Ser Asp Ser Gly Ser Cys Gly His Val Pro Val Ser Pro Lys Ala
865                 870                 875                 880

Pro Ser Met Leu Gly Leu Met Thr Ser Pro Glu Asn Val Leu Lys Ala
                885                 890                 895

Leu Glu Lys Asn Tyr Met Asn Ser Leu Gly Glu Ile Pro Ala Gly Glu
                900                 905                 910

Thr Ser Leu Asn Tyr Val Ser Gln Leu Ala Ser Pro Met Phe Gly Asp
                915                 920                 925

Lys Asp Ser Leu Pro Thr Asn Pro Val Glu Ala Pro His Cys Ser Glu
                930                 935                 940
```

```
Tyr Lys Met Gln Met Ala Val Ser Leu Arg Leu Ala Leu Pro Pro Pro
945                 950                 955                 960

Thr Glu Asn Ser Ser Leu Ser Ser Ile Thr Leu Leu Asp Pro Gly Glu
                965                 970                 975

His Tyr Cys
```